(12) United States Patent
Schalk et al.

(10) Patent No.: US 7,273,735 B2
(45) Date of Patent: Sep. 25, 2007

(54) SESQUITERPENE SYNTHASES AND METHODS OF USE

(75) Inventors: Michel Schalk, Collonges-Sous-Saleve (FR); Anthony Clark, Monnetier Mornex (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 11/094,607

(22) Filed: Mar. 30, 2005

(65) Prior Publication Data

US 2005/0210549 A1   Sep. 22, 2005

Related U.S. Application Data

(63) Continuation of application No. PCT/IB03/05072, filed on Oct. 2, 2003.

(60) Provisional application No. 60/415,765, filed on Oct. 4, 2002.

(30) Foreign Application Priority Data

Dec. 2, 2002 (WO) ........................ PCT/IB02/05070

(51) Int. Cl.
| | |
|---|---|
| C12Q 1/68 | (2006.01) |
| C12P 7/02 | (2006.01) |
| C12P 5/00 | (2006.01) |
| C12P 21/06 | (2006.01) |
| C12N 9/10 | (2006.01) |
| C12N 15/70 | (2006.01) |
| C07H 21/04 | (2006.01) |

(52) U.S. Cl. ..................... 435/166; 435/155; 435/6; 435/488; 435/193; 435/69.1; 435/320.1; 536/23.2

(58) Field of Classification Search ................ 435/155, 435/166, 193, 69.1
See application file for complete search history.

(56) References Cited

FOREIGN PATENT DOCUMENTS

EP   1 040 765 A1   10/2000

WO   WO2005/021705 A2 *   3/2005

OTHER PUBLICATIONS

Xia et al. (UniProt Q8RVR2, Putative terpene synthase, created Jun. 1, 2002).*
Guo et al. Protein tolerance to random amino acid chang, Proc Natl Acad Sci U S A, Jun. 22, 2004; 101(25): 9205-10, Epub Jun. 14, 2004.*
Abstract: D. Xia et al., XP 002304705, "Putative Terpene Synthase", PRT, 548 AA, (2002).
Abstract: XP 002282507, "Isolation Of A Terpene Synthase Gene From Mature 'Rio Red' grapefruit using differential display" (2001).
Liat Sharon-Asa et al., XP-002282506, "Citrus Fruit Flavor And Aroma Biosynthesis: Isolation, Functional Characterization, And Developmental Regulation Of Cstps 1, A Key Gene In The Production Of The Sesquiterpene Aroma Compound Valencene", The Plant Journal, vol. 36, pp. 664-674 (2003).
Susan C. Trapp et al, XP-002282505, "Genomic Organization of Plant Terpene Synthases and Molecular Evolutionary Implications", Genetics Society of America, vol. 158, pp. 811-832, (2001).
Jörg Bohlmann et al., XP-002171016, "Plant Terpenoid Synthases: Molecular Biology And Phylogenetic Analysis", Proc.. Natl. Acad. Sci. USA, Biochemistry, vol. 95, pp. 4126-4133, (1998).
Takuro Maruyama et al., XP-002282504, "Molecular Cloning, Functional Expression and Characterization of (E)-βFarnesene Synthase from *Citrus junos*", Biol. Pharm. Bull., vol. 24, No. 10, pp. 1171-1175( 2001).

* cited by examiner

Primary Examiner—Rebecca E. Prouty
Assistant Examiner—Iqbal Chowdhury
(74) Attorney, Agent, or Firm—Winston & Strawn LLP

(57) ABSTRACT

The invention relates to sesquiterpene synthases and methods of their production and use. In one embodiment, the invention provides nucleic acids comprising a nucleotide sequence as described herein that encodes for at least one sesquiterpene synthases. In a further embodiment, the invention also provides for sesquiterpene synthases and methods of making and using these enzymes. For example, sesquiterpene synthases of the invention may be used to convert farnesyl-pyrophosphate to various oxygenated and aliphatic sesquiterpenes including valencene, bicyclo-germacrene, cubebol and delta-cadinene.

14 Claims, 18 Drawing Sheets

```
              10         20         30         40
GFTpsA   DLGFPKKVPY ARDRVVETYI WMLLGVSYEP NLAFGRIFAS KVVCIISII
GFTpsB   ---------- ---------- --IVGTYFEP KYTLARKIMT KTIYTASII
GFTpsC   ---------- ---------- ---MGVYFEP RYSFARKILS KVIAMASIL
```

GFTpsA

| | | | | | | | | | | | | | | | |
|---|---|---|---|---|---|---|---|---|---|---|---|---|---|---|---|
| 1 | CAA | AAA | CTA | CAC | ATG | ATT | GAT | GCA | GCA | CAA | CGA | TTA | GGT | GTC | GCT | 45 |
| 1 | Q | K | L | H | M | I | D | A | A | Q | R | L | G | V | A | 15 |
| 46 | TAT | CAT | TTT | GAA | AAA | GAG | ATT | GAA | GAT | GAA | TTG | GGA | AAG | GTA | TCT | 90 |
| 16 | Y | H | F | E | K | E | I | E | D | E | L | G | K | V | S | 30 |
| 91 | CAT | GAT | CTT | GAC | AGT | GAT | GAT | CTA | TAC | GTT | GTT | TCT | CTT | CGT | TTT | 135 |
| 31 | H | D | L | D | S | D | D | L | Y | V | V | S | L | R | F | 45 |
| 136 | CGA | CTT | TTT | AGA | CAG | CAA | GGA | GTT | AAG | ATT | TCA | TGT | GAT | GTG | TTT | 180 |
| 46 | R | L | F | R | Q | Q | G | V | K | I | S | C | D | V | F | 60 |
| 181 | GAG | AAG | TTC | AAA | GAT | GAC | GAA | GGT | AAA | TTC | AAG | GAA | TCA | TTG | ATC | 225 |
| 61 | E | K | F | K | D | D | E | G | K | F | K | E | S | L | I | 75 |
| 226 | AAC | GAT | ATA | CGA | GGC | ATG | TCG | AGT | TTG | TAC | GAG | GCA | GCA | TAC | CTA | 270 |
| 76 | N | D | I | R | G | M | S | S | L | Y | E | A | A | Y | L | 90 |
| 271 | GCA | ATT | CGG | GGG | GAA | GAC | ATT | TTA | GAT | GAA | GCC | ATT | GTT | TTC | ACT | 315 |
| 91 | A | I | R | G | E | D | I | L | D | E | A | I | V | F | T | 105 |
| 316 | ACC | ACT | CAC | CTT | AAG | TCA | GTA | ATA | TCT | GTA | TCT | GAT | CAT | TCT | CAT | 360 |
| 106 | T | T | H | L | K | S | V | I | S | V | S | D | H | S | H | 120 |
| 361 | GTA | AAC | TCT | GAT | CTT | GCT | GAA | CAA | ATA | CGT | CAT | TCT | CTG | CAA | ATT | 405 |
| 121 | V | N | S | D | L | A | E | Q | I | R | H | S | L | Q | I | 135 |
| 406 | CCT | CTC | CGT | AAA | GCC | GCA | GCA | AGG | TTA | GAG | GCA | AGG | TAT | TTT | TTG | 450 |
| 136 | P | L | R | K | A | A | A | R | L | E | A | R | Y | F | L | 150 |
| 451 | GAT | ATC | TAT | TCA | AGG | GAT | GAT | TTG | CAT | GAT | GAA | ACT | TTG | CTC | AAG | 495 |
| 151 | D | I | Y | S | R | D | D | L | H | D | E | T | L | L | K | 165 |
| 496 | TTT | GCA | AAG | TTA | GAC | TTT | AAT | ATA | TTA | CAA | GCA | GCA | CAC | AAG | AAG | 540 |
| 166 | F | A | K | L | D | F | N | I | L | Q | A | A | H | K | K | 180 |
| 541 | GAA | GCA | AGT | ATC | ATG | ACC | AGG | TGG | TGG | AAC | GAT | TTA | GGC | TTC | CCT | 585 |
| 181 | E | A | S | I | M | T | R | W | W | N | D | L | G | F | P | 195 |
| 586 | AAA | AAG | GTG | CCT | TAT | GCA | AGA | GAT | AGA | GTA | GTA | GAG | ACA | TAT | ATT | 630 |
| 196 | K | K | V | P | Y | A | R | D | R | V | V | E | T | Y | I | 210 |
| 631 | TGG | ATG | TTG | CTG | GGA | GTG | TCC | TAT | GAG | CCC | AAT | TTG | GCA | TTT | GGT | 675 |
| 211 | W | M | L | L | G | V | S | Y | E | P | N | L | A | F | G | 225 |
| 676 | AGA | ATT | TTT | GCA | TCC | AAA | GTG | GTG | TGC | ATA | ATA | TCC | ATA | ATA | GAC | 720 |
| 226 | R | I | F | A | S | K | V | V | C | I | I | S | I | I | D | 240 |
| 721 | GAC | ACA | TTT | GAT | GCT | TAC | GGT | ACT | TTT | GAA | GAG | CTC | ACA | CTT | TTT | 765 |
| 241 | D | T | F | D | A | Y | G | T | F | E | E | L | T | L | F | 255 |
| 766 | ACT | GAA | GCA | GTC | ACA | 780 | | | | | | | | | | |
| 256 | T | E | A | V | T | | | | | | | | | | | |

Figure 8(b)

GFTpsB

```
1     ATG TCC GCT CAA GTT CTA GCA ACG GTT TCC AGT TCG ACA GAA AAA    45
1      M   S   A   Q   V   L   A   T   V   S   S   S   T   E   K    15

46    ACT GTT CGT CCC ATT GCT GGT TTC CAT CCT AAC TTA TGG GGA GAC    90
16     T   V   R   P   I   A   G   F   H   P   N   L   W   G   D    30

91    TAT TTC CTG ACC CTC GCT TCT GAT TGC AAG ACA GAT GAT ACT ACG   135
31     Y   F   L   T   L   A   S   D   C   K   T   D   D   T   T    45

136   CAC CAA GAG GAA TAC GAA GCG CTG AAG CAA GAA GTC AGA AGC ATG   180
46     H   Q   E   E   Y   E   A   L   K   Q   E   V   R   S   M    60

181   ATA ACG GCT ACG GCA GAT ACA CCT GCC CAG AAG TTG CAA TTG GTT   225
61     I   T   A   T   A   D   T   P   A   Q   K   L   Q   L   V    75

226   GAT GCA GTC CAA CGA TTG GGT GTG GCC TAT CAC TTC GAA CAG GAG   270
76     D   A   V   Q   R   L   G   V   A   Y   H   F   E   Q   E    90

271   ATA GAA GAT GCA ATG GAA AAG ATT TAT CAC GAT GAC TTT GAT AAT   315
91     I   E   D   A   M   E   K   I   Y   H   D   D   F   D   N   105

316   AAC GAT GAT GTC GAT CTC TAC ACT GTT TCT CTT CGT TTT CGA CTG   360
106    N   D   D   V   D   L   Y   T   V   S   L   R   F   R   L   120

361   CTT AGG CAG CAA GGA TTT AAG GTT CCG TGT GAT GTG TTC GCG AAG   405
121    L   R   Q   Q   G   F   K   V   P   C   D   V   F   A   K   135

406   TTC AAA GAT GAT GAA GGT AAA TTC AAG GCA TCA TTG GTG CGG GAT   450
136    F   K   D   D   E   G   K   F   K   A   S   L   V   R   D   150

451   GTT CAT GGC ATT CTA AGT TTG TAT GAG GCA GGA CAC TTG GCC ATT   495
151    V   H   G   I   L   S   L   Y   E   A   G   H   L   A   I   165

496   CGC GGA GAA GGG ATA TTA GAT GAA GCC ATT GCT TTC ACT AGA ACT   540
166    R   G   E   G   I   L   D   E   A   I   A   F   T   R   T   180

541   CAC CTT CAG TCA ATG GTA TCT CAG GAT GTA TGC CCT AAT AAT CTT   585
181    H   L   Q   S   M   V   S   Q   D   V   C   P   N   N   L   195

586   GCT GAA CAA ATT AAT CAT ACT CTC GAC TGT CCT CTC CGC AGA GCC   630
196    A   E   Q   I   N   H   T   L   D   C   P   L   R   R   A   210

631   CTT CCA AGA GTG GAG ACA AGA TTT TTC TTG TCG GTC TAT CCA AGA   675
211    L   P   R   V   E   T   R   F   F   L   S   V   Y   P   R   225

676   GAT GAT AAA CAC GAT AAA ACT TTG TTA AAG TTT TCA AAG TTA GAC   720
226    D   D   K   H   D   K   T   L   L   K   F   S   K   L   D   240

721   TTT AAC CTT GTG CAA AGA ATA CAT CAG AAG GAA TTA AGT GCC ATC   765
241    F   N   L   V   Q   R   I   H   Q   K   E   L   S   A   I   255

766   ACA CGG TGG TGG AAA GAT TTA GAC TTC ACT ACA AAG CTA CCT TAT   810
256    T   R   W   W   K   D   L   D   F   T   T   K   L   P   Y   270

811   GCA AGA GAC AGA ATC GTA GAG TTG TAT TTT TGG ATT GTA GGG ACG   855
271    A   R   D   R   I   V   E   L   Y   F   W   I   V   G   T   285

856   TAT TTT GAA CCA AAG TAC ACT TTA GCA AGA AAA ATA ATG ACC AAA   900
286    Y   F   E   P   K   Y   T   L   A   R   K   I   M   T   K   300

901   ACA ATT TAC ACG GCA TCT ATC ATA GAT GAC ACT TTC GAC GCT TAT   945
301    T   I   Y   T   A   S   I   I   D   D   T   F   D   A   Y   315
```

Figure 8(b) continued

```
946   GGT TTC TTT GAA GAG CTC AAA CTC TTT GCA GAA GCA GTC CAG AGG   990
316    G   F   F   E   E   L   K   L   F   A   E   A   V   Q   R   330

991   TGG GAC ATT GGA GCC ATG GAT ATA CTT CCA GAA TAC ATG AAA GTG   1035
331    W   D   I   G   A   M   D   I   L   P   E   Y   M   K   V   345

1036  CTT TAT AAG GCC CTT TTA GAT ACT TTC AAT GAA ATT GAG CAA GAC   1080
346    L   Y   K   A   L   L   D   T   F   N   E   I   E   Q   D   360

1081  TTG GCC AAG GAA GGA AGA TCG TCC TAC TTA CCT TAT GGC AAA GAA   1125
361    L   A   K   E   G   R   S   S   Y   L   P   Y   G   K   E   375

1126  AAG ATG CAA GAG CTT GTT CAA ATG TAC TTT GTT CAA GCC AAG TGG   1170
376    K   M   Q   E   L   V   Q   M   Y   F   V   Q   A   K   W   390

1171  TTC AGT GAA GGT TAT GTT CCG ACA TGG GAC GAA TAT TAT CCG GTT   1215
391    F   S   E   G   Y   V   P   T   W   D   E   Y   Y   P   V   405

1216  GGA CTT GTA AGT TGC GGC TAC TTC ATG CTT GCG ACA AAC TCC TTC   1260
406    G   L   V   S   C   G   Y   F   M   L   A   T   N   S   F   420

1261  CTT GGC ATG TGT GAT GTT GCA AAC GAG GAA GCT TTT GAA TGG ATA   1305
421    L   G   M   C   D   V   A   N   E   E   A   F   E   W   I   435

1306  TCC AAG GAC CCT AAG ATT TCA ACA GCG TCA TCA GTT ATC TGC AGA   1350
436    S   K   D   P   K   I   S   T   A   S   S   V   I   C   R   450

1351  CTT AGG AAT GAC ATT GTT TCC CAC CAG TTT GAA CAG AAG AGA GGA   1395
451    L   R   N   D   I   V   S   H   Q   F   E   Q   K   R   G   465

1396  CAT ATT GCC TCA GGA TTT GAA TGC TAC ATT AAG CAG TAT GGT GTT   1440
466    H   I   A   S   G   F   E   C   Y   I   K   Q   Y   G   V   480

1441  TCA GAA GAA GAG GTA GTT ACA GTT TTT ACT GAA GAA GTT GAG AAT   1485
481    S   E   E   E   V   V   T   V   F   T   E   E   V   E   N   495

1486  GCA TGG AAA GAT ATG AAT GAG GAA TTC CTG AAA CCA ACT GCT TTT   1530
496    A   W   K   D   M   N   E   E   F   L   K   P   T   A   F   510

1531  CCT GTG GCT TTG ATT GAG AGA CCT TTC AAT ATC GCA CGT GTG ATT   1575
511    P   V   A   L   I   E   R   P   F   N   I   A   R   V   I   525

1576  GAA TTT CTA AAC AAG AAG GGT GAT TGG TAC ACT CAT TCT CAT GCG   1620
526    E   F   L   N   K   K   G   D   W   Y   T   H   S   H   A   540

1621  ATT AAA GAC CAG ATT GCC GCA GTG CTC AGA GAC CCT GTT ACC ATC   1665
541    I   K   D   Q   I   A   A   V   L   R   D   P   V   T   I   555
```

Figure 8(c)

GFTpsC

```
1     ATG GCA CTT CAA GAT TCA GAA GTT CCT TCT TCC ATT CTG AAT GCT    45
1      M   A   L   Q   D   S   E   V   P   S   S   I   L   N   A    15

46    ACA GCC GGC AAC CGT CCC ACA GCT AGT TAT CAT CCC ACC CTC TGG    90
16     T   A   G   N   R   P   T   A   S   Y   H   P   T   L   W    30

91    GGG GGA AAA TTC CTT GAC TAT TCT TCT GTT GAC GAC TCT GAG GCA   135
31     G   G   K   F   L   D   Y   S   S   V   D   D   S   E   A    45

136   ATG GAT GCC ACA ATT GAT CAA GAC GAA TTT GAA GCA CTT AAG CAA   180
46     M   D   A   T   I   D   Q   D   E   F   E   A   L   K   Q    60

181   AAA ATA AAG AAC ATG TTA ATC TCA CCA ACC GAT AAG TCT TTT CAA   225
61     K   I   K   N   M   L   I   S   P   T   D   K   S   F   Q    75

226   AAA TTG AAC TTG ATT GAT GCC GTC CAA CGC TTA GGA GTG GCT TAC   270
76     K   L   N   L   I   D   A   V   Q   R   L   G   V   A   Y    90

271   CAT TTT GAG AGG GAG ATA GAA GAT GAA CTA GAA AAA CTA TCT CCT   315
91     H   F   E   R   E   I   E   D   E   L   E   K   L   S   P   105

316   GAT GAG TAT GAT GGC AAC GAT GTA CAC TCC GTT GCT CTT CGA TTT   360
106    D   E   Y   D   G   N   D   V   H   S   V   A   L   R   F   120

361   CGG TTA CTC AGA CAA CAA GGA TAT CGC ATA TCA TGC GAT ATT TTT   405
121    R   L   L   R   Q   Q   G   Y   R   I   S   C   D   I   F   135

406   GGC GGT TTC AAA GAT GAT CGA GGA AAG TTC AAG GTA TCC TTA ATT   450
136    G   G   F   K   D   D   R   G   K   F   K   V   S   L   I   150

451   AAT GAT GTG ACC GGC ATG CTA AGT TTG TAT GAG GCT GCA CAT CTT   495
151    N   D   V   T   G   M   L   S   L   Y   E   A   A   H   L   165

496   CGC ATT CGC GGG GAA GAT ATC CTG GAT GAA GCC CTA GCT TTC ACT   540
166    R   I   R   G   E   D   I   L   D   E   A   L   A   F   T   180

541   ACT TCT CAC CTG GAA TCA ATG GTT ACT CAA GTA AGC CCT CAG CTT   585
181    T   S   H   L   E   S   M   V   T   Q   V   S   P   Q   L   195

586   TCT GAT GAA ATA CTT CAT GCC TTG AAT AGG CCA ATC CGC AGA GGC   630
196    S   D   E   I   L   H   A   L   N   R   P   I   R   R   G   210

631   TTA CCA AGG CTG GAG GCA GTC TAT TAC ATC GAT CTC TAC TCA CGA   675
211    L   P   R   L   E   A   V   Y   Y   I   D   L   Y   S   R   225

676   GAT GAT TCA AAG GAT AAA GCA ATA TTA CTA AAG TTT GCA AAA CTA   720
226    D   D   S   K   D   K   A   I   L   L   K   F   A   K   L   240

721   GAT TTT TGC ATG CTT CAA GTA ATT CAC CGT AAG GAG TTA AGT ATC   765
241    D   F   C   M   L   Q   V   I   H   R   K   E   L   S   I   255

766   ATC ACA GAG TGG TGG AAA AAT TTA GAT GTT GAA ATA AAT CTC CCA   810
256    I   T   E   W   W   K   N   L   D   V   E   I   N   L   P   270

811   TAT GCT AGA AAC AGA GTT GTA GAA TGC TAT TTT TGG GCA ATG GGA   855
271    Y   A   R   N   R   V   V   E   C   Y   F   W   A   M   G   285

856   GTG TAT TTT GAG CCT CGA TAC TCC TTT GCA AGA AAG ATA TTG TCC   900
286    V   Y   F   E   P   R   Y   S   F   A   R   K   I   L   S   300

901   AAA GTA ATT GCA ATG GCA TCC ATT TTA GAT GAT ACC TAC GAC GCC   945
301    K   V   I   A   M   A   S   I   L   D   D   T   Y   D   A   315

946   TAT GGC ACA CTT GAA GAA CTT GAG CTC TTT ACA AAT GCT ATC AAA   990
316    Y   G   T   L   E   E   L   E   L   F   T   N   A   I   K   330

991   AGG TGG GAT ATT AGC AAC ATA GAT GTA CTT CCG AAG TAC ATG AAA  1035
331    R   W   D   I   S   N   I   D   V   L   P   K   Y   M   K   345

1036  CTG ATT TAT CAA GGA CTC TTG GAT GTT TTT GGT GAA GCT GAG GAG  1080
346    L   I   Y   Q   G   L   L   D   V   F   G   E   A   E   E   360
```

Figure 8(c) continued

```
1081  GAA ATC TCA AAG GAA GGA CAG ACA TAT TGC ATG TCA TAT GTC ATA  1125
 361   E   I   S   K   E   G   Q   T   Y   C   M   S   Y   V   I   375

1126  CAA GCG GTG AAG AAA GTA GTC CAA GCC TAC TTT GAG GAA GCC AAG  1170
 376   Q   A   V   K   K   V   V   Q   A   Y   F   E   E   A   K   390

1171  TGG TGC AGT GAA GGT TAT TTT CCA AAA GTG GAG GAG TAT ATG CAA  1215
 391   W   C   S   E   G   Y   F   P   K   V   E   E   Y   M   Q   405

1216  GTT TCA CTT GTG ACA ACT TGC TAT CAT ATG CTG GCA ACG GCT TCT  1260
 406   V   S   L   V   T   T   C   Y   H   M   L   A   T   A   S   420

1261  TTT CTT GGC ATG GGA AAG ATT GCT GAT AAG CAG GCC TTT GAA TGG  1305
 421   F   L   G   M   G   K   I   A   D   K   Q   A   F   E   W   435

1306  ATC TCC AAT TAC CCT AAA ACT GTG AAA GCC TCC CAA GTT ATT TGC  1350
 436   I   S   N   Y   P   K   T   V   K   A   S   Q   V   I   C   450

1351  AGA CTT ATG GAT GAT ATA GTG TCT CAC GAG TTT GAA CAA AAA AGA  1395
 451   R   L   M   D   D   I   V   S   H   E   F   E   Q   K   R   465

1396  AAG CAT GTT GCC TCG GGT ATT GAA TGT TAC ATG AAG CAG CAT GGC  1440
 466   K   H   V   A   S   G   I   E   C   Y   M   K   Q   H   G   480

1441  GTC TCT GAT GAA GAG GTA ATT AAA GTA TTC CGC AAA CAA ATA TCA  1485
 481   V   S   D   E   E   V   I   K   V   F   R   K   Q   I   S   495

1486  AAT GGA TGG AAA GAT gTA AAT GAA GGA TTC ATG AAG CCA ACA GAA  1530
 496   N   G   W   K   D   V   N   E   G   F   M   K   P   T   E   510

1531  GTG GCA ATG CCT CTC CTT GAG CGC ATT CTC AAT CTT GCA CGA GTG  1575
 511   V   A   M   P   L   L   E   R   I   L   N   L   A   R   V   525

1576  ATA GAT GTT ATT TAC AAG GAT GAT GAT GGC TAC ACC AAC TCT TAT  1620
 526   I   D   V   I   Y   K   D   D   D   G   Y   T   N   S   Y   540

1621  GTG ATC AAA GAC TAC ATC GCC ACA TTG CTT GAG AAG CCT GTt CCC  1665
 541   V   I   K   D   Y   I   A   T   L   L   E   K   P   V   P   555

1666  TTT TGA     1671
 556   F   *
```

Figure 8(d)

GFTpsD1

```
1      ATG TCG TCT GGA GAA ACA TTT CGT CCT ACT GCA GAT TTC CAT CCT    45
1       M   S   S   G   E   T   F   R   P   T   A   D   F   H   P    15

46     AGT TTA TGG AGA AAC CAT TTC CTC AAA GGT GCT TCT GAT TTC AAG    90
16      S   L   W   R   N   H   F   L   K   G   A   S   D   F   K    30

91     ACA GTT GAT CAT ACT GCA ACT CAA GAA CGA CAC GAG GCA CTG AAA   135
31      T   V   D   H   T   A   T   Q   E   R   H   E   A   L   K    45

136    GAA GAG GTA AGG AGA ATG ATA ACA GAT GCT GAA GAT AAG CCT GTT   180
46      E   E   V   R   R   M   I   T   D   A   E   D   K   P   V    60

181    CAG AAG TTA CGC TTG ATT GAT GAA GTA CAA CGC CTG GGG GTG GCT   225
61      Q   K   L   R   L   I   D   E   V   Q   R   L   G   V   A    75

226    TAT CAC TTT GAG AAA GAA ATA GAA GAT GCA ATA CAA AAA TTA TGT   270
76      Y   H   F   E   K   E   I   E   D   A   I   Q   K   L   C    90

271    CCA ATC TAT ATT GAC AGT AAT AGA GCT GAT CTC CAC ACC GTT TCC   315
91      P   I   Y   I   D   S   N   R   A   D   L   H   T   V   S   105

316    CTT CAT TTT CGA TTG CTT AGG CAG CAA GGA ATC AAG ATT TCA TGT   360
106     L   H   F   R   L   L   R   Q   Q   G   I   K   I   S   C   120

361    GAT GTG TTT GAG AAG TTC AAA GAT GAT GAG GGT AGA TTC AAG TCA   405
121     D   V   F   E   K   F   K   D   D   E   G   R   F   K   S   135

406    TCG TTG ATA AAC GAT GTT CAA GGG ATG TTA AGT TTG TAC GAG GCA   450
136     S   L   I   N   D   V   Q   G   M   L   S   L   Y   E   A   150

451    GCA TAC ATG GCA GTT CGC GGA GAA CAT ATA TTA GAT GAA GCC ATT   495
151     A   Y   M   A   V   R   G   E   H   I   L   D   E   A   I   165

496    GCT TTC ACT ACC ACT CAC CTG AAG TCA TTG GTA GCT CAG GAT CAT   540
166     A   F   T   T   T   H   L   K   S   L   V   A   Q   D   H   180

541    GTA ACC CCT AAG CTT GCG GAA CAG ATA AAT CAT GCT TTA TAC CGT   585
181     V   T   P   K   L   A   E   Q   I   N   H   A   L   Y   R   195

586    CCT CTT CGT AAA ACC CTA CCA AGA TTA GAG GCG AGG TAT TTT ATG   630
196     P   L   R   K   T   L   P   R   L   E   A   R   Y   F   M   210

631    TCC ATG ATC AAT TCA ACA AGT GAT CAT TTA TAC AAT AAA ACT CTG   675
211     S   M   I   N   S   T   S   D   H   L   Y   N   K   T   L   225

676    CTG AAT TTT GCA AAG TTA GAT TTT AAC ATA TTG CTA GAG CTG CAC   720
226     L   N   F   A   K   L   D   F   N   I   L   L   E   L   H   240

721    AAG GAG GAA CTC AAT GAA TTA ACA AAG TGG TGG AAA GAT TTA GAC   765
241     K   E   E   L   N   E   L   T   K   W   W   K   D   L   D   255

766    TTC ACT ACA AAA CTA CCT TAT GCA AGA GAC AGA TTA GTG GAG TTA   810
256     F   T   T   K   L   P   Y   A   R   D   R   L   V   E   L   270

811    TAT TTT TGG GAT TTA GGG ACA TAC TTC GAG CCT CAA TAT GCA TTT   855
271     Y   F   W   D   L   G   T   Y   F   E   P   Q   Y   A   F   285

856    GGG AGA AAG ATA ATG ACC CAA TTA AAT TAC ATA TTA TCC ATC ATA   900
286     G   R   K   I   M   T   Q   L   N   Y   I   L   S   I   I   300

901    GAT GAT ACT TAT GAT GCG TAT GGT ACA CTT GAA GAA CTC AGC CTC   945
301     D   D   T   Y   D   A   Y   G   T   L   E   E   L   S   L   315
```

Figure 8(d) continued

```
946    TTT ACT GAA GCA GTT CAA AGA TGG AAT ATT GAG GCC GTA GAT ATG    990
316     F   T   E   A   V   Q   R   W   N   I   E   A   V   D   M    330

991    CTT CCA GAA TAC ATG AAA TTG ATT TAC AGG ACA CTC TTA GAT GCT    1035
331     L   P   E   Y   M   K   L   I   Y   R   T   L   L   D   A    345

1036   TTT AAT GAA ATT GAG GAA GAT ATG GCC AAG CAA GGA AGA TCA CAC    1080
346     F   N   E   I   E   E   D   M   A   K   Q   G   R   S   H    360

1081   TGC GTA CGT TAT GCA AAA GAG GAG AAT CAA AAA GTA ATT GGA GCA    1125
361     C   V   R   Y   A   K   E   E   N   Q   K   V   I   G   A    375

1126   TAC TCT GTT CAA GCC AAA TGG TTC AGT GAA GGT TAC GTT CCA ACA    1170
376     Y   S   V   Q   A   K   W   F   S   E   G   Y   V   P   T    390

1171   ATT GAG GAG TAT ATG CCT ATT GCA CTA ACA AGT TGT GCT TAC ACA    1215
391     I   E   E   Y   M   P   I   A   L   T   S   C   A   Y   T    405

1216   TTC GTC ATA ACA AAT TCC TTC CTT GGC ATG GGT GAT TTT GCA ACT    1260
406     F   V   I   T   N   S   F   L   G   M   G   D   F   A   T    420

1261   AAA GAG GTT TTT GAA TGG ATC TCC AAT AAC CCT AAG GTT GTA AAA    1305
421     K   E   V   F   E   W   I   S   N   N   P   K   V   V   K    435

1306   GCA GCA TCA GTT ATC TGC AGA CTC ATG GAT GAC ATG CAA GGT CAT    1350
436     A   A   S   V   I   C   R   L   M   D   D   M   Q   G   H    450

1351   GAG TTT GAG CAG AAG AGA GGA CAT GTT GCG TCA GCT ATT GAA TGT    1395
451     E   F   E   Q   K   R   G   H   V   A   S   A   I   E   C    465

1396   TAC ACG AAG CAG CAT GGT GTC TCT AAG GAA GAG GCA ATT AAA ATG    1440
466     Y   T   K   Q   H   G   V   S   K   E   E   A   I   K   M    480

1441   TTT GAA GAA GAA GTT GCA AAT GCA TGG AAA GAT ATT AAC GAG GAG    1485
481     F   E   E   E   V   A   N   A   W   K   D   I   N   E   E    495

1486   TTG ATG ATG AAG CCA ACC GTC GTT GCC CGA CCA CTG CTC GGG ACG    1530
496     L   M   M   K   P   T   V   V   A   R   P   L   L   G   T    510

1531   ATT CTT AAT CTT GCT CGT GCA ATT GAT TTT ATT TAC AAA GAG GAC    1575
511     I   L   N   L   A   R   A   I   D   F   I   Y   K   E   D    525

1576   GAC GGC TAT ACG CAT TCT TAC CTA ATT AAA GAT CAA ATT GCT TCT    1620
526     D   G   Y   T   H   S   Y   L   I   K   D   Q   I   A   S    540

1621   GTG CTA GGA GAC CAC GTT CCA TTT TGA   1647
541     V   L   G   D   H   V   P   F   *
```

Figure 8(e)

GFTpsD2

```
1     ATG TCG TCT GGA GAA ACA TTT CGT CCT ACT GCA GAT TTC CAT CCT   45
1      M   S   S   G   E   T   F   R   P   T   A   D   F   H   P   15

46    AGT TTA TGG AGA AAC CAT TTC CTC AAA GGT GCT TCT GAT TTC AAG   90
16     S   L   W   R   N   H   F   L   K   G   A   S   D   F   K   30

91    ACA GTT GAT CAT ACT GCA ACT CAA GAA CGA CAC GAG GCA CTG AAA   135
31     T   V   D   H   T   A   T   Q   E   R   H   E   A   L   K   45

136   GAA GAG GTA AGG AGA ATG ATA ACA GAT GCT GAA GAT AAG CCT GTT   180
46     E   E   V   R   R   M   I   T   D   A   E   D   K   P   V   60

181   CAG AAG TTA CGC TTG ATT GAT GAA GTA CAA CGC CTG GGG GTG GCT   225
61     Q   K   L   R   L   I   D   E   V   Q   R   L   G   V   A   75

226   TAT CAC TTT GAG AAA GAA ATA GAA GAT GCA ATA CAA AAA TTA TGT   270
76     Y   H   F   E   K   E   I   E   D   A   I   Q   K   L   C   90

271   CCA AAC TAT ATT CAC AGT AAT AGC CCT GAT CTT CAC ACC GTT TCT   315
91     P   N   Y   I   H   S   N   S   P   D   L   H   T   V   S   105

316   CTT CAT TTT CGA TTG CTT AGG CAG CAA GGA ATC AAG ATT TCA TGT   360
106    L   H   F   R   L   L   R   Q   Q   G   I   K   I   S   C   120

361   GAT GTG TTT GAG AAG TTC AAA GAT GAT GAG GGT AGA TTC AAG TCA   405
121    D   V   F   E   K   F   K   D   D   E   G   R   F   K   S   135

406   TCG TTG ATA AAC GAT GTT CAA GGG ATG TTA AGT TTG TAC GAG GCA   450
136    S   L   I   N   D   V   Q   G   M   L   S   L   Y   E   A   150

451   GCA TAC ATG GCA GTT CGC GGA GAA CAT ATA TTA GAT GAA GCC ATT   495
151    A   Y   M   A   V   R   G   E   H   I   L   D   E   A   I   165

496   GCT TTC ACT ACC ACT CAC CTG AAG TCA TTG GTA GCT CAG GAT CAT   540
166    A   F   T   T   T   H   L   K   S   L   V   A   Q   D   H   180

541   GTA ACC CCT AAG CTT GCG GAA CAG ATA AAT CAT GCT TTA TAC CGT   585
181    V   T   P   K   L   A   E   Q   I   N   H   A   L   Y   R   195

586   CCT CTT CGT AAA ACC CTA CCA AGA TTA GAG GCG AGG TAT TTT ATG   630
196    P   L   R   K   T   L   P   R   L   E   A   R   Y   F   M   210

631   TCC ATG ATC AAT TCA ACA AGT GAT CAT TTA TAC AAT AAA ACT CTG   675
211    S   M   I   N   S   T   S   D   H   L   Y   N   K   T   L   225

676   CTG AAT TTT GCA AAG TTA GAT TTT AAC ATA TTG CTA GAG CTG CAC   720
226    L   N   F   A   K   L   D   F   N   I   L   L   E   L   H   240

721   AAG GAG GAA CTC AAT GAA TTA ACA AAG TGG TGG AAA GAT TTA GAC   765
241    K   E   E   L   N   E   L   T   K   W   W   K   D   L   D   255

766   TTC ACT ACA AAA CTA CCT TAT GCA AGA GAC AGA TTA GTG GAG TTA   810
256    F   T   T   K   L   P   Y   A   R   D   R   L   V   E   L   270

811   TAT TTT TGG GAT TTA GGG ACA TAC TTC GAG CCT CAA TAT GCA TTT   855
271    Y   F   W   D   L   G   T   Y   F   E   P   Q   Y   A   F   285

856   GGG AGA AAG ATA ATG ACC CAA TTA AAT TAC ATA TTA TCC ATC ATA   900
286    G   R   K   I   M   T   Q   L   N   Y   I   L   S   I   I   300

901   GAT GAT ACT TAT GAT GCG TAT GGT ACA CTT GAA GAA CTC AGC CTC   945
301    D   D   T   Y   D   A   Y   G   T   L   E   E   L   S   L   315
```

Figure 8(e) continued

```
946   TTT ACT GAA GCA GTT CAA AGA TGG AAT ATT GAG GCC GTA GAT ATG   990
316    F   T   E   A   V   Q   R   W   N   I   E   A   V   D   M    330

991   CTT CCA GAA TAC ATG AAA TTG ATT TAC AGG ACA CTC TTA GAT GCT   1035
331    L   P   E   Y   M   K   L   I   Y   R   T   L   L   D   A    345

1036  TTT AAT GAA ATT GAG GAA GAT ATG GCC AAG CAA GGA AGA TCA CAC   1080
346    F   N   E   I   E   E   D   M   A   K   Q   G   R   S   H    360

1081  TGC GTA CGT TAT GCA AAA GAG GAG AAT CAA AAA GTA ATT GGA GCA   1125
361    C   V   R   Y   A   K   E   E   N   Q   K   V   I   G   A    375

1126  TAC TCT GTT CAA GCC AAA TGG TTC AGT GAA GGT TAC GTT CCA ACA   1170
376    Y   S   V   Q   A   K   W   F   S   E   G   Y   V   P   T    390

1171  ATT GAG GAG TAT ATG CCT ATT GCA CTA ACA AGT TGT GCT TAC ACA   1215
391    I   E   E   Y   M   P   I   A   L   T   S   C   A   Y   T    405

1216  TTC GTC ATA ACA AAT TCC TTC CTT GGC ATG GGT GAT TTT GCA ACT   1260
406    F   V   I   T   N   S   F   L   G   M   G   D   F   A   T    420

1261  AAA GAG GTT TTT GAA TGG ATC TCC AAT AAC CCT AAG GTT GTA AAA   1305
421    K   E   V   F   E   W   I   S   N   N   P   K   V   V   K    435

1306  GCA GCA TCA GTT ATC TGC AGA CTC ATG GAT GAC ATG CAA GGT CAT   1350
436    A   A   S   V   I   C   R   L   M   D   D   M   Q   G   H    450

1351  GAG TTT GAG CAG AAG AGA GGA CAT GTT GCG TCA GCT ATT GAA TGT   1395
451    E   F   E   Q   K   R   G   H   V   A   S   A   I   E   C    465

1396  TAC ACG AAG CAG CAT GGT GTC TCT AAG GAA GAG GCA ATT AAA ATG   1440
466    Y   T   K   Q   H   G   V   S   K   E   E   A   I   K   M    480

1441  TTT GAA GAA GAA GTT GCA AAT GCA TGG AAA GAT ATT AAC GAG GAG   1485
481    F   E   E   E   V   A   N   A   W   K   D   I   N   E   E    495

1486  TTG ATG ATG AAG CCA ACC GTC GTT GCC CGA CCA CTG CTC GGG ACG   1530
496    L   M   M   K   P   T   V   V   A   R   P   L   L   G   T    510

1531  ATT CTT AAT CTT GCT CGT GCA ATT GAT TTT ATT TAC AAA GAG GAC   1575
511    I   L   N   L   A   R   A   I   D   F   I   Y   K   E   D    525

1576  GAC GGC TAT ACG CAT TCT TAC CTA ATT AAA GAT CAA ATT GCT TCT   1620
526    D   G   Y   T   H   S   Y   L   I   K   D   Q   I   A   S    540

1621  GTG CTA GGA GAC CAC GTT CCA TTT TGA   1647
541    V   L   G   D   H   V   P   F   *
```

Figure 8(f)

```
GFTpsE

1    ATG TCT TTG GAA GTT TCA GCC TCT CCT GCT AAA GTT ATC CAA AAT    45
1     M   S   L   E   V   S   A   S   P   A   K   V   I   Q   N    15

46   GCT GGG AAA GAT TCT ACT CGT CGC TCT GCA AAT TAT CAT CCA AGC    90
16    A   G   K   D   S   T   R   R   S   A   N   Y   H   P   S    30

91   ATC TGG GGG GAT CAT TTC CTT CAA TAT ACT TGT GAC ACC CAG GAA   135
31    I   W   G   D   H   F   L   Q   Y   T   C   D   T   Q   E    45

136  ACT GAT GAT GGC AGC AAT GTA AAG CAT CTA GAG CTG AAG AAA GAA   180
46    T   D   D   G   S   N   V   K   H   L   E   L   K   K   E    60

181  ATT AGA AGA ATG CTA AAA GCT GAT AAC AAG CCT TCA CGT ACA CTT   225
61    I   R   R   M   L   K   A   D   N   K   P   S   R   T   L    75

226  CAA TTG ATT GAT GCA ATT CAG CGT TTA GGA GTG TCT TAC CAT TTT   270
76    Q   L   I   D   A   I   Q   R   L   G   V   S   Y   H   F    90

271  GAA AGT GAG ATT GAT GAA ATA TTG GGA AAG ATG CAT AAG GCT TCC   315
91    E   S   E   I   D   E   I   L   G   K   M   H   K   A   S   105

316  CAA GAC TCT GAT CTT TGT GAT AAT GAA AAT GAT GAG CTC TAT TAT   360
106   Q   D   S   D   L   C   D   N   E   N   D   E   L   Y   Y   120

361  ATC TCT CTT CAT TTT CGA TTA CTT AGA CAA AAT GGC TAT AAA ATT   405
121   I   S   L   H   F   R   L   L   R   Q   N   G   Y   K   I   135

406  TCC GCT GAT GTG TTC AAA AAG TTC AAA GAC ACG GAT GGG AAC TTT   450
136   S   A   D   V   F   K   K   F   K   D   T   D   G   N   F   150

451  AAA ACA TCT CTT GCG AAA GAT GTT CGA GGA ATG TTA AGC TTG TAT   495
151   K   T   S   L   A   K   D   V   R   G   M   L   S   L   Y   165

496  GAA GCT ACG CAT CTC GGG GTA CAT GAA GAA GAT ATA CTA GAT GAA   540
166   E   A   T   H   L   G   V   H   E   E   D   I   L   D   E   180

541  GCG CTT GCT TTC ACC ACT AGT CAC CTA GAG TCA ATA GCG ACT CAT   585
181   A   L   A   F   T   T   S   H   L   E   S   I   A   T   H   195

586  CAA ATC AGG TCT CCA CTT GTT GAA CAA GTC AAA CAT GCC TTA GTT   630
196   Q   I   R   S   P   L   V   E   Q   V   K   H   A   L   V   210

631  CAG CCT ATC CAC AGG GGC TTC CAA AGG CTT GAG GCA AGA CAG TAC   675
211   Q   P   I   H   R   G   F   Q   R   L   E   A   R   Q   Y   225

676  ATT CCT ATC TAT CAA GAA GAA TCT CCC CAC AAT GAA GCT CTG TTA   720
226   I   P   I   Y   Q   E   E   S   P   H   N   E   A   L   L   240

721  ACT TTT GCA AAG TTA GAT TTT AAC AAA TTG CAA AAG CCT CAC CAG   765
241   T   F   A   K   L   D   F   N   K   L   Q   K   P   H   Q   255

766  AAG GAA CTC GGT GAT ATT TCA AGG TGG TGG AAA GAA TTA GAC TTT   810
256   K   E   L   G   D   I   S   R   W   W   K   E   L   D   F   270

811  GCA CAT AAG CTA CCT TTC ATA AGA GAT AGA GTT GCG GAG TGC TAC   855
271   A   H   K   L   P   F   I   R   D   R   V   A   E   C   Y   285

856  TTT TGG ATA TTA GGA GTG TAT TTC GAG CCC CAA TAT TCA TTT GCA   900
286   F   W   I   L   G   V   Y   F   E   P   Q   Y   S   F   A   300

901  AGA AGA ATA TTG ACG AAA GTG ATC TCC ATG ACT TCT GTT ATT GAT   945
301   R   R   I   L   T   K   V   I   S   M   T   S   V   I   D   315
```

Figure 8(f) continued

```
946   GAT ATC TAT GAT GTG TAT GGC AAA ATT GAA GAA CTT GAG CTT TTT   990
316    D   I   Y   D   V   Y   G   K   I   E   E   L   E   L   F    330

991   ACT TCA GCT ATT GAG AGG TGG GAT ATC AGT GCC ATA GAT CAA CTT  1035
331    T   S   A   I   E   R   W   D   I   S   A   I   D   Q   L    345

1036  CCT GAG TAT ATG AAA TTG TGT TAT AGG GCC CTT CTT GAT GTT TTT  1080
346    P   E   Y   M   K   L   C   Y   R   A   L   L   D   V   F    360

1081  AGT GAA GCA GAG AAG GAT TTG GCC CCC CAA GGA AAA TCA TAC CGC  1125
361    S   E   A   E   K   D   L   A   P   Q   G   K   S   Y   R    375

1126  CTC TAT TAT GCA AAA GAA GCG ATG AAG AAT ATG GTT AAG AAT TAC  1170
376    L   Y   Y   A   K   E   A   M   K   N   M   V   K   N   Y    390

1171  TTC TAC GAA GCT AAA TGG TGT CTT CAG AAT TAT GTA CCT ACA GTG  1215
391    F   Y   E   A   K   W   C   L   Q   N   Y   V   P   T   V    405

1216  GAT GAG TAC ATG ACG GTT GCA TTA GTT ACA TCT GGC TCC CCA ATG  1260
406    D   E   Y   M   T   V   A   L   V   T   S   G   S   P   M    420

1261  TTG TCA ACC ACA TCC TTT GTT GGC ATG GGA GAC ATT GTA ACT AAA  1305
421    L   S   T   T   S   F   V   G   M   G   D   I   V   T   K    435

1306  GAA TCT TTT GAG TGG TTA TTC AGC AAT CCT AGA TTT ATT AGG GCT  1350
436    E   S   F   E   W   L   F   S   N   P   R   F   I   R   A    450

1351  TCT TCT ATA GTT TGC CGA CTC ATG GAT GAC ATA GTG TCA CAC AAG  1395
451    S   S   I   V   C   R   L   M   D   D   I   V   S   H   K    465

1396  TTT GAA CAA AGC AGA GGG CAC GTT GCC TCA AGC GTT GAG TGT TAC  1440
466    F   E   Q   S   R   G   H   V   A   S   S   V   E   C   Y    480

1441  ATG AAA CAA CAT GGA GCA ACA GAA GAG GAA GCA TGC AAT GAG TTT  1485
481    M   K   Q   H   G   A   T   E   E   E   A   C   N   E   F    495

1486  CGG AAA CAA GTT TCA AAT GCC TGG AAG GAT ATA AAT GAG GAC TGC  1530
496    R   K   Q   V   S   N   A   W   K   D   I   N   E   D   C    510

1531  CTA CGC CCA ACG GTT GTG CCA ATG CCA CTT CTG ATG CGA ATT CTC  1575
511    L   R   P   T   V   V   P   M   P   L   L   M   R   I   L    525

1576  AAT CTT ACA CGC GTT ATA GAT GTC ATT TAC AAG TAT GAA GAT GGC  1620
526    N   L   T   R   V   I   D   V   I   Y   K   Y   E   D   G    540

1621  TAC ACT CAT TCC GCA GTT GTG CTG AAA GAT TTT GTT GCT TCT TTG  1665
541    Y   T   H   S   A   V   V   L   K   D   F   V   A   S   L    555

1666  TTT ATT AAT CCT GTG CCG ATA TGA   1689
556    F   I   N   P   V   P   I   *
```

SESQUITERPENE SYNTHASES AND METHODS OF USE

CROSS-REFERENCE TO RELATED APPLICATIONS

This application is a continuation of International Application PCT/IB/2003/005072, filed on Oct. 2, 2003 and claims the benefit of U.S. Provisional Application No. 60/415,765, filed Oct. 4, 2002, the contents of each of which are incorporated by reference herein. This application also claims the benefit of priority of International Application, PCT/IB02/05070, filed Dec. 2, 2002, the contents of which are incorporated by reference herein.

TECHNICAL FIELD

The present invention relates to sesquiterpene synthases and methods of their production and use. In one embodiment, the invention provides nucleic acids comprising a nucleotide sequence as described herein that encodes for at least one sesquiterpene synthase. In a further embodiment, the invention also provides for sesquiterpene synthases and methods of making and using these enzymes. For example, sesquiterpene synthases of the invention may be used to convert farnesyl-pyrophosphate to various oxygenated and aliphatic sesquiterpenes including valencene, bicyclo-germacrene, cubebol and delta-cadine.

BACKGROUND OF THE INVENTION

Terpene compounds represent a wide range of natural molecules with a large diversity of structure. The plant kingdom contains the highest diversity of monoterpenes and sesquiterpenes. Often they play a role in defense of the plants against pathogens, insects and herbivored and for attraction of pollinating insect.

The biosynthesis of terpenes has been extensively studied in many organisms. The common precursor to terpenes is isopentenyl pyrophosphate (IPP) and many of the enzymes catalyzing the steps leading to IPP have been characterized. Two distinct pathways for IPP biosynthesis are currently known (FIG. 1). The mevalonate pathway is found in the plants cytosol and in yeast and the non-mevalonate pathway (or deoxyxylulose-5-phosphate (DXP) pathway is found in the plant plastids and in *E. coli*.

For example, the IPP is isomerized to dimethylallyl diphosphate by the IPP isomerase and these two C5 compounds can be condensed by prenyl transferases to form the acyclic pyrophosphate terpene precursors for each class of terpenes, i.e. geranyl-pyrophosphate (GPP) for the monoterpenes, farnesyl-pyrophosphate (FPP) for the sesquiterpenes, geranylgeranyl-pyrophosphate (GGPP) for the diterpenes (FIG. 2). The enzymes catalyzing the cyclisation step of the acyclic precursors are named terpene cyclases or terpene synthases, which are referred to as terpene synthases herein.

These enzymes may be able to catalyze complex multiple step cyclization to form the carbon skeleton of a terpene or sesquiterpene compound. For example, the initial step of the catalyzed cyclisation may be the ionization of the diphosphate group to form a allylic cation. The substrate then undergoes isomerizations and rearrangements which can be controlled by the enzyme active site. The product may, for example, be acyclic, mono-, di or tri-cyclic. A proton may then be released from the carbocation or the carbocation reacts with a water molecule and the terpene hydrocarbon or alcohol is released. Some terpene synthases produce a single product, but many produce multiple products.

A large diversity of terpene structures and sesquiterpene synthases are found in nature. Several sesquiterpene synthase encoding cDNA or genes have been cloned and characterized from different plant sources, e.g, 5-epi-aristolochene synthases form *Nicotiana tabacum* (Facchini, P. J. and Chappell, J. (1992) Proc. Natl. Acad. Sci. U.S.A. 89, 11088-11092.) and from *Capsicum annum* (Back, K., et al. (1998) Plant Cell Physiol. 39 (9), 899-904.), a vetispiradiene synthase from *Hyoscyamus muticus* (Back, K. and Chappell, J. (1995) J. Biol. Chem. 270 (13), 7375-7381.), a (E)-β-farnesene synthase from *Mentha piperita* (Crock, J., et al. (1997) Proc. Natl. Acad. Sci. U.S.A. 94 (24), 12833-12838.), a δ-selinene synthase and a γ-humulene synthase from *Abies grandis* (Steele, C. L., et al. (1998) J. Biol. Chem. 273 (4), 2078-2089.), δ-cadinene synthases from *Gossypium arboreum* (Chen, X. Y., et al. (1995) Arch. Biochem. Biophys. 324 (2), 255-266; Chen, X. Y., et al. (1996) J. Nat Prod. 59, 944-951.), a E-α-bisabolene synthase from *Abies grandis* (Bohlmann, J., et al. (1998) Proc. Natl. Acad. Sci. U.S.A. 95 (12), 6756-6761.), a germacrene C synthase from *Lycopersicon esculentum* (Colby, S. M., et al. (1998) Proc. Natl. Acad. Sci. U.S.A. 95 (5), 2216-2221.), an epi-cedrol synthase and an amorpha-4,11-diene synthase from *Artemisia annua* (Mercke, P., et al. (1999) Arch. Biochem. Biophys. 369 (2), 213-222; Mercke, P., et al. (2000) Arch. Biochem. Biophys. 381 (2), 173-180.), and germacrene A synthases from *Lactuca sativa*, from *Cichorium intybus* and from *Solidago canadensis* (Bennett, M. H., et al. (2002) Phytochem. 60, 255-261; Bouwmeester, H. J., et al. (2002) Plant Physiol. 129 (1), 134-144; Prosser I, et al. (2002) Phytochem. 60, 691-702).

Many sesquiterpene compounds are used in perfumery (e.g. patchoulol, nootkatone, santalol, vetivone, sinensal) and many are extracted from plants. As a result, their availability and prices may be subject to fluctuation related to the availability of the plants and the stability of the producing countries. The availability of a plant-independent system for production of sesquiterpenes may therefore be of interest. Due to the structural complexity of some sesquiterpenes, their chemical synthesis at an acceptable cost may not always be feasible.

SUMMARY OF THE INVENTION

In one embodiment, the invention relates to isolated nucleic acids that encode sesquiterpene synthases. As used herein, a sesquiterpene synthase may also be referred to by at least one compound produced by the enzyme upon contact with an acyclic pyrophosphate terpene precursor such as farnesyl-pyrophosphate. For example, a sesquiterpene synthase capable of producing bicylogermacrene as one of its products may be referred to as bicylogermacrene synthase. Using this convention, examples of nucleic acids of the invention include cDNAs encoding cubebol synthase (GFTpsC) (SEQ ID NO:1); δ-cadine synthase (GFTpsE) (SEQ ID NO:2); bicylogermacrene synthase (GFTpsB) (SEQ ID NO:3); and valencene synthase (GFTpsD1 & GFTpsD2) (SEQ ID NO:4 & SEQ ID NO:5).

In one embodiment, the invention provides an isolated nucleic acid selected from: (a) a nucleic acid comprising the nucleotide sequence substantially as set out in SEQ ID NO:6, SEQ ID NO:7, SEQ ID NO:8, SEQ ID NO:9, or SEQ ID NO:10; (b) a nucleic acid encoding the polypeptide substantially set out in SEQ ID NO:1, SEQ ID NO:2, SEQ ID NO:3, SEQ ID NO:4, or SEQ ID NO:5; and (c) a nucleic acid that hybridizes to the nucleic acid of (a) or (b) under low stringency conditions, wherein the polypetide encoded by said nucleic acid is a sesquiterpene synthase. Preferably, the invention provides an isolated nucleic acid selected from: (a) a nucleic acid comprising the nucleotide sequence substantially as set out in SEQ ID NO:6 or SEQ ID NO:7; (b) a nucleic acid encoding the polypeptide substantially set out in SEQ ID NO:1 or SEQ ID NO:2; and (c) a nucleic acid that hybridizes to the nucleic acid of (a) or (b) under low stringency conditions, wherein the polypetide encoded by said nucleic acid is a sesquiterpene synthase. In one embodiment, the defined conditions are moderate stringency conditions and in a further embodiment high stringency conditions. Other embodiments include: a polypeptide encoded by a nucleic acid of the invention; a host cell comprising a nucleic acid of the invention; a non-human organism modified to harbor a nucleic acid of the invention; and methods of producing a polypeptide comprising culturing host cells of the invention.

In another embodiment, the invention provides an isolated polypeptide comprising an amino acid sequence substantially as set out in SEQ ID NO:1, SEQ ID NO:2, SEQ ID NO:3, SEQ ID NO:4, or SEQ ID NO:5. Preferably, the invention provides an isolated polypeptide comprising an amino acid sequence substantially as set out in SEQ ID NO:1 or SEQ ID NO:2.

In a further embodiment, the invention provides a vector comprising at least one nucleic acid chosen from (a) a nucleic acid comprising the nucleotide sequence substantially as set out in SEQ ID NO:6, SEQ ID NO:7, SEQ ID NO:8, SEQ ID NO:9, or SEQ ID NO:10; (b) a nucleic acid encoding the polypeptide substantially set out in SEQ ID NO:1, SEQ ID NO:2, SEQ ID NO:3, SEQ ID NO:4, or SEQ ID NO:5; and (c) a nucleic acid that hybridizes to the nucleic acid of (a) or (b) under low stringency conditions, wherein the polypeptide encoded by said nucleic acid is a sesquiterpene synthase. Other embodiments include, methods of making a recombinant host cell comprising introducing a vector of the invention into a host cell.

In one embodiment, the invention provides a method of making at least one sesquiterpene synthase comprising culturing a host modified to contain at least one nucleic acid sequence under conditions conducive to the production of said at least one sesquiterpene synthase. In one embodiment, the at least one nucleic acid is chosen from (a) a nucleic acid comprising the nucleotide sequence substantially as set out in SEQ ID NO:6, SEQ ID NO:7, SEQ ID NO:8, SEQ ID NO:9, or SEQ ID NO:10; (b) a nucleic acid encoding the polypeptide substantially set out in SEQ ID NO:1, SEQ ID NO:2, SEQ ID NO:3, SEQ ID NO:4, or SEQ ID NO:5; and (c) a nucleic acid that hybridizes to the nucleic acid of (a) or (b) under low stringency conditions, wherein the polypetide encoded by said nucleic acid is a sesquiterpene synthase. The host may be chosen from, for example, plants, microorganisms, bacterial cells, yeast cells, plant cells, and animal cells.

In another embodiment the invention provides a method of making at least one terpenoid comprising 1) contacting at least one acyclic pyrophosphate terpene precursor with at least one polypeptide encoded by a nucleic acid. In one embodiment, the nucleic acid is chosen from (a) a nucleic acid comprising the nucleotide sequence substantially as set out in SEQ ID NO:6, SEQ ID NO:7, SEQ ID NO:8, SEQ ID NO:9, or SEQ ID NO:10; (b) a nucleic acid encoding the polypeptide substantially set out in SEQ ID NO:1, SEQ ID NO:2, SEQ ID NO:3, SEQ ID NO:4, or SEQ ID NO:5; and (c) a nucleic acid that hybridizes to the nucleic acid of (a) or (b) under low stringency conditions, wherein the polypetide encoded by said nucleic acid is a sesquiterpene synthase, 2) isolating at least one terpenoid produced in (1). In one embodiment, the at least one terpenoid is chosen from sesquiterpenes. In a further embodiment, the at least one acyclic pyrophosphate terpene precursor is farnesyl-pyrophosphate. The sesquiterpenes produced by the methods of the invention include, but are not limited to, bicylogermacrene, cubebol, valencene, α-cubebene, germacrene D, and δ-cadinene (FIG. 3).

It is to be understood that both the foregoing general description and the following detailed description are exemplary and explanatory only and are not restrictive of the invention as claimed. Reference will now be made in detail to exemplary embodiments of the present invention.

BRIEF DESCRIPTION OF THE FIGURES

FIG. 5: Alignment of the amino acid sequences deduced from the amplification products obtained by RT-PCR on grapefruit total RNA (GFTpsA (SEQ ID NO:29); GFTpsB (SEQ ID NO:30); and GFTpsC (SEQ ID NO:31)).

FIG. 8: The amino acid and nucleotide sequences of (a) GFTpsA (SEQ ID NO:32 and SEQ ID NO:33), (b) GFTpsB (SEQ ID NO:3 and SEQ ID NO:8), (c) GFTbsC (SEQ ID NO:1 and SEQ ID NO:6), (d) GFTpsD1 (SEQ ID NO:4 and SEQ ID NO:9), (e) GFTpsD2 (SEQ ID NO:5 and SEQ ID NO:10), and (f) GFTpsE (SEQ ID NO:2 and SEQ ID NO:7).

DETAILED DESCRIPTION OF THE PREFERRED EMBODIMENTS

Figure 1:
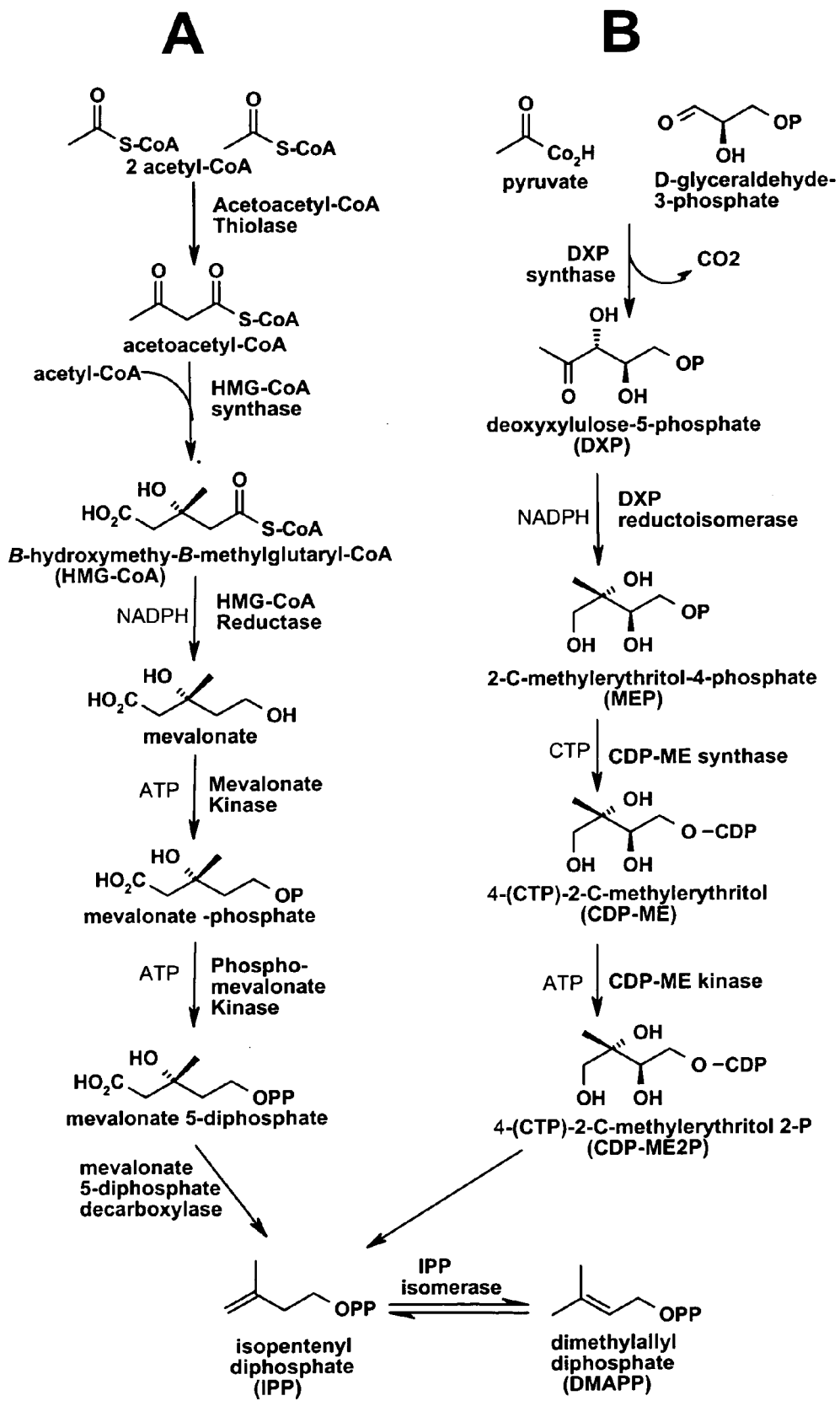
FIG. 1: Example pathways for biosynthesis of isopentenyl pyrophosphate (Mevalonate pathway (A) and deoxyxylulose pathway (B)).

A terpene is an unsaturated hydrocarbon based on an isoprene unit (C5H8) which may be acyclic or cyclic. Terpene derivatives, include but are not limited to camphor, menthol, terpineol, and borneol, geraniol. Terpenes or Terpenoid, as used herein includes terpenes and terpene derivatives, including compounds that have undergone one or more steps of functionalization such as hydroxylations, isomerizations, oxido-reductions or acylations. As used herein, a sesquiterpene is terpene based on a C15 structure and includes sesquiterpenes and sesquiterpenes derivatives, including compounds that have undergone one or more steps of functionalization such as hydroxylations, isomerizations, oxido-reductions or acylations.

As used herein, a derivative is any compound obtained from a known or hypothetical compound and containing essential elements of the parent substance.

As used herein, sesquiterpene synthase is any enzyme that catalyzes the synthesis of a sesquiterpene.

The phrase "identical," "substantially identical," or "substantially as set out," means that a relevant sequence is at least 70%, 75%, 80%, 85%, 90%, 92%, 95%, 96%, 97%, 98%, or 99% identical to a given sequence. By way of example, such sequences may be allelic variants, sequences derived from various species, or they may be derived from the given sequence by truncation, deletion, amino acid substitution or addition. For polypeptides, the length of comparison sequences will generally be at least 20, 30, 50, 100 or more amino acids. For nucleic acids, the length of comparison sequences will generally be at least 50, 100, 150, 300, or more nucleotides. Percent identity between two sequences is determined by standard alignment algorithms such as, for example, Basic Local Alignment Tool (BLAST) described in Altschul et al. (1990) J. Mol. Biol., 215:403-410, the algorithm of Needleman et al. (1970) J. Mol. Biol., 48:444-453, or the algorithm of Meyers et al. (1988) Comput. Appl. Biosci., 4:11-17.

The invention thus provides, in one embodiment, an isolated nucleic acid selected from: (a) a nucleic acid comprising the nucleotide sequence sequence substantially as set out in SEQ ID NO:6, SEQ ID NO:7, SEQ ID NO:8, SEQ ID NO:9, or SEQ ID NO:10; (b) a nucleic acid encoding the polypeptide substantially set out in SEQ ID NO:1, SEQ ID NO:2, SEQ ID NO:3, SEQ ID NO:4, or SEQ ID NO:5; and (c) a nucleic acid that hybridizes to the nucleic acid of (a) or (b) under low stringency conditions, wherein the polypetide encoded by said nucleic acid is a sesquiterpene synthase. In one embodiment, the defined conditions are moderate stringency conditions and in a further embodiment high stringency conditions.

As used herein, one determines whether a polypeptide encoded by a nucleic acid of the invention is a sesquiterpene synthase by the enzyme characterization assay described in the examples herein.

As used herein, the term hybridization or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85-90% identical, remain bound to each other. Definitions of low stringency, moderate, and high stringency hybridization conditions are provided herein.

Appropriate hybridization conditions can be selected by those skilled in the art with minimal experimentation as exemplified in Ausubel et al. (1995), Current Protocols in Molecular Biology, John Wiley & Sons, sections 2, 4, and 6. Additionally, stringency conditions are described in Sambrook et al. (1989) Molecular Cloning: A Laboratory Manual, 2nd ed., Cold Spring Harbor Press, chapters 7, 9, and 11. As used herein, defined conditions of low stringency are as follows. Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ 32P-labeled probe is used. Filters are incubated in hybridization mixture for 18-20 h at 40° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of moderate stringency are as follows. Filters containing DNA are pretreated for 7 h at 50° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ 32P-labeled probe is used. Filters are incubated in hybridization mixture for 30 h at 50° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in the prehybridization mixture containing 100 µg/ml denatured salmon sperm DNA and 5-20×10$^6$ cpm of 32P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 minutes.

Other conditions of low, moderate, and high stringency well known in the art (e.g., as employed for cross-species hybridizations) may be used if the above conditions are inappropriate (e.g., as employed for cross-species hybridizations).

In one embodiment, a nucleic acid and/or polypeptide of the invention is isolated from a citrus, such as, for example a grapefruit or an orange. In a particular embodiment, the invention relates to certain isolated nucleotide sequences including those that are substantially free from contaminating endogenous material. The terms "nucleic acid" or "nucleic acid molecule" refer to a deoxyribonucleotide or ribonucleotide polymer in either single-or double-stranded form, and unless otherwise limited, would encompass known analogs of natural nucleotides that can function in a similar manner as naturally occurring nucleotides. A "nucleotide sequence" also refers to a polynucleotide molecule or oligonucleotide molecule in the form of a separate fragment or as a component of a larger nucleic acid. The nucleotide sequence or molecule may also be referred to as a "nucleotide probe." Some of the nucleic acid molecules of the invention are derived from DNA or RNA isolated at least once in substantially pure form and in a quantity or concentration enabling identification, manipulation, and recovery of its component nucleotide sequence by standard bio-chemical methods. Examples of such methods, including methods for PCR protocols that may be used herein, are disclosed in Sambrook et al., Molecular Cloning: A Laboratory Manual, 2nd ed., Cold Spring Harbor Laboratory, Cold Spring Harbor, N.Y. (1989), Current Protocols in Molecular Biology edited by F. A. Ausubel et al., John Wiley and Sons, Inc. (1987), and Innis, M. et al., eds., PCR Protocols: A Guide to Methods and Applications, Academic Press (1990).

As described herein, the nucleic acid molecules of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA, including translated, non-translated and control regions, may be isolated by conventional techniques, e.g., using any one of the cDNAs of the invention, or suitable fragments thereof, as a probe, to identify a piece of genomic DNA which can then be cloned using methods commonly known in the art. In general, nucleic acid molecules within the scope of the invention include sequences that hybridize to sequences of the invention under hybridization and wash conditions described above and of 5°, 10°, 15°, 20°, 25°, or 30° below the melting temperature of the DNA duplex of sequences of the invention, including any range of conditions subsumed within these ranges.

In another embodiment, the nucleic acids of the invention comprises a sequence substantially as set out in SEQ ID NO:6, SEQ ID NO:7, SEQ ID NO:8, SEQ ID NO:9, or SEQ ID NO:10. In one embodiment, the nucleic acids are at least 85%, at least 90%, or at least 95% identical to nucleotides SEQ ID NO:6, SEQ ID NO:7, SEQ ID NO:8, SEQ ID NO:9, or SEQ ID NO:10. In one embodiment, the nucleic acid comprises the nucleotide sequence SEQ ID NO:6, SEQ ID NO:7, SEQ ID NO:8, SEQ ID NO:9, or SEQ ID NO:10. In a further embodiment, the nucleic acid encodes a protein that is a sesquiterpenes synthase, as demonstrated, for example, in the enzyme assay described in the examples. In an embodiment, the nucleic acid encodes the polypeptide substantially set out in SEQ ID NO:1 or 2. Nucleic acids comprising regions conserved among different species, are also provided.

In yet another embodiment, the nucleic acid comprises a contiguous stretch of at least 50, 100, 250, 500, 750 contiguous nucleotides of SEQ ID NO:6, SEQ ID NO:7, SEQ ID NO:8, SEQ ID NO:9, or SEQ ID NO:10. Such contiguous fragments of these nucleotides may also contain at least one mutation so long as the mutant sequence retains the functionality of the original sequence and the capacity to hybridize to these nucleotides under low or high stringency conditions, such as for example, moderate or high stringency conditions. Such a fragment can be derived, for example, from nucleotide (nt) 200 to nt 1600, from nt 800 to nt 1600, from nt 1000 to nt 1600, from nt 200 to nt 1000, from nt 200 to nt 800, from nt 400 to nt 1600, or from nt 400 to nt 1000 of SEQ ID NO:6, SEQ ID NO:7, SEQ ID NO:8, SEQ ID NO:9, or SEQ ID NO:10.

As described above, polypeptides encoded by the nucleic acids of the invention are encompassed by the invention. The isolated nucleic acids of the invention may be selected from a nucleic acid encoding the polypeptide substantially set out in SEQ ID NO:1, SEQ ID NO:2, SEQ ID NO:3, SEQ ID NO:4, or SEQ ID NO:5. In one embodiment, the polypeptides are at least 85%, at least 90%, or at least 95% identical to SEQ ID NO:1, SEQ ID NO:2, SEQ ID NO:3, SEQ ID NO:4, or SEQ ID NO:5.

In one embodiment, a polypeptide of the invention comprises an amino acid sequence as set out in SEQ ID NO:1, SEQ ID NO:2, SEQ ID NO:3, SEQ ID NO:4, or SEQ ID NO:5. Preferably, the polypeptide of the invention comprises an amino acid sequence as set out in SE ID NO: 1 or 2. In another embodiment, the polypeptide comprises an amino acid sequence substantially as set out in of SEQ ID NO:1, SEQ ID NO:2, SEQ ID NO:3, SEQ ID NO:4, or SEQ ID NO:5. In yet another embodiment, the polypeptide comprises an amino acid sequence that is at least 85% identical, at least 90% or at least 95% identical to of SEQ ID NO:1, SEQ ID NO:2, SEQ ID NO:3, SEQ ID NO:4, or SEQ ID NO:5. In one embodiment, the polypeptide is a sesquiterpene synthase, as demonstrated, for example, in the enzyme assay described below.

Due to the degeneracy of the genetic code wherein more than one codon can encode the same amino acid, multiple DNA sequences can code for the same polypeptide. Such variant DNA sequences can result from genetic drift or artificial manipulation (e.g., occurring during PCR amplification or as the product of deliberate mutagenesis of a native sequence). The present invention thus encompasses any nucleic acid capable of encoding a protein derived from the SEQ ID NO:6, SEQ ID NO:7, SEQ ID NO:8, SEQ ID NO:9, or SEQ ID NO:10 or variants thereof.

Deliberate mutagenesis of a native sequence can be carried out using numerous techniques well known in the art. For example, oligonucleotide-directed site-specific mutagenesis procedures can be employed, particularly where it is desired to mutate a gene such that predetermined restriction nucleotides or codons are altered by substitution, deletion or insertion. Exemplary methods of making such alterations are disclosed by Walder et al. (Gene 42:133, 1986); Bauer et al. (Gene 37:73, 1985); Craik (BioTechniques, Jan. 12-19, 1985); Smith et al. (Genetic Engineering: Principles and Methods, Plenum Press, 1981); Kunkel (Proc. Natl. Acad. Sci. USA 82:488, 1985); Kunkel et al. (Methods in Enzymol. 154:367, 1987); and U.S. Pat. Nos. 4,518,584 and 4,737,462.

In one embodiment, the invention provides for isolated polypeptides. As used herein, the term "polypeptides" refers to a genus of polypeptide or peptide fragments that encompass the amino acid sequences identified herein, as well as smaller fragments. Alternatively, a polypeptide may be defined in terms of its antigenic relatedness to any peptide encoded by the nucleic acid sequences of the invention. Thus, in one embodiment, a polypeptide within the scope of the invention is defined as an amino acid sequence comprising a linear or 3-dimensional epitope shared with any peptide encoded by the nucleic acid sequences of the invention. Alternatively, a polypeptide within the scope of the invention is recognized by an antibody that specifically recognizes any peptide encoded by the nucleic acid sequences of the invention. Antibodies are defined to be specifically binding if they bind polypeptides of the invention with a $K_a$ of greater than or equal to about $10^7$ $M^{-1}$, such as greater than or equal to $10^8$ $M^{-1}$.

A polypeptide "variant" as referred to herein means a polypeptide substantially homologous to a native polypeptide, but which has an amino acid sequence different from that encoded by any of the nucleic acid sequences of the invention because of one or more deletions, insertions or substitutions.

Variants can comprise conservatively substituted sequences, meaning that a given amino acid residue is replaced by a residue having similar physiochemical characteristics. Examples of conservative substitutions include substitution of one aliphatic residue for another, such as lie, Val, Leu, or Ala for one another, or substitutions of one polar residue for another, such as between Lys and Arg; Glu and Asp; or Gln and Asn. See Zubay, Biochemistry, Addison-Wesley Pub. Co., (1983). The effects of such substitutions can be calculated using substitution score matrices such a PAM-120, PAM-200, and PAM-250 as discussed in Altschul, (J. Mol. Biol. 219:555-65,1991). Other such conservative substitutions, for example, substitutions of entire regions having similar hydrophobicity characteristics, are well known.

Naturally-occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides encoded by the sequences of the invention.

Variants of the sesquiterpenes synthases of the invention may be used to attain desired enhanced or reduced enzymatic activity, modified regiochemistry or stereochemistry, or altered substrate utilization or product distribution. A variant or site direct mutant may be made by any methods known in the art.

As stated above, the invention provides recombinant and non-recombinant, isolated and purified polypeptides, such as from citrus plants. Variants and derivatives of native polypeptides can be obtained by isolating naturally-occurring variants, or the nucleotide sequence of variants, of other or same plant lines or species, or by artificially programming mutations of nucleotide sequences coding for native citrus polypeptides. Alterations of the native amino acid sequence can be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene wherein predetermined codons can be altered by substitution, deletion or insertion.

In one embodiment, the invention contemplates: vectors comprising the nucleic acids of the invention. For example, a vector comprising at least one nucleic acid chosen from (a) a nucleic acid comprising the nucleotide sequence substantially as set out in SEQ ID NO:6, SEQ ID NO:7, SEQ ID NO:8, SEQ ID NO:9, or SEQ ID NO:10; (b) a nucleic acid encoding the polypeptide substantially set out in SEQ ID NO:1, SEQ ID NO:2, SEQ ID NO:3, SEQ ID NO:4, or SEQ ID NO:5; and (c) a nucleic acid that hybridizes to the nucleic acid of (a) or (b) under low stringency conditions, wherein the polypetide encoded by said nucleic acid is a sesquiterpene synthase.

A vector as used herein includes any recombinant vector including but not limited to viral vectors, bacteriophages and plasmids.

Recombinant expression vectors containing a nucleic acid sequence of the invention can be prepared using well known methods. In one embodiment, the expression vectors include a cDNA sequence encoding the polypeptide operably linked to suitable transcriptional or translational regulatory nucleotide sequences, such as those derived from a mammalian, microbial, viral, or insect gene. Examples of regulatory sequences include transcriptional promoters, operators, or enhancers, mRNA ribosomal binding sites, and appropriate sequences which control transcription and translation initiation and termination. Nucleotide sequences are "operably linked" when the regulatory sequence functionally relates to the cDNA sequence of the invention. Thus, a promoter nucleotide sequence is operably linked to a cDNA sequence if the promoter nucleotide sequence controls the transcription of the cDNA sequence. The ability to replicate in the desired host cells, usually conferred by an origin of replication, and a selection gene by which transformants are identified can additionally be incorporated into the expression vector.

In addition, sequences encoding appropriate signal peptides that are not naturally associated with the polypeptides of the invention can be incorporated into expression vectors. For example, a DNA sequence for a signal peptide (secretory leader) can be fused in-frame to a nucleotide sequence of the invention so that the polypeptides of the invention is initially translated as a fusion protein comprising the signal peptide. A signal peptide that is functional in the intended host cells enhances extracellular secretion of the expressed polypeptide. The signal peptide can be cleaved from the polypeptide upon secretion from the cell.

Fusions of additional peptide sequences at the amino and carboxyl terminal ends of the polypeptides of the invention can be used to enhance expression of the polypeptides or aid in the purification of the protein.

In one embodiment, the invention includes a host cell comprising a nucleic acid of the invention. Another embodiment of the invention is a method of making a recombinant host cell comprising introducing the vectors of the invention, into a host cell. In a further embodiment, a method of producing a polypeptide comprising culturing the host cells of the invention under conditions to produce the polypeptide is contemplated. In one embodiment the polypeptide is recovered. The methods of invention include methods of making at least one sesquiterpene synthase of the invention comprising culturing a host cell comprising a nucleic acid of the invention, and recovering the sesquiterpene synthase accumulated.

Suitable host cells for expression of polypeptides of the invention include prokaryotes, yeast or higher eukaryotic cells. Appropriate cloning and expression vectors for use with bacterial, fungal, yeast, and mammalian cellular hosts are described, for example, in Pouwels et al., Cloning Vectors: A Laboratory Manual, Elsevier, N.Y., (1985). Cell-free translation systems could also be employed to produce the disclosed polypeptides using RNAs derived from DNA constructs disclosed herein.

Prokaryotes include gram negative or gram positive organisms, for example, *E. coli* or Bacilli. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, the polypeptides can include a N-terminal methionine residue to facilitate expression of the recombinant polypeptide in the prokaryotic host cell. The N-terminal methionine can be cleaved from the expressed recombinant polypeptide.

Examples of useful expression vectors for prokaryotic host cells include those derived from commercially available plasmids such as the cloning vector pET plasmids (Novagen, Madison, Wis., USA) or yet pBR322 (ATCC 37017). pBR322 contains genes for ampicillin and tetracycline resistance and thus provides simple means for identifying transformed cells. To construct an expression vector using pBR322, an appropriate promoter and a DNA sequence encoding one or more of the polypeptides of the invention are inserted into the pBR322 vector. Other commercially available vectors include, for example, pKK223-3 (Pharmacia Fine Chemicals, Uppsala, Sweden) and pGEM-1 (Promega Biotec, Madison, Wis., USA). Other commercially available vectors include those that are specifically designed for the expression of proteins; these would include pMAL-p2 and pMAL-c2 vectors that are used for the expression of proteins fused to maltose binding protein (New England Biolabs, Beverly, Mass., USA).

Promoter sequences commonly used for recombinant prokaryotic host cell expression vectors include bacteriophage T7 promoter (Studier F. W. and Moffatt B. A., J. Mol. Biol. 189:113, 1986), β-lactamase (penicillinase), lactose promoter system (Chang et al., Nature 275:615, 1978; and Goeddel et al., Nature 281:544, 1979), tryptophan (trp) promoter system (Goeddel et al., Nucl. Acids Res. 8:4057, 1980; and EP-A-36776), and tac promoter (Maniatis, MoLecular Cloning: A Laboratory Manual, Cold Spring Harbor Laboratory, p. 412, 1982). A particularly useful prokaryotic host cell expression system employs a phage λ PL promoter and a cl857ts thermolabile repressor sequence. Plasmid vectors available from the American Type Culture Collection ("ATCC"), which incorporate derivatives of the PL promoter, include plasmid pHUB2 (resident in *E. coli* strain JMB9 (ATCC 37092)) and pPLc28 (resident in *E. coli* RR1 (ATCC 53082)).

Polypeptides of the invention can also be expressed in yeast host cells, preferably from the *Saccharomyces* genus (e.g., *S. cerevisiae*). Other genera of yeast, such as *Pichia* or *Kluyveromyces* (e.g. *K. lactis*), can also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionine, 3-phosphoglycerate kinase (Hitzeman et al., J. Biol. Chem. 255:2073, 1980), or other glycolytic enzymes (Hess et al., J. Adv. Enzyme Reg. 7:149, 1968; and Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., Gene, 107:285-195 (1991); and van den Berg et. al., Bio/Technology, 8:135-139 (1990). Another alternative is the glucose-repressible ADH2 promoter described by Russell et al. (J. Biol. Chem. 258:2674, 1982) and Beier et al. (Nature 300:724, 1982). Shuttle vectors replicable in both yeast and *E. coli* can be constructed by inserting DNA sequences from pBR322 for selection and replication in *E. coli* (Ampr gene and origin of replication) into the above-described yeast vectors.

One embodiment of the invention is a non-human organism modified to harbor a nucleic acid of the invention. The non-human organism and/or host cell may be modified by any methods known in the art for gene transfer including, for example, the use of deliver devices such as lipids and viral vectors, naked DNA, electroporation and particle-mediated gene transfer. In one embodiment, the non-human organism is a plant, insect or microorganism.

For example, in one embodiment the invention provides a method of making at least one sesquiterpene synthase comprising culturing a host modified to contain at least one nucleic acid under conditions conducive to the production of said at least one sesquiterpene synthase wherein said at least one nucleic acid is chosen from (a) a nucleic acid comprising the nucleotide sequence substantially as set out in SEQ ID NO:6, SEQ ID NO:7, SEQ ID NO:8, SEQ ID NO:9, or SEQ ID NO:10; (b) a nucleic acid encoding the polypeptide substantially set out in SEQ ID NO:1, SEQ ID NO:2, SEQ ID NO:3, SEQ ID NO:4, or SEQ ID NO:5; and (c) a nucleic acid that hybridizes to the nucleic acid of (a) or (b) under low stringency conditions, wherein the polypetide encoded by said nucleic acid is a sesquiterpene synthase.

In a further embodiment, the host is a plant such as tobacco, animal or microorganism also including but not limited to bacterial cells, yeast cells, plant cells, and animal cells. As used herein, plant cells and animals cells include the use of plants and animals as a host. For example, in some embodiments of the invention, expression is in a genetically modified non-human organism.

In one embodiment, mammalian or insect host cell culture systems are employed to express recombinant polypeptides of the invention. Baculovirus systems for production of heterologous proteins in insect cells are reviewed by Luckow and Summers, Bio/Technology 6:47 (1988). Established cell lines of mammalian origin also can be employed. Examples of suitable mammalian host cell lines include the COS-7 line of monkey kidney cells (ATCC CRL 1651) (Gluzman et al., Cell 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line (ATCC CRL 10478) derived from the African green monkey kidney cell line CVI (ATCC CCL 70) as described by McMahan et al. (EMBO J. 10: 2821, 1991).

Established methods for introducing DNA into mammalian cells have been described (Kaufman, R. J., Large Scale Mammalian Cell Culture, 1990, pp. 15-69). Additional protocols using commercially available reagents, such as Lipofectamine (Gibco/BRL) or Lipofectamine-Plus, can be used to transfect cells (Felgner et al., Proc. Natl. Acad. Sci. USA 84:7413-7417, 1987). In addition, electroporation can be used to transfect mammalian cells using conventional procedures, such as those in Sambrook et al. Molecular Cloning: A Laboratory Manual, 2 ed. Vol. 1-3, Cold Spring Harbor Laboratory Press, 1989). Selection of stable transformants can be performed using resistance to cytotoxic drugs as a selection method. Kaufman et al., Meth. in Enzymology 185:487-511,1990, describes several selection schemes, such as dihydrofolate reductase (DHFR) resistance. A suitable host strain for DHFR selection can be CHO strain DX-B11, which is deficient in DHFR (Urlaub and Chasin, Proc. Natl. Acad. Sci. USA 77:4216-4220,1980). A plasmid expressing the DHFR cDNA can be introduced into strain DX-B11, and only cells that contain the plasmid can grow in the appropriate selective media.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and later promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., Nature 273:113,1978; Kaufman, Meth. in Enzymology, 1990).

There are several methods known in the art for the creation of transgenic plants. These include, but are not limited to: electroporation of plant protoplasts, liposome-mediated transformation, polyethylene-glycol-mediated transformation, microinjection of plant cells, and transformation using viruses. In one embodiment, direct gene transfer by particle bombardment is utilized.

Direct gene transfer by particle bombardment provides an example for transforming plant tissue. In this technique a particle, or microprojectile, coated with DNA is shot through the physical barriers of the cell. Particle bombardment can be used to introduce DNA into any target tissue that is penetrable by DNA coated particles, but for stable transformation, it is imperative that regenerable cells be used. Typically, the particles are made of gold or tungsten. The particles are coated with DNA using either CaCl2 or ethanol precipitation methods which are commonly known in the art.

DNA coated particles are shot out of a particle gun. A suitable particle gun can be purchased from Bio-Rad Laboratories (Hercules, Calif.). Particle penetration is controlled by varying parameters such as the intensity of the explosive burst, the size of the particles, or the distance particles must travel to reach the target tissue.

The DNA used for coating the particles may comprise an expression cassette suitable for driving the expression of the gene of interest that will comprise a promoter operably linked to the gene of interest.

Methods for performing direct gene transfer by particle bombardment are disclosed in U.S. Pat. No. 5,990,387 to Tomes et al.

In one embodiment, the cDNAs of the invention may be expressed in such a way as to produce either sense or antisense RNA. Antisense RNA is RNA that has a sequence which is the reverse complement of the mRNA (sense RNA) encoded by a gene. A vector that will drive the expression of antisense RNA is one in which the cDNA is placed in "reverse orientation" with respect to the promoter such that the non-coding strand (rather than the coding strand) is transcribed. The expression of antisense RNA can be used to down-modulate the expression of the protein encoded by the mRNA to which the antisense RNA is complementary. Vectors producing antisense RNA's could be used to make transgenic plants, as described above.

In one embodiment, transfected DNA is integrated into a chromosome of a non-human organism such that a stable recombinant systems results. Any chromosomal integration method known in the art may be used in the practice of the invention, including but not limited to, recombinase-mediated cassette exchange (RMCE), viral site specific chromosomal insertion, adenovirus, and pronuclear injection.

A further embodiment of the invention is methods of making terpenoids and sesquiterpene compounds, for example, using the nucleotides and polypeptides of the invention. Examples include methods of making at least one terpenoid comprising contacting at least one acyclic pyrophosphate terpene precursor with at least one polypeptide encoded by a nucleic acid chosen from (a) a nucleic acid comprising the nucleotide sequence substantially as set out in SEQ ID NO:6, SEQ ID NO:7, SEQ ID NO:8, SEQ ID NO:9, or SEQ ID NO:10; (b) a nucleic acid encoding the polypeptide substantially set out in SEQ ID NO:1, SEQ ID NO:2, SEQ ID NO:3, SEQ ID NO:4, or SEQ ID NO:5; and (c) a nucleic acid that hybridizes to the nucleic acid of (a) or (b) under low stringency conditions, wherein the polypetide encoded by said nucleic acid is a sesquiterpene synthase, and isolating at least one terpenoid produced. Another example is a method of making at least one terpenoid comprising contacting at least one acyclic pyrophosphate terpene precursor with at least one polypeptide substantially set out in SEQ ID NO:1, SEQ ID NO:2, SEQ ID NO:3, SEQ ID NO:4, or SEQ ID NO:5 and isolating at least one terpenoid produced.

As used herein an acyclic pyrophosphate terpene precursor is any acyclic pryrophosphate compound that is a precursor to the production of at least one terpene including but not limited to geranyl-pyrophosphate (GPP), farnesyl-pyrophosphate (FPP) and geranylgeranyl-pyrophosphate (GGPP).

Figure 2:
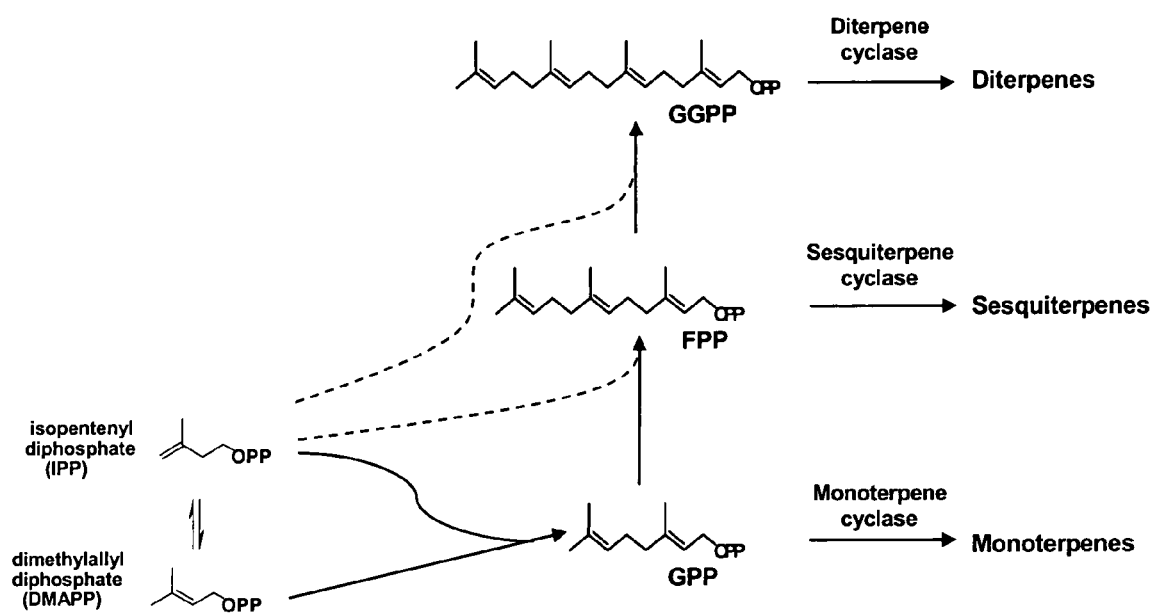
FIG. 2: Example terpene biosynthesis from isopentenyl diphosphoate.

In one embodiment, the at least one terpenoid is chosen from sesquiterpenes. In one embodiment, the at least one acyclic pyrophosphate terpene precursor is farnesyl-pyrophosphate. In a further embodiment, the at least one sesquiterpenes is chosen from bicylogermacrene((E,E)-3,7,11,11-tetramethyl-bicyclo[8.1.0]undeca-2,6-diene), cubebol ((1R,4S,5R,6R,7S,10R)-7-isopropyl-4,10-dimethyl-tricyclo [4.4.0.0(1,5)]decan-4-ol, valencene ((+)-(1R)-1,2,3,5,6,7,8,8A-octahydro-7-isopropenyl-1@,8A@-dimethylnaph-thaalene), α-cubebene, germacrene D, and δ-cadinene(rel-(1R,8AS)-1,2,3,5,6,8A-hexahydro-1-isopropyl-4,7-dimethylnaphtalene) (FIG. 2). The terpenoids of the invention may be isolated by any method used in the art including but not limited to chromatography, extraction and distillation.

In one embodiment, the distribution of products or the actual products formed may be altered by varying the pH at which the synthase contacts the acyclic pyrophosphate terpene precursor, such as, for example, farnesyl-pyrophosphate. In one embodiment, the pH is 7. In a further embodiment the pH is less than 7, such as, for example, 6, 5, 4, and 3.

Also within the practice of the invention is an organism (e.g., micro-organism or plant) that is used to construct a platform for high level production of a substrate of sesquiterpene synthases (e.g., FPP) and the introduction of a nucleic acid of the invention into the organism. For example, at least one nucleic acid of the invention that encodes a sesquiterpene synthase is incorporated into a non-human organism that produces FPP thereby effecting conversion of FPP to a sesquiterpene, and the subsequent metabolic production of the sesquiterpene. In one embodiment, this results in a platform for the high level production of sesquiterpenes.

In one embodiment, the nucleic acids of the invention are used to create other nucleic acids coding for sesquiterpene synthases. For example, the invention provides for a method of identifying a sesquiterpene synthases comprising constructing a DNA library using the nucleic acids of the invention, screening the library for nucleic acids which encode for at least one sesquiterpene synthase. The DNA library using the nucleic acids of the invention may be constructed by any process known in the art where DNA sequences are created using the nucleic acids of the invention as a starting point, including but not limited to DNA suffling. In such a method, the library may be screened for sesquiterpene synthases using a functional assay to find a target nucleic acid that encodes a sesquiterpene synthase. The activity of a sesquiterpene synthase may be analyzed using, for example, the methods described herein. In one embodiment, high through put screening is utilized to analyze the activity of the encoded polypeptides.

As used herein a "nucleotide probe" is defined as an oligonucleotide or polynucleotide capable of binding to a target nucleic acid of complementary sequence through one or more types of chemical bonds, through complementary base pairing, or through hydrogen bond formation. As described above, the oligonucleotide probe may include natural (ie. A, G, C, or T) or modified bases (7-deazaguanosine, inosine, etc.). In addition, bases in a nucleotide probe may be joined by a linkage other than a phosphodiester bond, so long as it does not prevent hybridization. Thus, oligonucleotide probes may have constituent bases joined by peptide bonds rather than phosphodiester linkages.

A "target nucleic acid" herein refers to a nucleic acid to which the nucleotide probe or molecule can specifically hybridize. The probe is designed to determine the presence or absence of the target nucleic acid, and the amount of target nucleic acid. The target nucleic acid has a sequence that is complementary to the nucleic acid sequence of the corresponding probe directed to the target. As recognized by one of skill in the art, the probe may also contain additional nucleic acids or other moieties, such as labels, which may not specifically hybridize to the target. The term target nucleic acid may refer to the specific nucleotide sequence of a larger nucleic acid to which the probe is directed or to the overall sequence (e.g., gene or mRNA). One skilled in the art will recognize the full utility under various conditions.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result. The percentages are given on a weight basis.

The following examples are intended to illustrate the invention without limiting the scope as a result.

EXAMPLES

Material

A grapefruit (Citrus paradisi) flavedo was used as starting material for the experiments described herein. The flavedo (external, colored portion of the fruit peel) contains the oil glands that are the site of terpene biosynthesis. The grapefruit flavedo was prepared at Simone Gatto (Sicily) from freshly picked ripening fruits. The flavedo (3-4 mm thickness) was cut-off, immediately frozen and kept frozen during the transport and all subsequent steps in order to prevent from degradation.

Example 1

Isolating Sesquiterpene Synthase cDNA using RT-PCR

Figure 4:
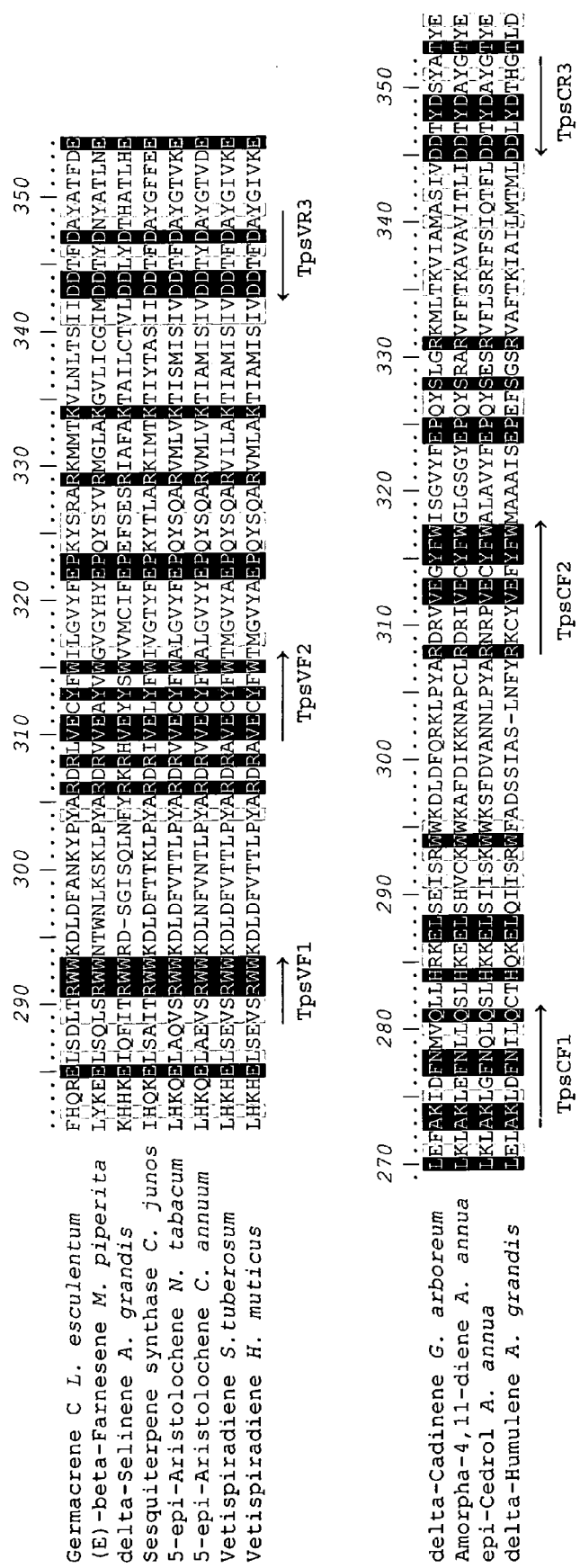
FIG. 4: Central part of the alignments of the amino acid sequences of two groups of sesquitepene synthase (Germacrene C L. esculentum δ-cadine synthase (SEQ ID NO:11); (E)-beta-Farnesene M. piperita (SEQ ID NO:12); delta-Selinene A. grandis (SEQ ID NO:13); Sesquiterpene synthase C. junos (SEQ ID NO:14); 5-epi-Aristolochene N. tabacum (SEQ ID NO:15); 5-epi-Aristolochene C. annuum (SEQ ID NO:16); Vetispiradiene S. tuberosum (SEQ ID NO:17); Vetispiradiene H. muticus (SEQ ID NO:18); delta-Cadinene G. arboreum (SEQ ID NO:19); Amorpha-4,11-diene A. annua (SEQ ID NO:20); epi-Cedrol A. annua (SEQ ID NO:21); delta-Humulene A. grandis (SEQ ID NO:22)) and the sequence of the deduced degenerate primers (TpsVF1 (SEQ ID NO:23); TpsVF2 (SEQ ID NO:24); TpsVR3 (SEQ ID NO:25); TpsCF1 (SEQ ID NO:26); TpsCF2 (SEQ ID NO:27); TpsCR3 (SEQ ID NO:28)). The arrows below each alignment show the regions of the alignment used to design the degenerate primers and their orientation.

The deduced amino-acid sequences of plant sesquiterpene synthases were aligned to identify conserved regions and design plant sesquiterpene synthases-specific oligonucleotides. In order to obtain better sequence homology, the sequences were separated into two groups (FIG. 4). The first group contained the sequences of the Germacrene C synthase from *Lycopersicon esculentum* cv. VFNT cherry (Colby et al, 1998), the (E)-β-farnesene synthase from *Mentha* x piperita (Crock et al, 1997), the 8-selinene synthase from *Abies grandis* (Steele et al, 1998), a sesquiterpene synthase from Citrus junos (GenBank accession no. AF288465) the 5-epi aristolochene synthases from *Nicotiana tabacum* (Facchini and Chappell, 1992) and from *Capsicum annuum* (Back et al, 1998), the vetispiradiene synthases from *Solanum tuberosum* and from *Hyoscyamus muticus* (Back and Chappel, 1995). The second group contained sequences of the (+)-δ-cadinene synthases from *Gossypium arboreum* (Chen et al. 1995), the amorpha-4,11-diene synthase (Mercke et al, 2000) and the epi-cedrol synthase (Merck et al, 1999) from *Artemisia annua* and the γ-humulene synthase from *Abies grandis* (Steele et al, 1998). The highest sequence homology was found in the central part of the sequences. Three regions containing sufficiently conserved amino-acids were selected and degenerated oligonucleotides specific for these regions were designed (i.e. two forward and one reverse primers were deduced from each alignment) (FIG. 4).

RT-PCR was performed using total RNA from grapefruit flavedo prepared by the Hot Borate technique and the different combination of the forward and reverse degenerated primers. The Hot Borate method for total RNA extraction was adapted from Wan and Wilkins (Wan et al. (1994) Anal. Biochem. 223, 7-12.). Tissues were crushed to a fine powder in liquid nitrogen using a mortar and pestle. The powder was added to 5 ml extraction buffer (200 mM borate, 30 mM EGTA, 10 mM DTT, 1% SDS, 1% NA deoxycholate, 2% PVP, 0.5% nonidet NP40) preheated at 80° C. The mixture was homogenized using an Ultraturax™ homogenizer and filtered through two layer of Miracloth™ filter (Calbiochem). The mixture was incubated 90 minutes at 42° C. in the presence of 0.5 mg/ml proteinase K (for protein/ribonuclease digestion). KCl was then added to 1 M final concentration and, after 1 hour incubation on ice, the mixture was placed in a centrifuge for 10 min at 1000 g and 4° C. The supernatant was recovered and ⅓ volume of 8M LiCl was added. The mixture was incubated over night at 4° C. and placed in a centrifuge for 20 minutes at 10000 g and 4° C. The supernatant was discarded and, the pellet washed with 2M LiCl and centrifuged again as before. The pellet was then resuspended in RNase-free distilled water, and 0.15 vol of 2 M potassium acetate solution and 2.5 volumes absolute ethanol were added. The RNA were precipitated by incubating 2 hours at −20° C. and pelleted by centrifugation as before. The RNA pellet was washed with 80% ethanol and resuspended in RNase free distilled water.

The concentration of RNA was estimated from the OD at 260 nm. The integrity of the RNA was evaluated on an agarose gel by verifying the integrity of the ribosomic RNA bands.

RT-PCR was performed using the Qiagen OneStep RT-PCR Kit and an Eppendorf Mastercycler gradiant thermal cycler. Typical reaction mixtures contained 10 µl 5× Qiagen OneStep RT-PCR buffer, 400 µM each dNTP, 400 nM each primer, 2 µl Qiagen OneStep RT-PCR Enzyme Mix, 1 µl RNasin® Ribonuclease Inhibitor (Promega Co.) and 1 µg total RNA in a final volume of 50 µl. The thermal cycler conditions were: 30 min at 50° C. (reverse transcription); 15 min at 95° C. (DNA polymerase activation); 40 cycles of 45 sec at 94° C., 10 sec at 42° C. to 45° C. (depending on the primer used), 45 sec to 90 sec (depending on the size of the DNA fragment to be amplified) at 72° C.; and 10 min at 72° C.

The size of the PCR products was evaluated on a 1% agarose gel. The bands corresponding to the expected size were excised from the gel, purified using the QIAquick® Gel Extraction Kit (Qiagen) and cloned in the pCR®2.1-TOPO vector using the TOPO TA cloning Kit (Invitrogen). Inserted cDNAs were then subject to DNA sequencing and the sequence compared against the GenBank non redundant protein database (NCBI) using the BLASTX algorithm (Altschul et al 1990).

The analysis by DNA sequencing and the Blast search of the PCR products with expected length (80 to 240 bp in size) revealed fragments of three different sesquiterpene synthases, which were named GFTpsA, GFtpsB and GFTpsC. The 180-bp GFTpsA fragment was amplified with the primers TpsVF1 and TpsVR3, the 115-bp GFtpsB fragment was amplified with the primers TpsVF2 and TpsVR3, and the 115-bp GFTpsA fragment was amplified with the primers TpsVF1 and TpsVR3. The deduced amino-acid sequences revealed significant differences between these three fragments (FIG. 5).

Example 2

Isolating Sesquiterpene Synthase cDNA using 5'/3'-RACE

To isolate the full-length sequences of the sesquiterpene synthases, a 5'/3'-RACE approach was first used. cDNA was synthesized using Marathon™ cDNA Amplification Kit (Clontech) and starting from 1 µg mRNA purified from total RNA prepared with the Hot Borate technique. The quality of the synthesized cDNA was poor, essentially small size cDNAs were obtained (average size of 0.5 Kb). However, using this cDNA, the 3'-end of the GFTpsB and GFTpsC were obtained using the gene specific primers GFTpsBRF1 and GFTpsBRF2 for GFTpsB and the gene specific primers GFTpsCRF1 and GFTpsCRF2 for GFTpsC (see Table 1). mRNA prepared by the guanidinium-thiocyanate/phenol extaction method gave higher quality cDNA with an average size of 2 Kb and allowed the isolation of the 5'-end sequence of GFTpsC using the gene specific primers GFTpsCRR1 and GFTpsRR2 (see Table 1), completing the full-length sequence of this clone. The 5'-end of GFTpsB and the 5'-end and 3'-end of GFTpsA could not be obtained by this approach.

The guanidinium-thiocyanate/phenol extraction method was based on the technique described by Chomczynski and Sacchi using the RNAClean™ solution from ThermoHybaid (Chomczynski, P., and Sacchi, N., (1987) Anal. Biochem. 162,156-159.). Briefly, 2 g of frozen tissues was crushed to a fine powder in liquid nitrogen using a mortar and pestle. The powder was transferred to 20 ml RNAClean™ solution and the suspension was homogenized using an Ultraturax™ homogenizer and filtered through Miracloth™ filter (Calbiochem). After addition of 0.1 volume of chloroform, the tube was placed on ice and centrifuged 20 min at 12000 g and 4° C. The upper aqueous phase was recovered and one volume of isopropanol was added. After 20 min. incubation at −20° C., the sample was centrifuged 20 min. at 12000 g and 4° C. The large white pellet obtained was washed with 70% ethanol and dried at room temperature. This pellet, containing the total RNA, was immediately subject to mRNA purification by oligodT-cellulose affinity chromatography using the FastTrack® 2.0 mRNA isolation Kit (Invitrogen). The manufacturer's protocol was followed except that after resuspension of the total RNA in the lysis buffer, the sample was heated at 100° C. instead of 65° C.

3' and 5' rapid amplification of cDNA ends (RACE) were performed using Marathon™ cDNA Amplification Kit (Clontech). The procedure began with the first-strand cDNA synthesis starting from mRNA using an oligo(dT) primer. After second-strand synthesis, specific adaptors were ligated to the double stranded cDNA (ds cDNA) ends. This procedure provided an uncloned library of adaptor-ligated ds cDNA. Purified grapefruit mRNA (1 µg) was used as starting material. The quality and quantity of cDNA was evaluated on an agarose gel.

The 3'- or 5'-end of the specific cDNAs were amplified with Advantage® 2 Polymerase Mix using a combination of gene- and adaptor-specific oligonucleotides. Typical RACE reaction mixtures contained, in a final volume of 50 µl, 5 µl 10×cDNA PCR Reaction Buffer (clontech), 200 nM each dNTP, 1 µl Advantage® 2 Polymerase Mix, 200 µM adaptor-specific primer (Clontech), 200 µM gene-specific primer (see Table 1) and 5 µl of 50 to 250 fold diluted adaptor-ligated cDNA. Amplification was performed on an Eppendorf Mastercycler gradiant thermal cycler. The thermal Cycling conditions were as follows: 1 min at 94° C., 5 cycles of 30 sec at 94° C. and 2 to 4 min at 72° C., 5 cycles of 30 sec at 94° C. and 2 to 4 min at 70° C., 20 cycles of 30 sec at 94° C. and 2 to 4 min at 68° C. When necessary a second round of amplification was performed using a nested adaptor-specific primer (Clontech) and a nested gene-specific primer.

The amplification products were evaluated, sub-cloned, and the sequence analyzed as above for the RT-PCR products.

TABLE 1

The following primers were used in the 3'/5'-RACE experiments:

| Name. | Description. | Sequence (5' to 3'). |
|---|---|---|
| GFTpsARF1 (SEQ ID NO:34) | 3'-RACE forward primer. | CTGGGAGTGTCCTATGAGCTCAATTTGG |
| GFTpsARF2 (SEQ ID NO:35) | GFTpsA 3'-RACE forward nested primer. | GTAGAATTTTTGCATCCAAAGTGGTGTGC |
| GFTpsARR1 (SEQ ID NO:36) | GFTpsA 5'-RACE reverse primer. | CACACCACTTTGGATGCAAAAATTCATC |
| GFTpsARR2 (SEQ ID NO:37) | GFTpsA 5'-RACE reverse nested primer. | CCAAATTGGGCTCATAGGACACTCCCAG |

TABLE 1-continued

The following primers were used in the 3'/5'-RACE experiments:

| Name. | Description. | Sequence (5' to 3'). |
|---|---|---|
| GFTpsBRF1 (SEQ ID NO:38) | GFTpsB 3'-RACE forward primer. | TAGGGACGTATTTTGAACCAAAGTAC |
| GFTpsBRF2 (SEQ ID NO:39) | GFTpsB 3'-RACE forward nested primer. | AAATAATGACCAAAACAATTTACACGG |
| GFTpsBRR1 (SEQ ID NO:40) | GFTpsB 5'-RACE reverse primer. | GCACTTTCATGTATTCTGGAAG |
| GFTpsBRR2 (SEQ ID NO:41) | GFTpsB 5'-RACE reverse nested primer. | GTTTGAGCTCTTCAAAGAAACC |
| GFTpsCRF1 (SEQ ID NO:42) | GFTpsC 3'-RACE forward primer. | AATGGGAGTGTATTTTGAGCCTCGATACTCC |
| GFTpsCRF2 (SEQ ID NO:43) | GFTpsC 3'-RACE forward nested primer. | GATATTTTCCAAAGTAATTGCAATGGCATCC |
| GFTpsCRR1 (SEQ ID NO:44) | GFTpsC 5'-RACE reverse primer. | GTTGCTAATATCCCACCTTTTGATAGC |
| GFTpsCRR2 (SEQ ID NO:45) | GFTpsC 5'-RACE reverse nested primer. | AAGTGTGCCATAGGCGTCGTAGG |
| GFTpsDRR1 (SEQ ID NO:46) | GFTpsD 5'-RACE reverse primer. | CTGTTCCGCAAGCTTAGGGGTTACATG |
| GFTpsDRR2 (SEQ ID NO:47) | GFTpsD 5'-RACE reverse nested primer. | CTGAGCTACCAATGACTTCAGGTGAGTGG |
| GFTpsERR1 (SEQ ID NO:48) | GFTpsE 5'-RACE reverse primer. | CAATTTTGCCATACACATCATAGATATCATC |
| GFTpsERR2 (SEQ ID NO:49) | GFTpsE 5'-RACE reverse nested primer. | AACAGAAGTCATGGAGATCACTTTCGTC |
| GFTpsERR3 (SEQ ID NO:50) | GFTpsE 5'-RACE reverse primer. | CGCAAGAGATGTTTTAAAGTTCCCATCC |
| GFTpsERR4 (SEQ ID NO:51) | GFTpsE 5'-RACE reverse nested primer. | TGAACATCAGCGGAAATTTTATAGCC |

Figure 6:
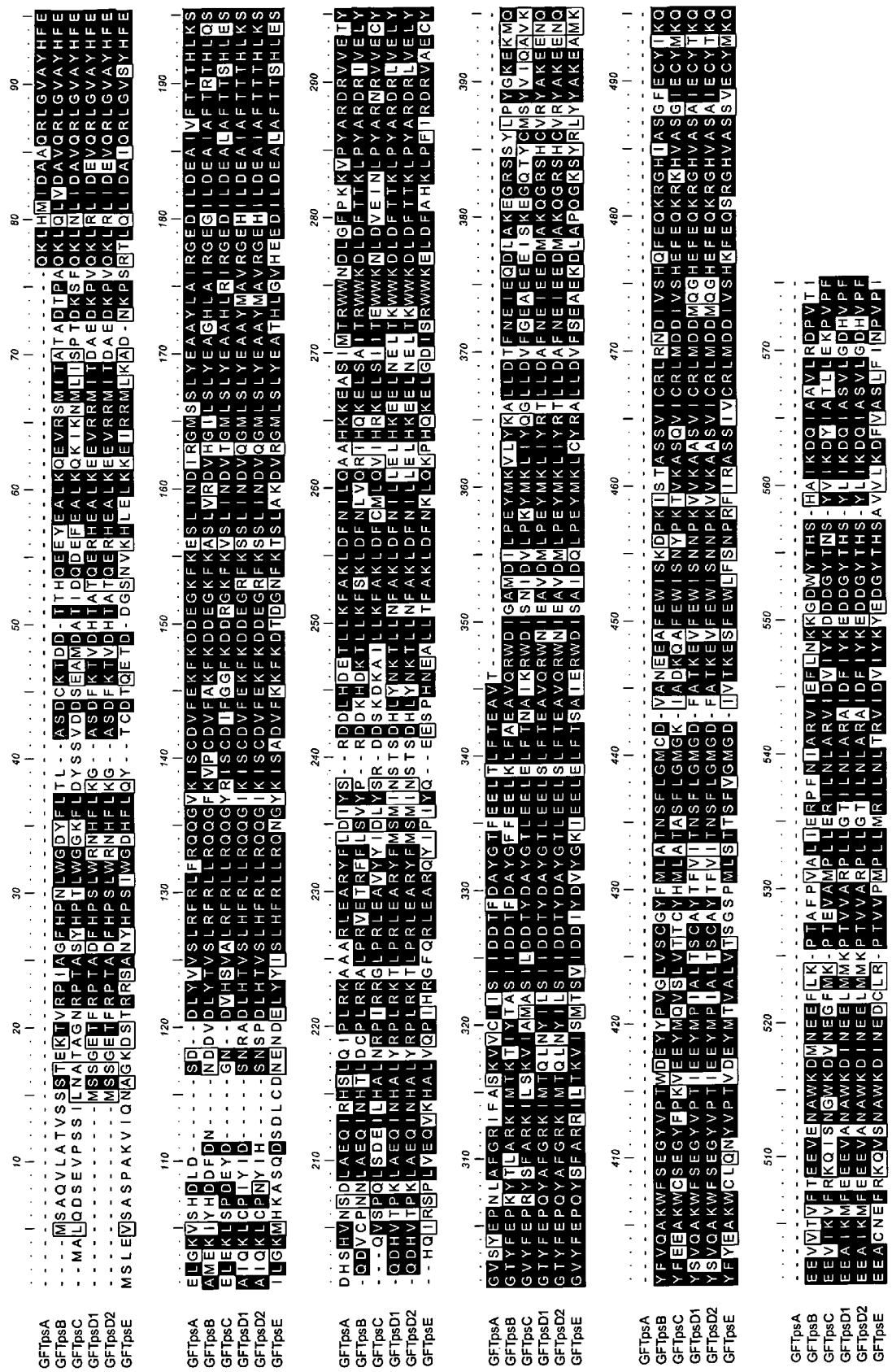
FIG. 6: Amino acid sequence alignment of the sesquiterpene synthases GFTpsA (partial clone) (SEQ ID NO:32), GFTpsB (SEQ ID NO:3), GFTbsC (SEQ ID NO:1), GFTpsD1 (SEQ ID NO:4), GFTpsD2 (SEQ ID NO:5), and GFTpsE (SEQ ID NO:2) from C. paradisi.

The partial GFTpsB cDNA obtained by 3'-RACE revealed high sequence identity to a putative terpene synthase cDNA found in the public databases (GeneBank accession no. AF288465) and isolated from Citrus junos. Primers specific for the sequence of this terpene synthase were designed: one pair of forward and reverse primers OunosF1 and junosR1) designed against the non-coding region of the *C. junos* terpene synthase and one pair of forward and reverse primers (junosF2 and junos R2) designed in the coding region including the start and stop codons. PCR on the grapefruit Marathon™ cDNA library using the primers junosF1 and junosR1 produced no amplicon. Using the junosF2 and junosR2 primers a fragment of 1.6 Kb was amplified. DNA sequencing confirmed this PCR product as being a 1669-bp full-length sesquiterpene synthase of the GFTpsB clone. (FIG. 6).

Example 3 cDNA Library Screening and EST Sequencing

In order to obtain the full-length cDNA of the partial clones obtained by the PCR approach, a cDNA library prepared from grapefruit flavedo mRNA was constructed. cDNA synthesis and library construction were performed using the Uni-ZAP® XR library construction Kit (Stratagene) according to manufacturer's protocol starting from 7.5 µg grapefruit flavedo mRNA (prapared by the Guanidinium-Thiocyanate/Phenol method). The original titer of the library was $2 \times 10^7$ PFU (plaques forming units) and the average insert size was 1.1 Kb.

Two approaches were used to isolate sesquiterpene synthases encoding cDNAs from the cDNA library: EST sequencing and screening using a DNA probe. For EST (expressed sequence tag) sequencing, a fraction of the library was used to excise the pBluescript phagemid from the Uni-ZAP XR vector according to Stratagene's mass excision protocol. Resulting transformed bacterial colonies (576) were randomly picked and the plasmid purified. One sequencing reaction was performed for each clone using the T3 primer. The sequences were first edited to remove vector sequences and compared against the GenBank non redundant protein database (NCBI) using the BLASTX algorithm (Altschul et al 1990).

The library was screened with digoxigenin (DIG)-labeled DNA probes. The probes were synthesized by incorporation of DIG-dUTP into a DNA fragment by PCR using the PCR DIG (digoxigenin) Probe Synthesis Kit (Roche Diagnostics). A 149-bp GFTpsA-derived DNA probe was amplified from an aliquot of the library using the forward primer GFTpsAproF (SEQ ID NO:52) (5'-ACGATTTAGGCTTC-CCTAAAAAGG-3') and the reverse primer GFTpsAproR (SEQ ID NO:53) (5'-TATTATGGAATATTATGCACAC-CAC-3'). A 1036-bp GFTpsB-derived probe was amplified from the pET-GFTpsB2-2 plasmid using the forward primer junosF2 (SEQ ID NO:54) (5'-AAATGTCCGCTCAAGT-TCTAGCAACGG-3') and the reverse primer GFTpsBRR2 (SEQ ID NO:41). A 1008-bp GFTpsC-derived DNA probe was amplified from the pET-GFTpsC plasmid using the forward primer GFTpsCpetF1 (SEQ ID NO:55) (5'-ATG-GCACTTCAAGATTCAGAAGTTCC-3') and the reverse primer GFTpsCRR1 (SEQ ID NO:44).

The probes were hybridized to plaques lifts, prepared from plates containing 5,000 to 25,000 PFU, at 40° C. in Dig Easy Hyb hybridization solution (Roche Diagnostics). The detection of the probe-target hybrids on the membranes was performed by chemiluminescence using Anti-Digoxigenin-Alkaline Phosphatase (Roche Diagnostics) and CDP-Star alkaline phosphate substrate (Roche Diagnostics), and the visualization was made on a VersaDoc Imaging System (BioRad).

Phages from positives signals were cored from the agar plates and subject to secondary and if necessary to tertiary screening to achieve single plaques positive signals. The positive isolates were in vivo excised and the insert sequenced as described above.

The library was screened using DNA probes prepared from GFTpsA, GFTpsB and GFTpsC. This approach yielded three different sesquiterpene synthase cDNAs. Two of them were previously found clones: one clone, named GF2-30-1, was a 5'-end 300-bp truncated form of the GFTpsC cDNA; the second clone, named 9-13-6, was a partial clone of GFtpsA that was truncated at its 5'-end by approximately 168-bp as judged by comparison to other sesquiterpene synthases. The 9-13-6 clone provided 618-bp additional 5'-end sequence information compared to the above mentioned partial GFTpsA clone obtained by RT-PCR. At its 3'-end, the 9-13-6 clone was also incomplete. Approximately 680 nucleotides were missing and were replaced by a 600-bp fragment of no defined function. The third sesquiterpene synthase encoding cDNA obtained by screening, GF2-5-11, encoded a new sesquiterpene synthase that was named GFTpsD. This clone was truncated at the 5'-end, but the missing 414-bp was recovered by 5'-RACE using the primers described in Table 1. The full-length GFTpsD was then amplified from Marathon™ cDNA library and cloned in the bacterial expression vector as described above. Analysis of the DNA sequence of several full-length GFTpsD cDNAs revealed that two closely related sesquiterpene synthases with minor sequence differences were present, they were named GFTpsD1 and GFTpsD2 (FIG. 6). The deduced amino-acid sequence of these two variants differed from each other by 4 residues.

For the EST sequencing approach, 576 clones were sequenced. Among them, only three clones encoded putative terpene-synthases like proteins and more precisely, two different sesquiterpene synthase-like and one monoterpene synthase-like proteins. One of the two sesquiterpene synthase-like clones (clone GF002-G3) was the previously identified clone GFTpsD1. The second (clone GF006-G7) was a truncated cDNA encoding a new sesquiterpene synthase that was named GFTpsE. This clone was again 5'-end truncated (by approximately 800 bp) and the missing fragment could be amplified by 5'-RACE in two stages as follows. A first 5'-RACE using the primers GFTpsERR1 and GFTpsERR2 (see Table 1) provided 500 additional 5'-end nucleotides and a second 5'RACE using the primers GFTps-ERR3 and GFTpsERR4 (see Table 1) provided the missing 5'-end DNA sequence to reconstitute the full-length GFTpsE cDNA (FIG. 6).

Example 4

Construction of Plasmids and Enzyme Expression

Construction of Expression Plasmids.

The cDNA were sub-cloned in the pET11a expression plasmid (Novagen) for functional expression of the sesquiterpene synthases. For GFTpsB, GFtpsD and GFTpsE, the full-length cDNAs were amplified by PCR to introduce an NdeI site at the 5'-end including the start codon and a BamHI site at the 3'-end immediately after the stop codon. For GFTpsB, the forward primer GFTpsBNdeI (SEQ ID NO:56) 5'-GCATGTTCCATATGTCCGCTCAAGT-TCTAGCAACGGTTTCC-3'(NdeI site in italics, stat codon underlined) and the reverse primer GFTpsBBam (SEQ ID NO:57)5'-CGCGGATCCTCAGATGGTAA-CAGGGTCTCTGAGCACTGC-3'(BamHI site in italics, stop codon underlined) were used. In the same way, the forward primer GFTpsDNdeI (SEQ ID NO:58) 5'-GCAT-GTTCCATATGTCGTCTGGAGAAACATTTCGTCC-3'and the reverse primer GFTpsDBam (SEQ ID NO:59) 5'-CGCGGATCCTCAAAATGGAACGTGGTCTCCTAG-3'were used for GFTpsD and the forward primer GFTpsEN-deI (SEQ ID NO:60) 5'-GCATGTTCCATATGTCTTTG-GAAGTTTCAGCCTCTCCTG-3'and the reverse primer GFTpsEBam (SEQ ID NO:61) 5'-CGCGGATCCT-CATATCGGCACAGGATTAATAAACAAAGAAGC-3'were used for GFTpsE.

The amplifications were performed using the Pfu DNA polymerase (Promega) in a final volume of 50 µl containing 5 µl of Pfu DNA polymerase 10× buffer, 200 µM each dNTP, 0.4 µM each forward and reverse primer, 2.9 units Pfu DNA polymerase and 5 µl of 100-fold diluted cDNA (prepared as described above using the Marathon™ cDNA Amplification Kit (Clontech)). The thermal cycling conditions were as follows: 2 min at 95° C.; 25 cycles of 30 sec at 95° C., 30 sec at 55° C. and 4 min at 72° C.; and 10 min at 72° C. The PCR product was purified on an agarose gel, eluted using the QIAquick® Gel Extraction Kit (Qiagen), digested with NdeI and BamHI and ligated into the similarly digested pET11a plasmid.

For construction of the GFTpsC-pET 11 a expression vector, two separated PCR were employed to generate the insert flanked with the NdeI and BamHI cohesive ends. A first PCR was performed in the same condition as described above, using the forward primer GFTpsCpETF1 (SEQ ID NO:62) 5'-TAATGGCACTTCAAGATTCAGAAGTTC-CTC-3'and the reverse primer GFTpsCpETR1 (SEQ ID NO:63) 5'-AAAAGGGAACAGGCTTCTCAAGCAATG-3'and a second PCR was performed using the forward primer GFTpsCpETF2 (shortened by AT at the 5'-end compared to GFTpsCpETF1) (SEQ ID NO:64) 5'-ATGGCACTTCAA-GATTCAGAAGTTCCTC-3'and the reverse primer GFTp-sCpETR2 (extended by GATC at the 5'-end compared to GFTpsCpETR1) (SEQ ID NO:65) 5'-GATCAAAAGG-GAACAGGCTTCTCAAGCAATG-3'. The two PCR products were purified as described above, combined, denatured by 5 mm boiling and cooled 5 mm on ice. The resulting cDNA was used directly for ligation into the pET11a plasmid.

Ligation products were initially transformed into JM109 *E. coli* cells and the constructs were verified by restriction digestion and DNA sequencing.

Sesquiterpene Synthases Expression.

For protein expression, the pET11a plasmids containing the sesquiterpene synthase cDNAs as well as the empty pET11a plasmid were transformed into the BL21 (DE3) *E. coli* cells (Novagen). Single colonies were used to inoculate 5 ml LB medium. After 5 to 6 hours incubation at 37° C., the cultures were transferred to a 20° C. incubator and left 1 h for equilibration. Expression of the protein was then induced by addition of 0.5 mM IPTG and the culture incubated over-night at 20° C.

The next day, the cells were collected by centrifugation, resuspended in 0.5 ml Extraction Buffer (50 mM MOPSO pH 7, 5 mM EDTA, 5 mM EDTA, 10% glycerol) and sonicated 3 times 30 s. The cell debris were sedimented by centrifugation 30 min at 18,000 g and the supernatant containing the soluble proteins was recovered. The expression of the sesquiterpene synthases was evaluated by separation of the protein extract on a SDS-PAGE (SDS-polyacrylamid gel electrophoresis) and staining with coomassie blue and comparison to protein extract obtained from cells transformed with the empty plasmid.

A distinct band with the expected calculated molecular weight was observed for all constructs and the band was not present in the soluble proteins from *E. coli* transformed with the empty plasmid.

Example 4

Enzyme Function Assay

The enzymatic assays were performed in sealed glass tubes using 50 to 100 μl of protein extract in a final volume of Extraction Buffer supplemented with 15 mM MgCl2 and 100 to 250 μM FPP (Sigma). The medium were overlaid with 1 ml pentane and the tubes incubated over-night at 30° C. The pentane phase, containing the sesquiterpenes, was recovered and the medium extract with a second volume of pentane. The combined pentane fractions were concentrated under nitrogen and analyzed by Gas Chromatography on a on a Hewlett-Packard 6890 Series GC system using a 0.25 mm inner diameter by 30 m SPB-1 (Supelco) capillary column. The carrier gas was He at constant flow of 1.6 ml/min. Injection was done at a split ratio of 2:1 with the injector temperature set at 200° C. and the oven programmed from 80° C. (0 min hold) at 7.5° C./min to 200° C. (0 min hold) followed by 20° C./min to 280° C. (2 min hold). Detection was made with a flame ionization detector. Compound identification was based on retention time identity with authentic standards when available. For confirmation of the products identities, samples were analyzed by combined capillary GC-MS using a Hewlett-Packard 6890 GC-quadrupole mass selective detector system, equipped with a 0.25 mm inner diameter by 30 m SPB-1 (Supelco) capillary column. The oven was programmed from 80° C. (0 min hold) to 280° C. at 7.5° C. at a constant flow of 1.5 ml/min He. The spectra were recorded at 70 eV with an electron multiplier voltage of 2200V.

Figure 3:
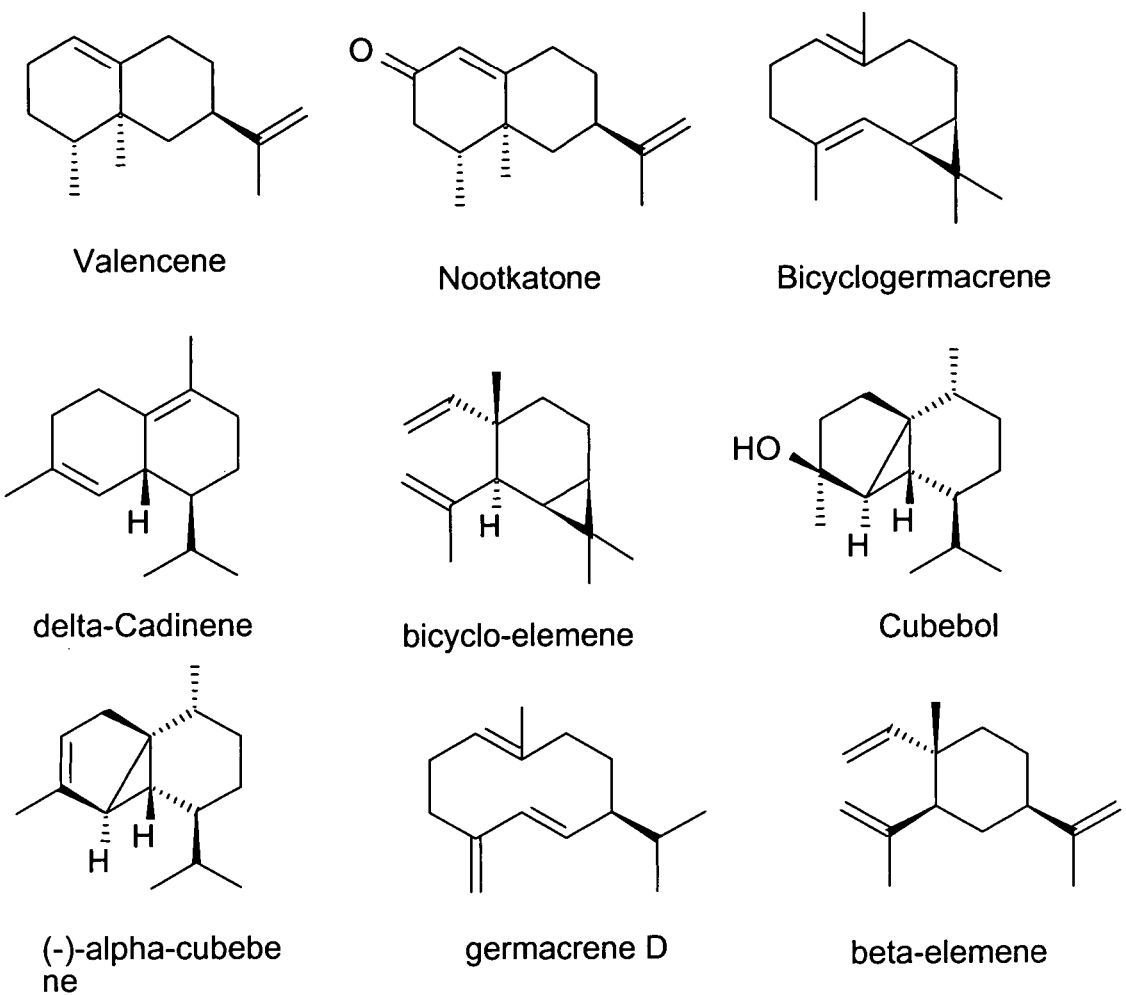
FIG. 3: Structure of example sesquiterpene compounds.
Figure 7:
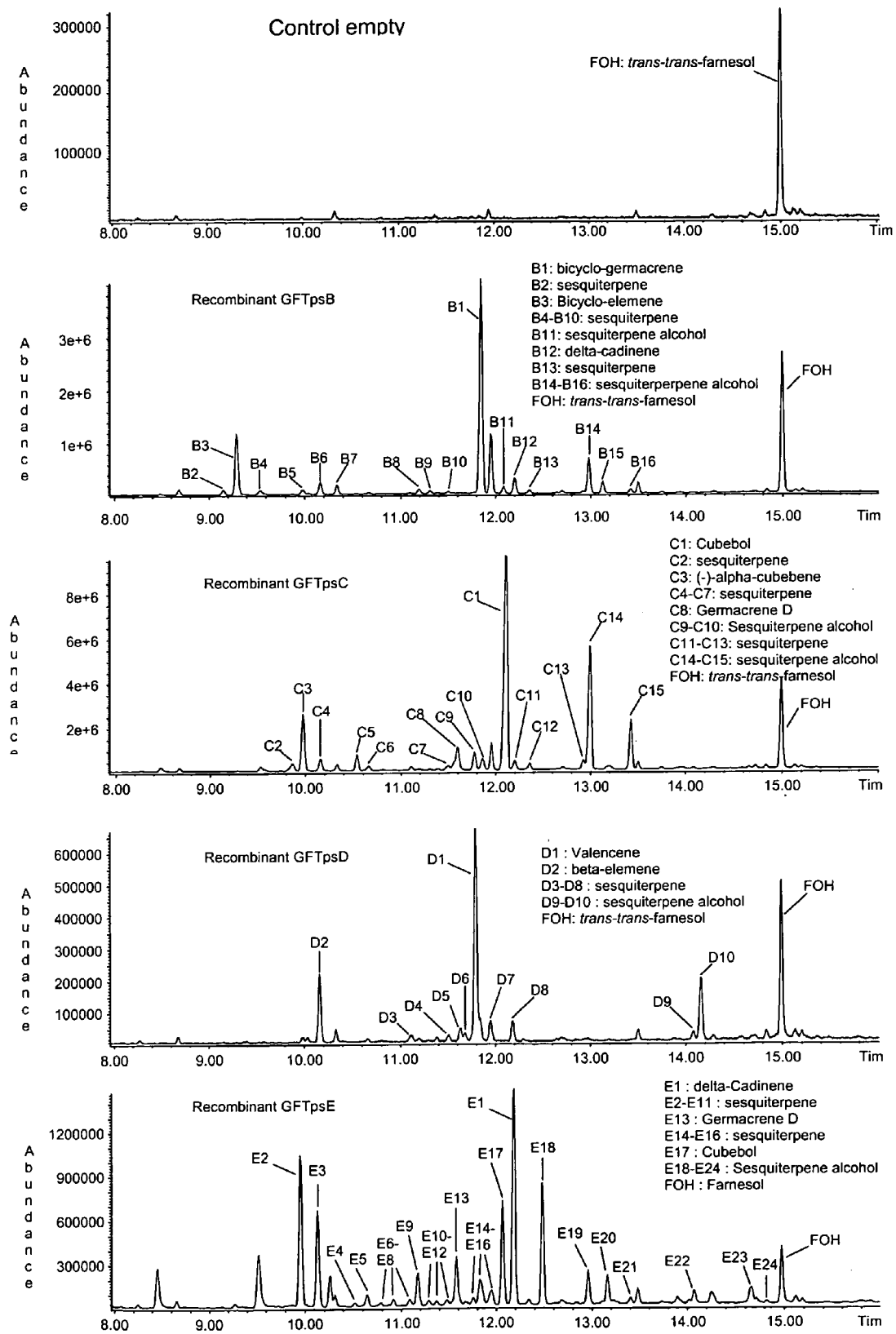
FIG. 7: GC profiles of sesquiterpenes produced by recombinant grapefruit sesquiterpene synthases.

The enzyme activity of the different recombinant enzymes were evaluated in this assay using the soluble protein fraction and farnesyl-diphosphate as substrate. Sesquiterpene synthase activity was obtained for all clones tested and the product formed were characterized by retention time and GC-MS (FIG. 7). The GFTpsB cDNA encoded a sesquiterpene synthase producing bicyclo-germacrene (FIG. 3) as major product and at least 15 minor sesquiterpene olefins or oxygenated sesquiterpenes such as delta-cadinene (FIG. 3) (byclo-elemene (FIG. 3), resulting from heat rearrangement of bicyclo-germacrene was also observed in the GC trace). The GFTpsC cDNA encoded a multiple product forming sesquiterpene synthase with a major product being identified as cubebol (FIG. 3). The enzyme also produced 3 other sesquiterpenes in a relative large proportion (−)-α-cubebene and 2 oxygenated sesquiterpenes, and in small amounts, at least 11 sesquiterpene olefins olefins or oxygenated sesquiterpenes. GFtpsD encoded a sesquiterpene synthase that produces Valencene as a major product. Ten other minor peaks were also identified as sesquiterpene olefins or alcohols. Among them, β-elemene is a heat degradation product of germacrene A. GFTpsE encoded a sesquiterpene synthase producing a complex mixture of sesquiterpene compounds with 6-cadinene (FIG. 3) being slightly the most abundant. Cubebol and Germacrene D (FIG. 3) were also identified in the mixture of products formed by GFTpsE.

The isolated sesquiterpene synthases demonstrated multiple product forming properties in the experiments described. For example, the cubebol synthase and the δ-cadinene produce 3 or 5 products in relatively large proportion. The bicyclogermacrene synthase produced a major sesquiterpene and several secondary products in trace amounts.

What is claimed is:

1. A method of making valencene which comprises
   A) contacting farnesyl-pyrophosphate with at least one polypeptide encoded by a nucleic acid chosen from:
   (a) a nucleic acid comprising the nucleotide sequence as set out in SEQ ID NO:9 or a nucleic acid sequence at least 95% identical to SEQ ID NO:9; and
   (b) a nucleic acid encoding the polypeptide as set out in SEQ ID NO:4 or a polypeptide sequence at least 95% identical to SEQ ID NO:4; and
   (c) a nucleic acid that hybridizes to the nucleic acid of (a) or (b) under high stringency conditions, wherein the polypeptide encoded by the nucleic acid is a valencene synthase.

2. The method of claim 1, which further comprises isolating valencene that is produced in A).

3. The method of claim 2, wherein valencene is isolated by at least one method chosen from extraction and distillation.

4. The method of claim 1, wherein the nucleic acid comprises the nucleotide sequence set out in SEQ ID NO:9.

5. The method of claim 1, wherein the nucleic acid encodes a polypeptide comprising SEQ ID NO:4.

6. The method of claim 1, wherein the nucleic acid hybridizes to the nucleic acid of (a) or (b) high moderate stringency conditions.

7. The method of claim 1, wherein the nucleic acid is isolated from a citrus.

8. The method of claim 1, wherein the valencene synthase is made by a process which comprises culturing a host modified to contain at least one of said nucleic acid sequences under conditions conducive to the production of the at least one valencene synthase.

9. The method of claim 8, wherein the host is a plant, a plant cell or a microorganism.

10. A method of making valencene which comprises contacting farnesyl-pyrophosphate with at least one polypeptide as set out in SEQ ID NO:4 or a polypeptide at least 95% identical to SEQ ID NO:4, wherein the polypeptide is a valencene synthase and is isolated from a citrus.

11. The method of claim 10, wherein the citrus is Citrus paradisi.

12. The method of claim 10, which further comprises isolating the produced valencene by at least one method chosen from extraction and distillation.

13. The method of claim 10, wherein the valencene synthase is made by a process which comprises culturing a host modified to contain at least one nucleic acid sequence encoding the polypeptide set out in SEQ ID NO:4 under conditions conducive to the production of the valencene synthase.

14. The method of claim 13, wherein the host is a plant, a plant cell or a microorganism.

* * * * *

UNITED STATES PATENT AND TRADEMARK OFFICE
CERTIFICATE OF CORRECTION

PATENT NO. : 7,273,735 B2 Page 1 of 1
APPLICATION NO. : 11/094607
DATED : September 25, 2007
INVENTOR(S) : Schalk et al.

It is certified that error appears in the above-identified patent and that said Letters Patent is hereby corrected as shown below:

Column 69:
Line 55 (claim 6, line 2), after "(b)", insert -- under --; and after "high", delete "moderate".

Signed and Sealed this

Fourth Day of December, 2007

JON W. DUDAS
*Director of the United States Patent and Trademark Office*

SEQUENCE LISTING

<160> NUMBER OF SEQ ID NOS: 65

<210> SEQ ID NO 1
<211> LENGTH: 556
<212> TYPE: PRT
<213> ORGANISM: Citrus paradisi

<400> SEQUENCE: 1

Met Ala Leu Gln Asp Ser Glu Val Pro Ser Ser Ile Leu Asn Ala Thr
1               5                   10                  15

Ala Gly Asn Arg Pro Thr Ala Ser Tyr His Pro Thr Leu Trp Gly Gly
            20                  25                  30

Lys Phe Leu Asp Tyr Ser Ser Val Asp Asp Ser Glu Ala Met Asp Ala

-continued

```
                35                  40                  45
Thr Ile Asp Gln Asp Glu Phe Glu Ala Leu Lys Gln Lys Ile Lys Asn
 50                  55                  60
Met Leu Ile Ser Pro Thr Asp Lys Ser Phe Gln Lys Leu Asn Leu Ile
 65                  70                  75                  80
Asp Ala Val Gln Arg Leu Gly Val Ala Tyr His Phe Glu Arg Glu Ile
                 85                  90                  95
Glu Asp Glu Leu Glu Lys Leu Ser Pro Asp Glu Tyr Asp Gly Asn Asp
                100                 105                 110
Val His Ser Val Ala Leu Arg Phe Arg Leu Leu Arg Gln Gln Gly Tyr
                115                 120                 125
Arg Ile Ser Cys Asp Ile Phe Gly Phe Lys Asp Asp Arg Gly Lys
                130                 135                 140
Phe Lys Val Ser Leu Ile Asn Asp Val Thr Gly Met Leu Ser Leu Tyr
145                 150                 155                 160
Glu Ala Ala His Leu Arg Ile Arg Gly Glu Asp Ile Leu Asp Glu Ala
                165                 170                 175
Leu Ala Phe Thr Thr Ser His Leu Glu Ser Met Val Thr Gln Val Ser
                180                 185                 190
Pro Gln Leu Ser Asp Glu Ile Leu His Ala Leu Asn Arg Pro Ile Arg
                195                 200                 205
Arg Gly Leu Pro Arg Leu Glu Ala Val Tyr Tyr Ile Asp Leu Tyr Ser
                210                 215                 220
Arg Asp Asp Ser Lys Asp Lys Ala Ile Leu Leu Lys Phe Ala Lys Leu
225                 230                 235                 240
Asp Phe Cys Met Leu Gln Val Ile His Arg Lys Glu Leu Ser Ile Ile
                245                 250                 255
Thr Glu Trp Trp Lys Asn Leu Asp Val Glu Ile Asn Leu Pro Tyr Ala
                260                 265                 270
Arg Asn Arg Val Val Glu Cys Tyr Phe Trp Ala Met Gly Val Tyr Phe
                275                 280                 285
Glu Pro Arg Tyr Ser Phe Ala Arg Lys Ile Leu Ser Lys Val Ile Ala
                290                 295                 300
Met Ala Ser Ile Leu Asp Asp Thr Tyr Asp Ala Tyr Gly Thr Leu Glu
305                 310                 315                 320
Glu Leu Glu Leu Phe Thr Asn Ala Ile Lys Arg Trp Asp Ile Ser Asn
                325                 330                 335
Ile Asp Val Leu Pro Lys Tyr Met Lys Leu Ile Tyr Gln Gly Leu Leu
                340                 345                 350
Asp Val Phe Gly Glu Ala Glu Glu Ile Ser Lys Glu Gly Gln Thr
                355                 360                 365
Tyr Cys Met Ser Tyr Val Ile Gln Ala Val Lys Lys Val Gln Ala
370                 375                 380
Tyr Phe Glu Glu Ala Lys Trp Cys Ser Glu Gly Tyr Phe Pro Lys Val
385                 390                 395                 400
Glu Glu Tyr Met Gln Val Ser Leu Val Thr Thr Cys Tyr His Met Leu
                405                 410                 415
Ala Thr Ala Ser Phe Leu Gly Met Gly Lys Ile Ala Asp Lys Gln Ala
                420                 425                 430
Phe Glu Trp Ile Ser Asn Tyr Pro Lys Thr Val Lys Ala Ser Gln Val
                435                 440                 445
Ile Cys Arg Leu Met Asp Asp Ile Val Ser His Glu Phe Glu Gln Lys
450                 455                 460
```

```
Arg Lys His Val Ala Ser Gly Ile Glu Cys Tyr Met Lys Gln His Gly
465                 470                 475                 480

Val Ser Asp Glu Glu Val Ile Lys Val Phe Arg Lys Gln Ile Ser Asn
                485                 490                 495

Gly Trp Lys Asp Val Asn Glu Gly Phe Met Lys Pro Thr Glu Val Ala
            500                 505                 510

Met Pro Leu Leu Glu Arg Ile Leu Asn Leu Ala Arg Val Ile Asp Val
            515                 520                 525

Ile Tyr Lys Asp Asp Asp Gly Tyr Thr Asn Ser Tyr Val Ile Lys Asp
            530                 535                 540

Tyr Ile Ala Thr Leu Leu Glu Lys Pro Val Pro Phe
545                 550                 555

<210> SEQ ID NO 2
<211> LENGTH: 562
<212> TYPE: PRT
<213> ORGANISM: Citrus paradisi

<400> SEQUENCE: 2

Met Ser Leu Glu Val Ser Ala Ser Pro Ala Lys Val Ile Gln Asn Ala
1               5                   10                  15

Gly Lys Asp Ser Thr Arg Arg Ser Ala Asn Tyr His Pro Ser Ile Trp
            20                  25                  30

Gly Asp His Phe Leu Gln Tyr Thr Cys Asp Thr Gln Glu Thr Asp Asp
            35                  40                  45

Gly Ser Asn Val Lys His Leu Glu Leu Lys Lys Glu Ile Arg Arg Met
        50                  55                  60

Leu Lys Ala Asp Asn Lys Pro Ser Arg Thr Leu Gln Leu Ile Asp Ala
65                  70                  75                  80

Ile Gln Arg Leu Gly Val Ser Tyr His Phe Glu Ser Glu Ile Asp Glu
                85                  90                  95

Ile Leu Gly Lys Met His Lys Ala Ser Gln Asp Ser Asp Leu Cys Asp
            100                 105                 110

Asn Glu Asn Asp Glu Leu Tyr Tyr Ile Ser Leu His Phe Arg Leu Leu
            115                 120                 125

Arg Gln Asn Gly Tyr Lys Ile Ser Ala Asp Val Phe Lys Lys Phe Lys
130                 135                 140

Asp Thr Asp Gly Asn Phe Lys Thr Ser Leu Ala Lys Asp Val Arg Gly
145                 150                 155                 160

Met Leu Ser Leu Tyr Glu Ala Thr His Leu Gly Val His Glu Glu Asp
                165                 170                 175

Ile Leu Asp Glu Ala Leu Ala Phe Thr Thr Ser His Leu Glu Ser Ile
            180                 185                 190

Ala Thr His Gln Ile Arg Ser Pro Leu Val Glu Gln Val Lys His Ala
            195                 200                 205

Leu Val Gln Pro Ile His Arg Gly Phe Gln Arg Leu Glu Ala Arg Gln
210                 215                 220

Tyr Ile Pro Ile Tyr Gln Glu Glu Ser Pro His Asn Glu Ala Leu Leu
225                 230                 235                 240

Thr Phe Ala Lys Leu Asp Phe Asn Lys Leu Gln Lys Pro His Gln Lys
                245                 250                 255

Glu Leu Gly Asp Ile Ser Arg Trp Trp Lys Glu Leu Asp Phe Ala His
            260                 265                 270

Lys Leu Pro Phe Ile Arg Asp Arg Val Ala Glu Cys Tyr Phe Trp Ile
```

```
                275                 280                 285
Leu Gly Val Tyr Phe Glu Pro Gln Tyr Ser Phe Ala Arg Arg Ile Leu
    290                 295                 300

Thr Lys Val Ile Ser Met Thr Ser Val Ile Asp Asp Ile Tyr Asp Val
305                 310                 315                 320

Tyr Gly Lys Ile Glu Glu Leu Glu Leu Phe Thr Ser Ala Ile Glu Arg
                325                 330                 335

Trp Asp Ile Ser Ala Ile Asp Gln Leu Pro Glu Tyr Met Lys Leu Cys
                340                 345                 350

Tyr Arg Ala Leu Leu Asp Val Phe Ser Glu Ala Glu Lys Asp Leu Ala
            355                 360                 365

Pro Gln Gly Lys Ser Tyr Arg Leu Tyr Ala Lys Glu Ala Met Lys
    370                 375                 380

Asn Met Val Lys Asn Tyr Phe Tyr Glu Ala Lys Trp Cys Leu Gln Asn
385                 390                 395                 400

Tyr Val Pro Thr Val Asp Glu Tyr Met Thr Val Ala Leu Val Thr Ser
                405                 410                 415

Gly Ser Pro Met Leu Ser Thr Thr Ser Phe Val Gly Met Gly Asp Ile
                420                 425                 430

Val Thr Lys Glu Ser Phe Glu Trp Leu Phe Ser Asn Pro Arg Phe Ile
            435                 440                 445

Arg Ala Ser Ser Ile Val Cys Arg Leu Met Asp Asp Ile Val Ser His
    450                 455                 460

Lys Phe Glu Gln Ser Arg Gly His Val Ala Ser Val Glu Cys Tyr
465                 470                 475                 480

Met Lys Gln His Gly Ala Thr Glu Glu Ala Cys Asn Glu Phe Arg
                485                 490                 495

Lys Gln Val Ser Asn Ala Trp Lys Asp Ile Asn Glu Asp Cys Leu Arg
                500                 505                 510

Pro Thr Val Val Pro Met Pro Leu Met Arg Ile Leu Asn Leu Thr
            515                 520                 525

Arg Val Ile Asp Val Ile Tyr Lys Tyr Glu Asp Gly Tyr Thr His Ser
    530                 535                 540

Ala Val Val Leu Lys Asp Phe Val Ala Ser Leu Phe Ile Asn Pro Val
545                 550                 555                 560

Pro Ile

<210> SEQ ID NO 3
<211> LENGTH: 555
<212> TYPE: PRT
<213> ORGANISM: Citrus paradisi

<400> SEQUENCE: 3

Met Ser Ala Gln Val Leu Ala Thr Val Ser Ser Thr Glu Lys Thr
1               5                   10                  15

Val Arg Pro Ile Ala Gly Phe His Pro Asn Leu Trp Gly Asp Tyr Phe
                20                  25                  30

Leu Thr Leu Ala Ser Asp Cys Lys Thr Asp Thr Thr His Gln Glu
            35                  40                  45

Glu Tyr Glu Ala Leu Lys Gln Glu Val Arg Ser Met Ile Thr Ala Thr
    50                  55                  60

Ala Asp Thr Pro Ala Gln Lys Leu Gln Leu Val Asp Ala Val Gln Arg
65                  70                  75                  80

Leu Gly Val Ala Tyr His Phe Glu Gln Glu Ile Glu Asp Ala Met Glu
```

```
                        85                  90                  95
Lys Ile Tyr His Asp Asp Phe Asp Asn Asn Asp Asp Val Asp Leu Tyr
                100                 105                 110
Thr Val Ser Leu Arg Phe Arg Leu Leu Arg Gln Gln Gly Phe Lys Val
                115                 120                 125
Pro Cys Asp Val Phe Ala Lys Phe Lys Asp Asp Glu Gly Lys Phe Lys
            130                 135                 140
Ala Ser Leu Val Arg Asp Val His Gly Ile Leu Ser Leu Tyr Glu Ala
145                 150                 155                 160
Gly His Leu Ala Ile Arg Gly Glu Gly Ile Leu Asp Glu Ala Ile Ala
                165                 170                 175
Phe Thr Arg Thr His Leu Gln Ser Met Val Ser Gln Asp Val Cys Pro
                180                 185                 190
Asn Asn Leu Ala Glu Gln Ile Asn His Thr Leu Asp Cys Pro Leu Arg
            195                 200                 205
Arg Ala Leu Pro Arg Val Glu Thr Arg Phe Phe Leu Ser Val Tyr Pro
        210                 215                 220
Arg Asp Asp Lys His Asp Lys Thr Leu Leu Lys Phe Ser Lys Leu Asp
225                 230                 235                 240
Phe Asn Leu Val Gln Arg Ile His Gln Lys Glu Leu Ser Ala Ile Thr
                245                 250                 255
Arg Trp Trp Lys Asp Leu Asp Phe Thr Thr Lys Leu Pro Tyr Ala Arg
                260                 265                 270
Asp Arg Ile Val Glu Leu Tyr Phe Trp Ile Val Gly Thr Tyr Phe Glu
            275                 280                 285
Pro Lys Tyr Thr Leu Ala Arg Lys Ile Met Thr Lys Thr Ile Tyr Thr
        290                 295                 300
Ala Ser Ile Ile Asp Asp Thr Phe Asp Ala Tyr Gly Phe Phe Glu Glu
305                 310                 315                 320
Leu Lys Leu Phe Ala Glu Ala Val Gln Arg Trp Asp Ile Gly Ala Met
                325                 330                 335
Asp Ile Leu Pro Glu Tyr Met Lys Val Leu Tyr Lys Ala Leu Leu Asp
            340                 345                 350
Thr Phe Asn Glu Ile Glu Gln Asp Leu Ala Lys Glu Gly Arg Ser Ser
        355                 360                 365
Tyr Leu Pro Tyr Gly Lys Glu Lys Met Gln Glu Leu Val Gln Met Tyr
    370                 375                 380
Phe Val Gln Ala Lys Trp Phe Ser Glu Gly Tyr Val Pro Thr Trp Asp
385                 390                 395                 400
Glu Tyr Tyr Pro Val Gly Leu Val Ser Cys Gly Tyr Phe Met Leu Ala
                405                 410                 415
Thr Asn Ser Phe Leu Gly Met Cys Asp Val Ala Asn Glu Glu Ala Phe
            420                 425                 430
Glu Trp Ile Ser Lys Asp Pro Lys Ile Ser Thr Ala Ser Ser Val Ile
        435                 440                 445
Cys Arg Leu Arg Asn Asp Ile Val Ser His Gln Phe Glu Gln Lys Arg
    450                 455                 460
Gly His Ile Ala Ser Gly Phe Glu Cys Tyr Ile Lys Gln Tyr Gly Val
465                 470                 475                 480
Ser Glu Glu Glu Val Val Thr Val Phe Thr Glu Glu Val Glu Asn Ala
                485                 490                 495
Trp Lys Asp Met Asn Glu Glu Phe Leu Lys Pro Thr Ala Phe Pro Val
            500                 505                 510
```

```
Ala Leu Ile Glu Arg Pro Phe Asn Ile Ala Arg Val Ile Glu Phe Leu
            515                 520                 525

Asn Lys Lys Gly Asp Trp Tyr Thr His Ser His Ala Ile Lys Asp Gln
            530                 535                 540

Ile Ala Ala Val Leu Arg Asp Pro Val Thr Ile
545                 550                 555

<210> SEQ ID NO 4
<211> LENGTH: 548
<212> TYPE: PRT
<213> ORGANISM: Citrus paradisi

<400> SEQUENCE: 4

Met Ser Ser Gly Glu Thr Phe Arg Pro Thr Ala Asp Phe His Pro Ser
1               5                   10                  15

Leu Trp Arg Asn His Phe Leu Lys Gly Ala Ser Asp Phe Lys Thr Val
            20                  25                  30

Asp His Thr Ala Thr Gln Glu Arg His Glu Ala Leu Lys Glu Glu Val
            35                  40                  45

Arg Arg Met Ile Thr Asp Ala Glu Asp Lys Pro Val Gln Lys Leu Arg
50                  55                  60

Leu Ile Asp Glu Val Gln Arg Leu Gly Val Ala Tyr His Phe Glu Lys
65                  70                  75                  80

Glu Ile Glu Asp Ala Ile Gln Lys Leu Cys Pro Ile Tyr Ile Asp Ser
                85                  90                  95

Asn Arg Ala Asp Leu His Thr Val Ser Leu His Phe Arg Leu Leu Arg
            100                 105                 110

Gln Gln Gly Ile Lys Ile Ser Cys Asp Val Phe Glu Lys Phe Lys Asp
            115                 120                 125

Asp Glu Gly Arg Phe Lys Ser Ser Leu Ile Asn Asp Val Gln Gly Met
130                 135                 140

Leu Ser Leu Tyr Glu Ala Ala Tyr Met Ala Val Arg Gly Glu His Ile
145                 150                 155                 160

Leu Asp Glu Ala Ile Ala Phe Thr Thr Thr His Leu Lys Ser Leu Val
                165                 170                 175

Ala Gln Asp His Val Thr Pro Lys Leu Ala Glu Gln Ile Asn His Ala
            180                 185                 190

Leu Tyr Arg Pro Leu Arg Lys Thr Leu Pro Arg Leu Glu Ala Arg Tyr
            195                 200                 205

Phe Met Ser Met Ile Asn Ser Thr Ser Asp His Leu Tyr Asn Lys Thr
210                 215                 220

Leu Leu Asn Phe Ala Lys Leu Asp Phe Asn Ile Leu Leu Glu Leu His
225                 230                 235                 240

Lys Glu Glu Leu Asn Glu Leu Thr Lys Trp Trp Lys Asp Leu Asp Phe
                245                 250                 255

Thr Thr Lys Leu Pro Tyr Ala Arg Asp Arg Leu Val Glu Leu Tyr Phe
            260                 265                 270

Trp Asp Leu Gly Thr Tyr Phe Glu Pro Gln Tyr Ala Phe Gly Arg Lys
            275                 280                 285

Ile Met Thr Gln Leu Asn Tyr Ile Leu Ser Ile Asp Asp Thr Tyr
290                 295                 300

Asp Ala Tyr Gly Thr Leu Glu Glu Leu Ser Leu Phe Thr Glu Ala Val
305                 310                 315                 320

Gln Arg Trp Asn Ile Glu Ala Val Asp Met Leu Pro Glu Tyr Met Lys
```

```
                    325                 330                 335
Leu Ile Tyr Arg Thr Leu Leu Asp Ala Phe Asn Glu Ile Glu Glu Asp
                340                 345                 350

Met Ala Lys Gln Gly Arg Ser His Cys Val Arg Tyr Ala Lys Glu Glu
            355                 360                 365

Asn Gln Lys Val Ile Gly Ala Tyr Ser Val Gln Ala Lys Trp Phe Ser
        370                 375                 380

Glu Gly Tyr Val Pro Thr Ile Glu Glu Tyr Met Pro Ile Ala Leu Thr
385                 390                 395                 400

Ser Cys Ala Tyr Thr Phe Val Ile Thr Asn Ser Phe Leu Gly Met Gly
                405                 410                 415

Asp Phe Ala Thr Lys Glu Val Phe Glu Trp Ile Ser Asn Asn Pro Lys
            420                 425                 430

Val Val Lys Ala Ala Ser Val Ile Cys Arg Leu Met Asp Asp Met Gln
        435                 440                 445

Gly His Glu Phe Glu Gln Lys Arg Gly His Val Ala Ser Ala Ile Glu
    450                 455                 460

Cys Tyr Thr Lys Gln His Gly Val Ser Lys Glu Ala Ile Lys Met
465                 470                 475                 480

Phe Glu Glu Val Ala Asn Ala Trp Lys Asp Ile Asn Glu Glu Leu
                485                 490                 495

Met Met Lys Pro Thr Val Val Ala Arg Pro Leu Leu Gly Thr Ile Leu
            500                 505                 510

Asn Leu Ala Arg Ala Ile Asp Phe Ile Tyr Lys Glu Asp Asp Gly Tyr
        515                 520                 525

Thr His Ser Tyr Leu Ile Lys Asp Gln Ile Ala Ser Val Leu Gly Asp
    530                 535                 540

His Val Pro Phe
545

<210> SEQ ID NO 5
<211> LENGTH: 548
<212> TYPE: PRT
<213> ORGANISM: Citrus paradisi

<400> SEQUENCE: 5

Met Ser Ser Gly Glu Thr Phe Arg Pro Thr Ala Asp Phe His Pro Ser
1               5                   10                  15

Leu Trp Arg Asn His Phe Leu Lys Gly Ala Ser Asp Phe Lys Thr Val
            20                  25                  30

Asp His Thr Ala Thr Gln Glu Arg His Glu Ala Leu Lys Glu Glu Val
        35                  40                  45

Arg Arg Met Ile Thr Asp Ala Glu Asp Lys Pro Val Gln Lys Leu Arg
    50                  55                  60

Leu Ile Asp Glu Val Gln Arg Leu Gly Val Ala Tyr His Phe Glu Lys
65                  70                  75                  80

Glu Ile Glu Asp Ala Ile Gln Lys Leu Cys Pro Asn Tyr Ile His Ser
                85                  90                  95

Asn Ser Pro Asp Leu His Thr Val Ser Leu His Phe Arg Leu Leu Arg
            100                 105                 110

Gln Gln Gly Ile Lys Ile Ser Cys Asp Val Phe Glu Lys Phe Lys Asp
        115                 120                 125

Asp Glu Gly Arg Phe Lys Ser Ser Leu Ile Asn Asp Val Gln Gly Met
    130                 135                 140
```

-continued

```
Leu Ser Leu Tyr Glu Ala Ala Tyr Met Ala Val Arg Gly Glu His Ile
145                 150                 155                 160

Leu Asp Glu Ala Ile Ala Phe Thr Thr Thr His Leu Lys Ser Leu Val
                165                 170                 175

Ala Gln Asp His Val Thr Pro Lys Leu Ala Glu Gln Ile Asn His Ala
            180                 185                 190

Leu Tyr Arg Pro Leu Arg Lys Thr Leu Pro Arg Leu Glu Ala Arg Tyr
        195                 200                 205

Phe Met Ser Met Ile Asn Ser Thr Ser Asp His Leu Tyr Asn Lys Thr
    210                 215                 220

Leu Leu Asn Phe Ala Lys Leu Asp Phe Asn Ile Leu Glu Leu His
225                 230                 235                 240

Lys Glu Glu Leu Asn Glu Leu Thr Lys Trp Trp Lys Asp Leu Asp Phe
                245                 250                 255

Thr Thr Lys Leu Pro Tyr Ala Arg Asp Arg Leu Val Glu Leu Tyr Phe
                260                 265                 270

Trp Asp Leu Gly Thr Tyr Phe Glu Pro Gln Tyr Ala Phe Gly Arg Lys
            275                 280                 285

Ile Met Thr Gln Leu Asn Tyr Ile Leu Ser Ile Ile Asp Asp Thr Tyr
        290                 295                 300

Asp Ala Tyr Gly Thr Leu Glu Glu Leu Ser Leu Phe Thr Glu Ala Val
305                 310                 315                 320

Gln Arg Trp Asn Ile Glu Ala Val Asp Met Leu Pro Glu Tyr Met Lys
                325                 330                 335

Leu Ile Tyr Arg Thr Leu Leu Asp Ala Phe Asn Glu Ile Glu Glu Asp
            340                 345                 350

Met Ala Lys Gln Gly Arg Ser His Cys Val Arg Tyr Ala Lys Glu Glu
355                 360                 365

Asn Gln Lys Val Ile Gly Ala Tyr Ser Val Gln Ala Lys Trp Phe Ser
    370                 375                 380

Glu Gly Tyr Val Pro Thr Ile Glu Glu Tyr Met Pro Ile Ala Leu Thr
385                 390                 395                 400

Ser Cys Ala Tyr Thr Phe Val Ile Thr Asn Ser Phe Leu Gly Met Gly
                405                 410                 415

Asp Phe Ala Thr Lys Glu Val Phe Glu Trp Ile Ser Asn Asn Pro Lys
            420                 425                 430

Val Val Lys Ala Ala Ser Val Ile Cys Arg Leu Met Asp Asp Met Gln
        435                 440                 445

Gly His Glu Phe Glu Gln Lys Arg Gly His Val Ala Ser Ala Ile Glu
    450                 455                 460

Cys Tyr Thr Lys Gln His Gly Val Ser Lys Glu Glu Ala Ile Lys Met
465                 470                 475                 480

Phe Glu Glu Glu Val Ala Asn Ala Trp Lys Asp Ile Asn Glu Glu Leu
                485                 490                 495

Met Met Lys Pro Thr Val Val Ala Arg Pro Leu Leu Gly Thr Ile Leu
                500                 505                 510

Asn Leu Ala Arg Ala Ile Asp Phe Ile Tyr Lys Glu Asp Asp Gly Tyr
            515                 520                 525

Thr His Ser Tyr Leu Ile Lys Asp Gln Ile Ala Ser Val Leu Gly Asp
    530                 535                 540

His Val Pro Phe
545
```

<210> SEQ ID NO 6
<211> LENGTH: 1671
<212> TYPE: DNA
<213> ORGANISM: Citrus X paradisi

<400> SEQUENCE: 6

| | |
|---|---|
| atggcacttc aagattcaga gttccttct tccattctga atgctacagc cggcaaccgt | 60 |
| cccacagcta gttatcatcc caccctctgg gggggaaaat tccttgacta ttcttctgtt | 120 |
| gacgactctg aggcaatgga tgccacaatt gatcaagacg aatttgaagc acttaagcaa | 180 |
| aaaataaaga acatgttaat ctcaccaacc gataagtctt ttcaaaaatt gaacttgatt | 240 |
| gatgccgtcc aacgcttagg agtggcttac catttgaga gggagataga agatgaacta | 300 |
| gaaaaactat ctcctgatga gtatgatggc aacgatgtac actccgttgc tcttcgattt | 360 |
| cggttactca gacaacaagg atatcgcata tcatgcgata ttttggcgg tttcaaagat | 420 |
| gatcgaggaa agttcaaggt atccttaatt aatgatgtga ccggcatgct aagtttgtat | 480 |
| gaggctgcac atcttcgcat tcgcggggaa gatatcctgg atgaagccct agctttcact | 540 |
| acttctcacc tggaatcaat ggttactcaa gtaagccctc agctttctga tgaaatactt | 600 |
| catgccttga ataggccaat ccgcagaggc ttaccaaggc tggaggcagt ctattacatc | 660 |
| gatctctact cacgagatga ttcaaaggat aaagcaatat tactaaagtt tgcaaaacta | 720 |
| gatttttgca tgcttcaagt aattcaccgt aaggagttaa gtatcatcac agagtggtgg | 780 |
| aaaaatttag atgttgaaat aaatctccca tatgctagaa acagagttgt agaatgctat | 840 |
| ttttgggcaa tgggagtgta ttttgagcct cgatactcct ttgcaagaaa gatattgtcc | 900 |
| aaagtaattg caatggcatc catttagat gatacctacg acgcctatgg cacacttgaa | 960 |
| gaacttgagc tctttacaaa tgctatcaaa aggtgggata ttagcaacat agatgtactt | 1020 |
| ccgaagtaca tgaaactgat ttatcaagga ctcttggatg ttttggtga agctgaggag | 1080 |
| gaaatctcaa aggaaggaca gacatattgc atgtcatatg tcatacaagc ggtgaagaaa | 1140 |
| gtagtccaag cctactttga ggaagccaag tggtgcagtg aaggttattt tccaaaagtg | 1200 |
| gaggagtata tgcaagtttc acttgtgaca acttgctatc atatgctggc aacggcttct | 1260 |
| tttcttggca tgggaaagat tgctgataag caggcctttg aatggatctc caattaccct | 1320 |
| aaaactgtga agcctccca gttatttgc agacttatgg atgatatagt gtctcacgag | 1380 |
| tttgaacaaa aagaaagca tgttgcctcg ggtattgaat gttacatgaa gcagcatggc | 1440 |
| gtctctgatg aagaggtaat taagtattc cgcaaacaaa tatcaaatgg atggaaagat | 1500 |
| gtaaatgaag gattcatgaa gccaacagaa gtggcaatgc ctctccttga gcgcattctc | 1560 |
| aatcttgcac gagtgataga tgttatttac aaggatgatg atggctacac caactcttat | 1620 |
| gtgatcaaag actacatcgc cacattgctt gagaagcctg ttccctttg a | 1671 |

<210> SEQ ID NO 7
<211> LENGTH: 1689
<212> TYPE: DNA
<213> ORGANISM: Citrus paradisi

<400> SEQUENCE: 7

| | |
|---|---|
| atgtctttgg aagtttcagc ctctcctgct aaagttatcc aaaatgctgg gaaagattct | 60 |
| actcgtcgct ctgcaaatta tcatccaagc atctgggggg atcatttcct tcaatatact | 120 |
| tgtgacaccc aggaaactga tgatggcagc aatgtaaagc atctagagct gaagaaagaa | 180 |
| attagaagaa tgctaaaagc tgataacaag ccttcacgta cacttcaatt gattgatgca | 240 |

```
attcagcgtt taggagtgtc ttaccatttt gaaagtgaga ttgatgaaat attgggaaag      300
atgcataagg cttcccaaga ctctgatctt tgtgataatg aaaatgatga gctctattat      360
atctctcttc attttcgatt acttagacaa aatggctata aaatttccgc tgatgtgttc      420
aaaaagttca aagacacgga tgggaacttt aaaacatctc ttgcgaaaga tgttcgagga      480
atgttaagct tgtatgaagc tacgcatctc ggggtacatg aagaagatat actagatgaa      540
gcgcttgctt tcaccactag tcacctagag tcaatagcga ctcatcaaat caggtctcca      600
cttgttgaac aagtcaaaca tgccttagtt cagcctatcc acaggggctt ccaaaggctt      660
gaggcaagac agtacattcc tatctatcaa gaagaatctc cccacaatga agctctgtta      720
acttttgcaa agttagattt taacaaattg caaaagcctc accagaagga actcggtgat      780
atttcaaggt ggtggaaaga attagacttt gcacataagc tacctttcat aagagataga      840
gttgcggagt gctacttttg gatattagga gtgtatttcg agccccaata ttcatttgca      900
agaagaatat tgacgaaagt gatctccatg acttctgtta ttgatgatat ctatgatgtg      960
tatggcaaaa ttgaagaact tgagcttttt acttcagcta ttgagaggtg ggatatcagt     1020
gccatagatc aacttcctga gtatatgaaa ttgtgttata gggcccttct tgatgttttt     1080
agtgaagcag agaaggattt ggccccccaa ggaaaatcat accgcctcta ttatgcaaaa     1140
gaagcgatga gaatatggt taagaattac ttctacgaag ctaaatggtg tcttcagaat     1200
tatgtaccta cagtggatga gtacatgacg gttgcattag ttacatctgg ctccccaatg     1260
ttgtcaacca catcctttgt tggcatggga gacattgtaa ctaaagaatc tttttgagtgg     1320 ttattcagca atcctagatt tattagggct tcttctatag tttgccgact catggatgac     1380
atagtgtcac acaagtttga acaaagcaga gggcacgttg cctcaagcgt tgagtgttac     1440
atgaaacaac atggagcaac agaagaggaa gcatgcaatg agtttcggaa acaagtttca     1500
aatgcctgga aggatataaa tgaggactgc ctacgcccaa cggttgtgcc aatgccactt     1560
ctgatgcgaa ttctcaatct tacacgcgtt atagatgtca tttacaagta tgaagatggc     1620
tacactcatt ccgcagttgt gctgaaagat tttgttgctt ctttgtttat taatcctgtg     1680
ccgatatga                                                             1689

<210> SEQ ID NO 8
<211> LENGTH: 1668
<212> TYPE: DNA
<213> ORGANISM: Citrus paradisi

<400> SEQUENCE: 8
atgtccgctc aagttctagc aacggtttcc agtcgacag aaaaaactgt tcgtcccatt       60
gctggtttcc atcctaactt atggggagac tatttcctga ccctcgcttc tgattgcaag     120
acagatgata ctacgcacca agaggaatac gaagcgctga gcaagaagt cagaagcatg     180 ataacggcta cggcagatac acctgcccag aagttgcaat ggttgatgc agtccaacga     240 ttgggtgtgg cctatcactt cgaacaggag atagaagatg caatggaaaa gatttatcac     300
gatgactttg ataataacga tgatgtcgat ctctacactg tttctcttcg ttttcgactg     360
cttaggcagc aagggattaa ggttccgtgt gatgtgttcg cgaagttcaa agatgatgaa     420
ggtaaattca aggcatcatt ggtgcgggat gttcatggca ttctaagttt gtatgaggca     480
ggacacttgg ccattcgcgg agaagggata ttagatgaag ccattgcttt cactagaact     540
caccttcagt caatggtatc tcaggatgta tgccctaata atcttgctga acaaattaat     600
catactctcg actgtcctct ccgcagagcc cttccaagag tggagacaag atttttcttg     660
```

-continued

```
tcggtctatc caagagatga taaacacgat aaaactttgt taaagttttc aaagttagac      720
tttaaccttg tgcaaagaat acatcagaag gaattaagtg ccatcacacg gtggtggaaa      780
gatttagact tcactacaaa gctaccttat gcaagagaca gaatcgtaga gttgtatttt      840
tggattgtag ggacgtattt tgaaccaaag tacactttag caagaaaaat aatgaccaaa      900
acaatttaca cggcatctat catagatgac actttcgacg cttatggttt ctttgaagag      960
ctcaaactct tgcagaagc agtccagagg tgggacattg gagccatgga tatacttcca     1020
gaatacatga aagtgcttta taaggcccctt ttagatactt tcaatgaaat tgagcaagac     1080
ttggccaagg aaggaagatc gtcctactta ccttatgcca agaaaagat gcaagagctt      1140
gttcaaatgt actttgttca agccaagtgg ttcagtgaag gttatgttcc gacatgggac     1200
gaatattatc cggttggact tgtaagttgc ggctacttca tgcttgcgac aaactccttc     1260
cttggcatgt gtgatgttgc aaacgaggaa gcttttgaat ggatatccaa ggaccctaag     1320
atttcaacag cgtcatcagt tatctgcaga cttaggaatg acattgtttc ccaccagttt     1380
gaacagaaga gaggacatat tgcctcagga tttgaatgct acattaagca gtatggtgtt     1440
tcagaagaag aggtagttac agtttttact gaagaagttg agaatgcatg gaaagatatg     1500
aatgaggaat tcctgaaacc aactgctttt cctgtggctt tgattgagag accttttcaat    1560
atcgcacgtg tgattgaatt tctaaacaag aagggtgatt ggtacactca ttctcatgcg     1620
attaaagacc agattgccgc agtgctcaga gaccctgtta ccatctga                 1668
```

<210> SEQ ID NO 9
<211> LENGTH: 1647
<212> TYPE: DNA
<213> ORGANISM: Citrus paradisi

<400> SEQUENCE: 9

```
atgtcgtctg gagaaacatt tcgtcctact gcagatttcc atcctagttt atggagaaac       60
catttcctca aggtgcttc tgatttcaag acagttgatc atactgcaac tcaagaacga      120
cacgaggcac tgaaagaaga ggtaaggaga atgataacag atgctgaaga taagcctgtt      180
cagaagttac gcttgattga tgaagtacaa cgcctggggg tggcttatca ctttgagaaa      240
gaaatagaag atgcaataca aaaattatgt ccaatctata ttgacagtaa tagagctgat      300
ctccacaccg tttcccttca ttttcgattg cttaggcagc aaggaatcaa gatttcatgt      360
gatgtgtttg agaagttcaa agatgatgag ggtagattca agtcatcgtt gataaacgat      420
gttcaaggga tgttaagttt gtacgaggca gcatacatgg cagttcgcgg agaacatata      480
ttagatgaag ccattgcttt cactaccact cacctgaagt cattggtagc tcaggatcat      540
gtaacccta gcttgcgga acagataaat catgctttat accgtcctct tcgtaaaacc       600
ctaccaagat tagaggcgag gtattttatg tccatgatca attcaacaag tgatcattta      660
tacaataaaa ctctgctgaa ttttgcaaag ttagatttta acatattgct agagctgcac      720
aaggaggaac tcaatgaatt aacaaagtgg tggaaagatt tagacttcac tacaaaacta      780
ccttatgcaa gagacagatt agtggagtta tatttttggg atttagggac atacttcgag      840
cctcaatatg catttgggag aaagataatg acccaattaa attacatatt atccatcata      900
gatgatactt atgatgcgta tggtacactt gaagaactca gcctctttac tgaagcagtt      960
caaagatgga atattgaggc cgtagatatg cttccagaat acatgaaatt gatttacagg     1020
acactcttag atgcttttaa tgaaattgag gaagatatgg ccaagcaagg aagatcacac     1080
```

-continued

```
tgcgtacgtt atgcaaaaga ggagaatcaa aaagtaattg gagcatactc tgttcaagcc    1140
aaatggttca gtgaaggtta cgttccaaca attgaggagt atatgcctat tgcactaaca    1200
agttgtgctt acacattcgt cataacaaat tccttccttg gcatgggtga ttttgcaact    1260
aaagaggttt ttgaatggat ctccaataac cctaaggttg taaaagcagc atcagttatc    1320
tgcagactca tggatgacat gcaaggtcat gagtttgagc agaagagagg acatgttgcg    1380
tcagctattg aatgttacac gaagcagcat ggtgtctcta aggaagaggc aattaaaatg    1440
tttgaagaag aagttgcaaa tgcatggaaa gatattaacg aggagttgat gatgaagcca    1500
accgtcgttg cccgaccact gctcgggacg attcttaatc ttgctcgtgc aattgatttt    1560
atttacaaag aggacgacgg ctatacgcat tcttacctaa ttaaagatca aattgcttct    1620
gtgctaggag accacgttcc attttga                                        1647
```

<210> SEQ ID NO 10
<211> LENGTH: 1647
<212> TYPE: DNA
<213> ORGANISM: Citrus paradisi

<400> SEQUENCE: 10

```
atgtcgtctg gagaaacatt tcgtcctact gcagatttcc atcctagttt atggagaaac      60
catttcctca aggtgcttc tgatttcaag cagttgatc atactgcaac tcaagaacga     120
cacgaggcac tgaaagaaga ggtaaggaga atgataacag atgctgaaga taagcctgtt     180
cagaagttac gcttgattga tgaagtacaa cgcctggggg tggcttatca ctttgagaaa     240
gaaatagaag atgcaataca aaaattatgt ccaaactata ttcacagtaa tagccctgat     300
cttcacaccg tttctcttca ttttcgattg cttaggcagc aaggaatcaa gatttcatgt     360
gatgtgtttg agaagttcaa agatgatgag ggtagattca agtcatcgtt gataaacgat     420
gttcaaggga tgttaagttt gtacgaggca gcatacatgg cagttcgcgg agaacatata     480
ttagatgaag ccattgcttt cactaccact cacctgaagt cattggtagc tcaggatcat     540
gtaaccccta agcttgcgga acagataaat catgctttat accgtcctct tcgtaaaacc     600
ctaccaagat tagaggcgag gtattttatg tccatgatca attcaacaag tgatcattta     660
tacaataaaa ctctgctgaa ttttgcaaag ttagatttta acatattgct agagctgcac     720
aaggaggaac tcaatgaatt aacaaagtgg tggaaagatt tagacttcac tacaaaacta     780
ccttatgcaa gagacagatt agtggagtta tattttgggg atttagggac atacttcgag     840
cctcaatatg catttgggag aaagataatg acccaattaa attacatatt atccatcata     900
gatgatactt atgatgcgta tggtacactt gaagaactca gcctctttac tgaagcagtt     960
caaagatgga atattgaggc cgtagatatg cttccagaat acatgaaatt gatttacagg    1020
acactcttag atgcttttaa tgaaattgag gaagatatgg ccaagcaagg aagatcacac    1080
tgcgtacgtt atgcaaaaga ggagaatcaa aaagtaattg gagcatactc tgttcaagcc    1140
aaatggttca gtgaaggtta cgttccaaca attgaggagt atatgcctat tgcactaaca    1200
agttgtgctt acacattcgt cataacaaat tccttccttg gcatgggtga ttttgcaact    1260
aaagaggttt ttgaatggat ctccaataac cctaaggttg taaaagcagc atcagttatc    1320
tgcagactca tggatgacat gcaaggtcat gagtttgagc agaagagagg acatgttgcg    1380
tcagctattg aatgttacac gaagcagcat ggtgtctcta aggaagaggc aattaaaatg    1440
tttgaagaag aagttgcaaa tgcatggaaa gatattaacg aggagttgat gatgaagcca    1500
accgtcgttg cccgaccact gctcgggacg attcttaatc ttgctcgtgc aattgatttt    1560
```

```
atttacaaag aggacgacgg ctatacgcat tcttacctaa ttaaagatca aattgcttct    1620
gtgctaggag accacgttcc attttga                                        1647
```

<210> SEQ ID NO 11
<211> LENGTH: 74
<212> TYPE: PRT
<213> ORGANISM: Lycopersicon esculentum

<400> SEQUENCE: 11

Phe His Gln Arg Glu Leu Ser Asp Leu Thr Arg Trp Trp Lys Asp Leu
1               5                   10                  15

Asp Phe Ala Asn Lys Tyr Pro Tyr Ala Arg Asp Arg Leu Val Glu Cys
            20                  25                  30

Tyr Phe Trp Ile Leu Gly Val Tyr Phe Glu Pro Lys Tyr Ser Arg Ala
        35                  40                  45

Arg Lys Met Met Thr Lys Val Leu Asn Leu Thr Ser Ile Ile Asp Asp
    50                  55                  60

Thr Phe Asp Ala Tyr Ala Thr Phe Asp Glu
65                  70

<210> SEQ ID NO 12
<211> LENGTH: 74
<212> TYPE: PRT
<213> ORGANISM: M. piperita

<400> SEQUENCE: 12

Leu Tyr Lys Glu Glu Leu Ser Gln Leu Ser Arg Trp Trp Asn Thr Trp
1               5                   10                  15

Asn Leu Lys Ser Lys Leu Pro Tyr Ala Arg Asp Arg Val Val Glu Ala
            20                  25                  30

Tyr Val Trp Gly Val Gly Tyr His Tyr Glu Pro Gln Tyr Ser Tyr Val
        35                  40                  45

Arg Met Gly Leu Ala Lys Gly Val Leu Ile Cys Gly Ile Met Asp Asp
    50                  55                  60

Thr Tyr Asp Asn Tyr Ala Thr Leu Asn Glu
65                  70

<210> SEQ ID NO 13
<211> LENGTH: 73
<212> TYPE: PRT
<213> ORGANISM: A. grandis

<400> SEQUENCE: 13

Lys His His Lys Glu Ile Gln Phe Ile Thr Arg Trp Trp Arg Asp Ser
1               5                   10                  15

Gly Ile Ser Gln Leu Asn Phe Tyr Arg Lys Arg His Val Glu Tyr Tyr
            20                  25                  30

Ser Trp Val Val Met Cys Ile Phe Glu Pro Glu Phe Ser Glu Ser Arg
        35                  40                  45

Ile Ala Phe Ala Lys Thr Ala Ile Leu Cys Thr Val Leu Asp Asp Leu
    50                  55                  60

Tyr Asp Thr His Ala Thr Leu His Glu
65                  70

<210> SEQ ID NO 14
<211> LENGTH: 74
<212> TYPE: PRT
<213> ORGANISM: Citrus junos

```
<400> SEQUENCE: 14

Ile His Gln Lys Glu Leu Ser Ala Ile Thr Arg Trp Trp Lys Asp Leu
1               5                   10                  15

Asp Phe Thr Thr Lys Leu Pro Tyr Ala Arg Asp Arg Ile Val Glu Leu
            20                  25                  30

Tyr Phe Trp Ile Val Gly Thr Tyr Phe Glu Pro Lys Tyr Thr Leu Ala
        35                  40                  45

Arg Lys Ile Met Thr Lys Thr Ile Tyr Thr Ala Ser Ile Ile Asp Asp
    50                  55                  60

Thr Phe Asp Ala Tyr Gly Phe Phe Glu Glu
65                  70

<210> SEQ ID NO 15
<211> LENGTH: 73
<212> TYPE: PRT
<213> ORGANISM: Nicotiana tabacum

<400> SEQUENCE: 15

Leu His Lys Gln Glu Leu Ala Gln Val Ser Arg Trp Trp Lys Asp Leu
1               5                   10                  15

Asp Phe Val Thr Thr Leu Pro Tyr Ala Arg Asp Arg Val Val Glu Cys
            20                  25                  30

Tyr Phe Trp Ala Leu Gly Val Tyr Phe Glu Pro Gln Tyr Ser Gln Ala
        35                  40                  45

Arg Val Met Leu Val Lys Thr Ile Ser Met Ile Ser Ile Val Asp Asp
    50                  55                  60

Thr Phe Asp Ala Tyr Gly Thr Val Lys
65                  70

<210> SEQ ID NO 16
<211> LENGTH: 74
<212> TYPE: PRT
<213> ORGANISM: C. annuum

<400> SEQUENCE: 16

Leu His Lys Gln Glu Leu Ala Glu Val Ser Arg Trp Trp Lys Asp Leu
1               5                   10                  15

Asn Phe Val Asn Thr Leu Pro Tyr Ala Arg Asp Arg Val Val Glu Cys
            20                  25                  30

Tyr Phe Trp Ala Leu Gly Val Tyr Tyr Glu Pro Gln Tyr Ser Gln Ala
        35                  40                  45

Arg Val Met Leu Val Lys Thr Ile Ala Met Ile Ser Ile Val Asp Asp
    50                  55                  60

Thr Tyr Asp Ala Tyr Gly Thr Val Asp Glu
65                  70

<210> SEQ ID NO 17
<211> LENGTH: 74
<212> TYPE: PRT
<213> ORGANISM: Solanum tuberosum

<400> SEQUENCE: 17

Leu His Lys His Glu Leu Ser Glu Val Ser Arg Trp Trp Lys Asp Leu
1               5                   10                  15

Asp Phe Val Thr Thr Leu Pro Tyr Ala Arg Asp Arg Ala Val Glu Cys
            20                  25                  30

Tyr Phe Trp Thr Met Gly Val Tyr Ala Glu Pro Gln Tyr Ser Gln Ala
```

```
                35                  40                  45
Arg Val Ile Leu Ala Lys Thr Ile Ala Met Ile Ser Ile Val Asp Asp
        50                  55                  60

Thr Phe Asp Ala Tyr Gly Ile Val Lys Glu
65                  70

<210> SEQ ID NO 18
<211> LENGTH: 74
<212> TYPE: PRT
<213> ORGANISM: H. muticus

<400> SEQUENCE: 18

Leu His Lys His Glu Leu Ser Glu Val Ser Arg Trp Trp Lys Asp Leu
1               5                   10                  15

Asp Phe Val Thr Thr Leu Pro Tyr Ala Arg Asp Arg Ala Val Glu Cys
                20                  25                  30

Tyr Phe Trp Thr Met Gly Val Tyr Ala Glu Pro Gln Tyr Ser Gln Ala
            35                  40                  45

Arg Val Met Leu Ala Lys Thr Ile Ala Met Ile Ser Ile Val Asp Asp
        50                  55                  60

Thr Phe Asp Ala Tyr Gly Ile Val Lys Glu
65                  70

<210> SEQ ID NO 19
<211> LENGTH: 86
<212> TYPE: PRT
<213> ORGANISM: G. arboreum

<400> SEQUENCE: 19

Leu Glu Phe Ala Lys Ile Asp Phe Asn Met Val Gln Leu Leu His Arg
1               5                   10                  15

Lys Glu Leu Ser Glu Ile Ser Arg Trp Trp Lys Asp Leu Asp Phe Gln
                20                  25                  30

Arg Lys Leu Pro Tyr Ala Arg Asp Arg Val Val Glu Gly Tyr Phe Trp
            35                  40                  45

Ile Ser Gly Val Tyr Phe Glu Pro Gln Tyr Ser Leu Gly Arg Lys Met
        50                  55                  60

Leu Thr Lys Val Ile Ala Met Ala Ser Ile Val Asp Asp Thr Tyr Asp
65                  70                  75                  80

Ser Tyr Ala Thr Tyr Glu
                85

<210> SEQ ID NO 20
<211> LENGTH: 86
<212> TYPE: PRT
<213> ORGANISM: A. annua

<400> SEQUENCE: 20

Leu Lys Leu Ala Lys Leu Glu Phe Asn Leu Leu Gln Ser Leu His Lys
1               5                   10                  15

Glu Glu Leu Ser His Val Cys Lys Trp Trp Lys Ala Phe Asp Ile Lys
                20                  25                  30

Lys Asn Ala Pro Cys Leu Arg Asp Arg Ile Val Glu Cys Tyr Phe Trp
            35                  40                  45

Gly Leu Gly Ser Gly Tyr Glu Pro Gln Tyr Ser Arg Ala Arg Val Phe
        50                  55                  60

Phe Thr Lys Ala Val Ala Val Ile Thr Leu Ile Asp Asp Thr Tyr Asp
65                  70                  75                  80
```

```
Ala Tyr Gly Thr Tyr Glu
                85

<210> SEQ ID NO 21
<211> LENGTH: 86
<212> TYPE: PRT
<213> ORGANISM: A. annua

<400> SEQUENCE: 21

Leu Lys Leu Ala Lys Leu Gly Phe Asn Gln Leu Gln Ser Leu His Lys
1               5                   10                  15

Lys Glu Leu Ser Ile Ile Ser Lys Trp Trp Lys Ser Phe Asp Val Ala
            20                  25                  30

Asn Asn Leu Pro Tyr Ala Arg Asn Arg Pro Val Glu Cys Tyr Phe Trp
        35                  40                  45

Ala Leu Ala Val Tyr Phe Glu Pro Gln Tyr Ser Glu Ser Arg Val Phe
    50                  55                  60

Leu Ser Arg Phe Phe Ser Ile Gln Thr Phe Leu Asp Asp Thr Tyr Asp
65                  70                  75                  80

Ala Tyr Gly Thr Tyr Glu
                85

<210> SEQ ID NO 22
<211> LENGTH: 85
<212> TYPE: PRT
<213> ORGANISM: A. grandis

<400> SEQUENCE: 22

Leu Glu Leu Ala Lys Leu Asp Phe Asn Ile Leu Gln Cys Thr His Gln
1               5                   10                  15

Lys Glu Leu Gln Ile Ile Ser Arg Trp Phe Ala Asp Ser Ser Ile Ala
            20                  25                  30

Ser Leu Asn Phe Tyr Arg Lys Cys Tyr Val Glu Phe Tyr Phe Trp Met
        35                  40                  45

Ala Ala Ala Ile Ser Glu Pro Glu Phe Ser Gly Ser Arg Val Ala Phe
    50                  55                  60

Thr Lys Ile Ala Ile Leu Met Thr Met Leu Asp Asp Leu Tyr Asp Thr
65                  70                  75                  80

His Gly Thr Leu Asp
                85

<210> SEQ ID NO 23
<211> LENGTH: 18
<212> TYPE: DNA
<213> ORGANISM: Artificial Sequence
<220> FEATURE:
<223> OTHER INFORMATION: Primer deduced (Example 1)

<400> SEQUENCE: 23
hhvthwcmmg gtggtgga                                                 18

<210> SEQ ID NO 24
<211> LENGTH: 18
<212> TYPE: DNA
<213> ORGANISM: Artificial Sequence
<220> FEATURE:
<223> OTHER INFORMATION: Primer deduced (Example 1)
<220> FEATURE:
<221> NAME/KEY: misc_feature
<222> LOCATION: (3)..(3)
<223> OTHER INFORMATION: can be G, A, C or T
```

```
<400> SEQUENCE: 24
gtngarkbbt atktttgg                                              18

<210> SEQ ID NO 25
<211> LENGTH: 22
<212> TYPE: DNA
<213> ORGANISM: Artificial Sequence
<220> FEATURE:
<223> OTHER INFORMATION: Primer deduced (Example 1)

<400> SEQUENCE: 25
crtrrktrtc gwadgkgtcr tc                                         22

<210> SEQ ID NO 26
<211> LENGTH: 25
<212> TYPE: DNA
<213> ORGANISM: Artificial Sequence
<220> FEATURE:
<223> OTHER INFORMATION: Primer deduced (Example 1)

<400> SEQUENCE: 26
gckaagwtvg gkttcaathw kbtdc                                      25

<210> SEQ ID NO 27
<211> LENGTH: 29
<212> TYPE: DNA
<213> ORGANISM: Artificial Sequence
<220> FEATURE:
<223> OTHER INFORMATION: Primer deduced (Example 1)
<220> FEATURE:
<221> NAME/KEY: misc_feature
<222> LOCATION: (9)..(9)
<223> OTHER INFORMATION: can be a, t, g, or c

<400> SEQUENCE: 27
gggawwgwnw bgttgaakkt tatttttgg                                  29

<210> SEQ ID NO 28
<211> LENGTH: 23
<212> TYPE: DNA
<213> ORGANISM: Artificial Sequence
<220> FEATURE:
<223> OTHER INFORMATION: Primer deduced (Example 1)
<220> FEATURE:
<221> NAME/KEY: misc_feature
<222> LOCATION: (8)..(8)
<223> OTHER INFORMATION: can be a, t, g, or c

<400> SEQUENCE: 28
gtwscgtngh gtcgtahgtc atc                                        23

<210> SEQ ID NO 29
<211> LENGTH: 49
<212> TYPE: PRT
<213> ORGANISM: Citrus paradisi

<400> SEQUENCE: 29

Asp Leu Gly Phe Pro Lys Lys Val Pro Tyr Ala Arg Asp Arg Val Val
1               5                   10                  15

Glu Thr Tyr Ile Trp Met Leu Leu Gly Val Ser Tyr Glu Pro Asn Leu
            20                  25                  30

Ala Phe Gly Arg Ile Phe Ala Ser Lys Val Val Cys Ile Ile Ser Ile
        35                  40                  45

Ile
```

<210> SEQ ID NO 30
<211> LENGTH: 27
<212> TYPE: PRT
<213> ORGANISM: Citrus paradisi

<400> SEQUENCE: 30

Ile Val Gly Thr Tyr Phe Glu Pro Lys Tyr Thr Leu Ala Arg Lys Ile
1               5                   10                  15
Met Thr Lys Thr Ile Tyr Thr Ala Ser Ile Ile
            20                  25

<210> SEQ ID NO 31
<211> LENGTH: 26
<212> TYPE: PRT
<213> ORGANISM: Citrus paradisi

<400> SEQUENCE: 31

Met Gly Val Tyr Phe Glu Pro Arg Tyr Ser Phe Ala Arg Lys Ile Leu
1               5                   10                  15
Ser Lys Val Ile Ala Met Ala Ser Ile Leu
            20                  25

<210> SEQ ID NO 32
<211> LENGTH: 260
<212> TYPE: PRT
<213> ORGANISM: Citrus paradisi

<400> SEQUENCE: 32

Gln Lys Leu His Met Ile Asp Ala Ala Gln Arg Leu Gly Val Ala Tyr
1               5                   10                  15
His Phe Glu Lys Glu Ile Glu Asp Glu Leu Gly Lys Val Ser His Asp
            20                  25                  30
Leu Asp Ser Asp Leu Tyr Val Val Ser Leu Arg Phe Arg Leu Phe
        35                  40                  45
Arg Gln Gln Gly Val Lys Ile Ser Cys Asp Val Phe Glu Lys Phe Lys
50                  55                  60
Asp Asp Glu Gly Lys Phe Lys Glu Ser Leu Ile Asn Asp Ile Arg Gly
65                  70                  75                  80
Met Ser Ser Leu Tyr Glu Ala Ala Tyr Leu Ala Ile Arg Gly Glu Asp
                85                  90                  95
Ile Leu Asp Glu Ala Ile Val Phe Thr Thr Thr His Leu Lys Ser Val
            100                 105                 110
Ile Ser Val Ser Asp His Ser His Val Asn Ser Asp Leu Ala Glu Gln
        115                 120                 125
Ile Arg His Ser Leu Gln Ile Pro Leu Arg Lys Ala Ala Ala Arg Leu
    130                 135                 140
Glu Ala Arg Tyr Phe Leu Asp Ile Tyr Ser Arg Asp Asp Leu His Asp
145                 150                 155                 160
Glu Thr Leu Leu Lys Phe Ala Lys Leu Asp Phe Asn Ile Leu Gln Ala
                165                 170                 175
Ala His Lys Lys Glu Ala Ser Ile Met Thr Arg Trp Trp Asn Asp Leu
            180                 185                 190
Gly Phe Pro Lys Lys Val Pro Tyr Ala Arg Asp Arg Val Val Glu Thr
        195                 200                 205
Tyr Ile Trp Met Leu Leu Gly Val Ser Tyr Glu Pro Asn Leu Ala Phe
    210                 215                 220

```
Gly Arg Ile Phe Ala Ser Lys Val Val Cys Ile Ser Ile Ile Asp
225                 230                 235                 240

Asp Thr Phe Asp Ala Tyr Gly Thr Phe Glu Glu Leu Thr Leu Phe Thr
                245                 250                 255

Glu Ala Val Thr
            260

<210> SEQ ID NO 33
<211> LENGTH: 780
<212> TYPE: DNA
<213> ORGANISM: Citrus paradisi

<400> SEQUENCE: 33
caaaaactac acatgattga tgcagcacaa cgattaggtg tcgcttatca ttttgaaaaa      60
gagattgaag atgaattggg aaaggtatct catgatcttg acagtgatga tctatacgtt     120
gtttctcttc gttttcgact ttttagacag caaggagtta agatttcatg tgatgtgttt     180
gagaagttca agatgacga aggtaaattc aaggaatcat tgatcaacga tatacgaggc      240
atgtcgagtt tgtacgaggc agcataccta gcaattcggg gggaagacat tttagatgaa     300
gccattgttt tcactaccac tcaccttaag tcagtaatat ctgtatctga tcattctcat     360
gtaaactctg atcttgctga acaaatacgt cattctctgc aaattcctct ccgtaaagcc     420
gcagcaaggt tagaggcaag gtattttttg gatatctatt caagggatga tttgcatgat     480
gaaactttgc tcaagtttgc aaagttagac tttaatatat tacaagcagc acacaagaag     540
gaagcaagta tcatgaccag gtggtggaac gatttaggct tccctaaaaa ggtgccttat     600
gcaagagata gagtagtaga gacatatatt tggatgttgc tgggagtgtc ctatgagccc     660
aatttggcat tggtagaat ttttgcatcc aaagtggtgt gcataatatc cataatagac     720
gacacatttg atgcttacgg tacttttgaa gagctcacac ttttactga agcagtcaca     780

<210> SEQ ID NO 34
<211> LENGTH: 28
<212> TYPE: DNA
<213> ORGANISM: Artificial sequence
<220> FEATURE:
<223> OTHER INFORMATION: Primer deduced

<400> SEQUENCE: 34
ctgggagtgt cctatgagct caatttgg                                          28

<210> SEQ ID NO 35
<211> LENGTH: 29
<212> TYPE: DNA
<213> ORGANISM: Artificial sequence
<220> FEATURE:
<223> OTHER INFORMATION: Primer deduced

<400> SEQUENCE: 35
gtagaatttt tgcatccaaa gtggtgtgc                                         29

<210> SEQ ID NO 36
<211> LENGTH: 28
<212> TYPE: DNA
<213> ORGANISM: Artificial  sequence
<220> FEATURE:
<223> OTHER INFORMATION: Primer deduced

<400> SEQUENCE: 36
cacaccactt tggatgcaaa aattcatc                                          28
```

<210> SEQ ID NO 37
<211> LENGTH: 28
<212> TYPE: DNA
<213> ORGANISM: Artificial sequence
<220> FEATURE:
<223> OTHER INFORMATION: Primer deduced

<400> SEQUENCE: 37
ccaaattggg ctcataggac actcccag                                              28

<210> SEQ ID NO 38
<211> LENGTH: 26
<212> TYPE: DNA
<213> ORGANISM: Artificial sequence
<220> FEATURE:
<223> OTHER INFORMATION: Primer deduced

<400> SEQUENCE: 38
tagggacgta ttttgaacca aagtac                                                26

<210> SEQ ID NO 39
<211> LENGTH: 27
<212> TYPE: DNA
<213> ORGANISM: Artificial sequence
<220> FEATURE:
<223> OTHER INFORMATION: Primer deduced

<400> SEQUENCE: 39
aaataatgac caaaacaatt tacacgg                                               27

<210> SEQ ID NO 40
<211> LENGTH: 22
<212> TYPE: DNA
<213> ORGANISM: Artificial sequence
<220> FEATURE:
<223> OTHER INFORMATION: Primer deduced

<400> SEQUENCE: 40
gcactttcat gtattctgga ag                                                    22

<210> SEQ ID NO 41
<211> LENGTH: 22
<212> TYPE: DNA
<213> ORGANISM: Artificial sequence
<220> FEATURE:
<223> OTHER INFORMATION: Primer deduced

<400> SEQUENCE: 41
gtttgagctc ttcaaagaaa cc                                                    22

<210> SEQ ID NO 42
<211> LENGTH: 31
<212> TYPE: DNA
<213> ORGANISM: Artificial sequence
<220> FEATURE:
<223> OTHER INFORMATION: Primer deduced

<400> SEQUENCE: 42
aatgggagtg tattttgagc ctcgatactc c                                          31

<210> SEQ ID NO 43
<211> LENGTH: 31
<212> TYPE: DNA
<213> ORGANISM: Artificial sequence
<220> FEATURE:
<223> OTHER INFORMATION: Primer deduced

<400> SEQUENCE: 43
gatattttcc aaagtaattg caatggcatc c          31

<210> SEQ ID NO 44
<211> LENGTH: 27
<212> TYPE: DNA
<213> ORGANISM: Artificial sequence
<220> FEATURE:
<223> OTHER INFORMATION: Primer deduced

<400> SEQUENCE: 44
gttgctaata tcccaccttt tgatagc          27

<210> SEQ ID NO 45
<211> LENGTH: 23
<212> TYPE: DNA
<213> ORGANISM: Artificial sequence
<220> FEATURE:
<223> OTHER INFORMATION: Primer deduced

<400> SEQUENCE: 45
aagtgtgcca taggcgtcgt agg          23

<210> SEQ ID NO 46
<211> LENGTH: 27
<212> TYPE: DNA
<213> ORGANISM: Artificial sequence
<220> FEATURE:
<223> OTHER INFORMATION: Primer deduced

<400> SEQUENCE: 46
ctgttccgca agcttagggg ttacatg          27

<210> SEQ ID NO 47
<211> LENGTH: 29
<212> TYPE: DNA
<213> ORGANISM: Artificial sequence
<220> FEATURE:
<223> OTHER INFORMATION: Primer deduced

<400> SEQUENCE: 47
ctgagctacc aatgacttca ggtgagtgg          29

<210> SEQ ID NO 48
<211> LENGTH: 31
<212> TYPE: DNA
<213> ORGANISM: Artificial sequence
<220> FEATURE:
<223> OTHER INFORMATION: Primer deduced

<400> SEQUENCE: 48
caattttgcc atacacatca tagatatcat c          31

<210> SEQ ID NO 49
<211> LENGTH: 28
<212> TYPE: DNA
<213> ORGANISM: Artificial sequence
<220> FEATURE:
<223> OTHER INFORMATION: Primer deduced

<400> SEQUENCE: 49
aacagaagtc atggagatca ctttcgtc          28

<210> SEQ ID NO 50

```
<211> LENGTH: 28
<212> TYPE: DNA
<213> ORGANISM: Artificial sequence
<220> FEATURE:
<223> OTHER INFORMATION: Primer deduced

<400> SEQUENCE: 50
cgcaagagat gttttaaagt tcccatcc                                    28

<210> SEQ ID NO 51
<211> LENGTH: 26
<212> TYPE: DNA
<213> ORGANISM: Artificial sequence
<220> FEATURE:
<223> OTHER INFORMATION: Primer deduced

<400> SEQUENCE: 51
tgaacatcag cggaaatttt atagcc                                      26

<210> SEQ ID NO 52
<211> LENGTH: 24
<212> TYPE: DNA
<213> ORGANISM: Artificial sequence
<220> FEATURE:
<223> OTHER INFORMATION: Primer deduced

<400> SEQUENCE: 52
acgatttagg cttccctaaa aagg                                        24

<210> SEQ ID NO 53
<211> LENGTH: 25
<212> TYPE: DNA
<213> ORGANISM: Artificial sequence
<220> FEATURE:
<223> OTHER INFORMATION: Primer deduced

<400> SEQUENCE: 53
tattatggaa tattatgcac accac                                       25

<210> SEQ ID NO 54
<211> LENGTH: 27
<212> TYPE: DNA
<213> ORGANISM: Artificial sequence
<220> FEATURE:
<223> OTHER INFORMATION: Primer deduced

<400> SEQUENCE: 54
aaatgtccgc tcaagttcta gcaacgg                                     27

<210> SEQ ID NO 55
<211> LENGTH: 26
<212> TYPE: DNA
<213> ORGANISM: Artificial sequence
<220> FEATURE:
<223> OTHER INFORMATION: Primer deduced

<400> SEQUENCE: 55
atggcacttc aagattcaga agttcc                                      26

<210> SEQ ID NO 56
<211> LENGTH: 41
<212> TYPE: DNA
<213> ORGANISM: Artificial sequence
<220> FEATURE:
<223> OTHER INFORMATION: Primer deduced

<400> SEQUENCE: 56
```

```
gcatgttcca tatgtccgct caagttctag caacggtttc c                41
```

<210> SEQ ID NO 57
<211> LENGTH: 39
<212> TYPE: DNA
<213> ORGANISM: Artificial sequence
<220> FEATURE:
<223> OTHER INFORMATION: Primer deduced

<400> SEQUENCE: 57

```
cgcggatcct cagatggtaa cagggtctct gagcactgc                  39
```

<210> SEQ ID NO 58
<211> LENGTH: 37
<212> TYPE: DNA
<213> ORGANISM: Artificial sequence
<220> FEATURE:
<223> OTHER INFORMATION: Primer deduced

<400> SEQUENCE: 58

```
gcatgttcca tatgtcgtct ggagaaacat ttcgtcc                    37
```

<210> SEQ ID NO 59
<211> LENGTH: 33
<212> TYPE: DNA
<213> ORGANISM: Artificial sequence
<220> FEATURE:
<223> OTHER INFORMATION: Primer deduced

<400> SEQUENCE: 59

```
cgcggatcct caaaatggaa cgtggtctcc tag                        33
```

<210> SEQ ID NO 60
<211> LENGTH: 39
<212> TYPE: DNA
<213> ORGANISM: Artificial sequence
<220> FEATURE:
<223> OTHER INFORMATION: Primer deduced

<400> SEQUENCE: 60

```
gcatgttcca tatgtctttg gaagtttcag cctctcctg                  39
```

<210> SEQ ID NO 61
<211> LENGTH: 42
<212> TYPE: DNA
<213> ORGANISM: Artificial sequence
<220> FEATURE:
<223> OTHER INFORMATION: Primer deduced

<400> SEQUENCE: 61

```
cgcggatcct catatcggca caggattaat aaacaaagaa gc              42
```

<210> SEQ ID NO 62
<211> LENGTH: 30
<212> TYPE: DNA
<213> ORGANISM: Artificial sequence
<220> FEATURE:
<223> OTHER INFORMATION: Primer deduced

<400> SEQUENCE: 62

```
taatggcact tcaagattca gaagttcctc                            30
```

<210> SEQ ID NO 63
<211> LENGTH: 27
<212> TYPE: DNA

```
<213> ORGANISM: Artificial sequence
<220> FEATURE:
<223> OTHER INFORMATION: Primer deduced

<400> SEQUENCE: 63
aaaagggaac aggcttctca agcaatg                                              27

<210> SEQ ID NO 64
<211> LENGTH: 28
<212> TYPE: DNA
<213> ORGANISM: Artificial sequence
<220> FEATURE:
<223> OTHER INFORMATION: Primer deduced

<400> SEQUENCE: 64
atggcacttc aagattcaga agttcctc                                             28

<210> SEQ ID NO 65
<211> LENGTH: 31
<212> TYPE: DNA
<213> ORGANISM: Artificial sequence
<220> FEATURE:
<223> OTHER INFORMATION: Primer deduced

<400> SEQUENCE: 65
gatcaaaagg gaacaggctt ctcaagcaat g                                         31
```